(12) United States Patent
Takasaki et al.

(10) Patent No.: US 8,785,088 B2
(45) Date of Patent: Jul. 22, 2014

(54) COLORED COMPOSITION, COLORED CURED FILM, COLOR FILTER, METHOD FOR PRODUCING COLOR FILTER, LIQUID CRYSTAL DISPLAY DEVICE, SOLID-STATE IMAGING DEVICE, AND NOVEL DIPYRROMETHENE METAL COMPLEX COMPOUND OR TAUTOMER THEREOF

(71) Applicant: Fujifilm Corporation, Tokyo (JP)

(72) Inventors: Yuta Takasaki, Shizuoka-ken (JP); Daisuke Sasaki, Shizuoka-ken (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/042,737

(22) Filed: Oct. 1, 2013

(65) Prior Publication Data

US 2014/0030642 A1    Jan. 30, 2014

Related U.S. Application Data

(63) Continuation of application No. PCT/JP2012/059416, filed on Apr. 5, 2012.

(30) Foreign Application Priority Data

Apr. 5, 2011  (JP) ................................ 2011-083546

(51) Int. Cl.
  *G02B 5/20*       (2006.01)
(52) U.S. Cl.
  USPC ......... 430/7; 430/270.1; 430/281.1; 548/402; 548/403
(58) Field of Classification Search
  None
  See application file for complete search history.

(56) References Cited

U.S. PATENT DOCUMENTS

| 2012/0187351 A1* | 7/2012 | Ito et al. ................. 252/586 |
| 2012/0264039 A1* | 10/2012 | Ito et al. ................. 430/7 |
| 2013/0012648 A1* | 1/2013 | Fujie et al. .............. 524/547 |

FOREIGN PATENT DOCUMENTS

| JP | H06-75375 A | 3/1994 |
| JP | 2001-108815 A | 4/2001 |
| JP | 2008-292970 A | 12/2008 |
| JP | 2011-180307 A | 9/2011 |

OTHER PUBLICATIONS

International Search Report issued in International Application No. PCT/JP2012/059416 on Jun. 5, 2012.
Written Opinion of the ISA issued in International Application No. PCT/JP2012/059416 on Jun. 5, 2012.

\* cited by examiner

*Primary Examiner* — John A. McPherson
(74) *Attorney, Agent, or Firm* — SOLARIS Intellectual Property Group, PLLC

(57) ABSTRACT

Provided is a colored composition including at least one selected from the group consisting of a compound represented by the following formula (I) and a tautomer thereof: wherein in formula (I), $R^2$ to $R^5$ each independently represent a hydrogen atom or a monovalent substituent; $R^7$ represents a hydrogen atom, a halogen atom, an alkyl group, an aryl group or a heterocyclic group; Ma represents a metal or a metal compound; $X^3$ and $X^4$ each independently represent NR, a nitrogen atom, an oxygen atom, or a sulfur atom, wherein R represents a hydrogen atom, an alkyl group, an alkenyl group, an aryl group, a heterocyclic group, an acyl group, an alkylsulfonyl group, or an arylsulfonyl group; $X^5$ represents a group required to neutralize the charge of Ma; a represents 1 or 2; and $R^8$ to $R^{17}$ each independently represent a hydrogen atom or a monovalent substituent, provided that at least one of $R^8$ to $R^{17}$ represents a particular polymerizable substituent.

17 Claims, No Drawings

COLORED COMPOSITION, COLORED CURED FILM, COLOR FILTER, METHOD FOR PRODUCING COLOR FILTER, LIQUID CRYSTAL DISPLAY DEVICE, SOLID-STATE IMAGING DEVICE, AND NOVEL DIPYRROMETHENE METAL COMPLEX COMPOUND OR TAUTOMER THEREOF

CROSS-REFERENCE TO RELATED APPLICATIONS

This application is a continuation application of International Application No. PCT/JP/2012/059416, filed Apr. 5, 2012, the disclosure of which is incorporated herein by reference in its entirety. Further, this application claims priority from Japanese Patent Application No. 2011-083546, filed Apr. 5, 2011, the disclosure of which is incorporated herein by reference in its entirety.

TECHNICAL FIELD

The present invention relates to a colored composition, a colored cured film, a color filter, a method for producing a color filter, a liquid crystal display device, a solid-state imaging device, and a novel dipyrromethene-metal complex compound or a tautomer thereof.

BACKGROUND ART

Color filters have been conventionally produced by preparing a colored photosensitive composition containing a pigment dispersion composition in which an organic pigment or an inorganic pigment is dispersed, and also containing a polyfunctional monomer, a polymerization initiator, an alkali-soluble resin, and other components, and forming a colored pattern by a photolithographic method, an inkjet method or the like using this colored photosensitive composition.

In recent years, there has been a tendency for the use application of color filters in liquid crystal display devices (LCD) to be extended to televisions (TV) in addition to monitors. Along with this tendency of expansion in their use, color filters are now required to have high-level color characteristics in terms of chromaticity, contrast and the like. Furthermore, even color filters for use in image sensors (solid-state imaging devices) are also similarly required to have high-level color characteristics such as a decrease in color unevenness and an increase in color resolution.

However, in the conventional pigment dispersion systems, problems such as the occurrence of scattering due to coarse pigment particles, and an increase in viscosity due to poor dispersion stability, easily occur, and it is often difficult to further increase the contrast and luminance.

Thus, it has been hitherto investigated to use not only pigments but also dyes as colorants (see, for example, Patent Document 1). When dyes are used as colorants, due to the color purity of the dyes themselves or due to the vividness of the colors, the hue or luminance of the display images at the time of image display can be increased, and since coarse particles are not present, the contrast is increased. Thus, dye colorants are considered useful from this point of view.

In particular, dipyrromethene-based dyes containing a dipyrromethene-metal complex compound as a colorant structure are known as dyes having high color purity and excellent heat resistance or light resistance (see, for example, Patent Documents 2 and 3).

CITATION LIST

Patent Document

Patent Document 1: Japanese Patent Application Laid-Open (JP-A) No. H6-75375
Patent Document 2: JP-A No. 2008-292970
Patent Document 3: JP-A No. 2010-848414

SUMMARY OF INVENTION

Technical Problem

However, when a dye is used in a colored composition for producing a color filter, a decrease in light resistance easily occurs as compared with the case of using a conventional pigment. Furthermore, when a color filter produced using a dye is applied to a liquid crystal display device, a decrease in the voltage retention ratio easily occurs. In particular, since the decrease in the voltage retention ratio causes an increase in the driving voltage, an increase in the consumed power, a decrease in contrast, display unevenness, or discoloration, it is preferable that the decrease in voltage retention ratio be reduced as much as possible.

Furthermore, the above-mentioned compound that is a conventionally well-known dye exhibits insufficient light resistance when a color filter is produced using a colored composition containing this compound. Furthermore, when the color filter is applied to a liquid crystal display device, the voltage retention ratio is insufficient, and an improvement of the displayed image quality is desired.

The present invention was achieved in view of such circumstances, and objects of the invention are to provide a colored composition which is useful for the production of a color filter, has high color purity, gives a high extinction coefficient when formed into a thin film, is capable of forming a colored cured film having excellent fastness properties (in particular, light resistance), and gives an excellent voltage retention ratio when a voltage is applied to a liquid crystal display device equipped with a color filter including the colored cured film; a colored cured film obtained using the colored composition; a color filter and a method of production thereof; a liquid crystal display device which exhibits clear coloring of display images and high contrast; and a solid-state imaging device which has reduced color unevenness and improved color resolution. Thus, achieving these objects are problems to be solved.

Furthermore, a further object of the invention is to provide a novel dipyrromethene-metal complex compound and a tautomer thereof, each of which has excellent color purity, a high extinction coefficient enabling the formation of thin layers, and excellent fastness properties (in particular, light resistance), and is useful for the formation of a colored film that is included in a color filter. Thus, achieving this object is another problem to be solved.

Solution to Problem

Specific means to solve the problem described above are as follows.

<1> A colored composition including at least one selected from the group consisting of a compound represented by the following formula (I) and a tautomer thereof Formula (I)

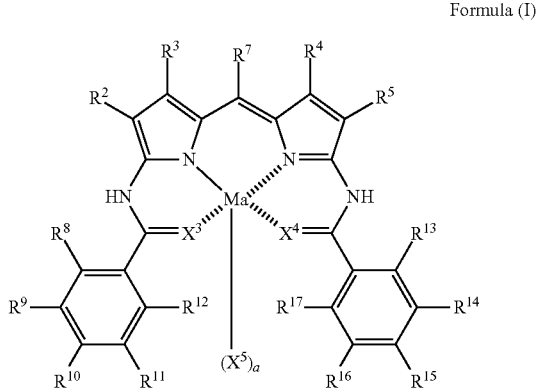

In formula (I), $R^2$ to $R^5$ each independently represent a hydrogen atom or a monovalent substituent; $R^7$ represents a hydrogen atom, a halogen atom, an alkyl group, an aryl group or a heterocyclic group; Ma represents a metal or a metal compound; $X^3$ and $X^4$ each independently represent NR, a nitrogen atom, an oxygen atom, or a sulfur atom, wherein R represents a hydrogen atom, an alkyl group, an alkenyl group, an aryl group, a heterocyclic group, an acyl group, an alkylsulfonyl group, or an arylsulfonyl group; $X^5$ represents a group required to neutralize the charge of Ma; a represents 1 or 2; when a is 2, respective $X^5$'s may be identical to or different from each other; and $R^8$ to $R^{17}$ each independently represent a hydrogen atom or a monovalent substituent, provided that at least one of $R^8$ to $R^{17}$ represents a substituent represented by the following formula (II).

Formula (II)

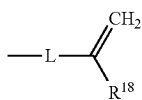

In formula (II), $R^{18}$ represents a hydrogen atom or a methyl group; L represents a single bond or a divalent linking group; and when the compound represented by formula (I) or a tautomer thereof has plural substituents represented by formula (II), the respective substituents may be identical to or different from each other.

<2> The colored composition according to <1>, wherein, in formula (I), at least any one of $R^8$ to $R^{12}$ is a substituent represented by formula (II), and at least any one of $R^{13}$ to $R^{17}$ is a substituent represented by formula (II).

<3> The colored composition according to <1> or <2>, further including a polymerizable compound and a photopolymerization initiator.

<4> The colored composition according to any one of <1> to <3>, further including a pigment or an anthraquinone compound, or including both a pigment and an anthraquinone compound.

<5> The colored composition according to <4>, wherein the anthraquinone compound is a compound represented by the following formula (IX).

Formula (IX)

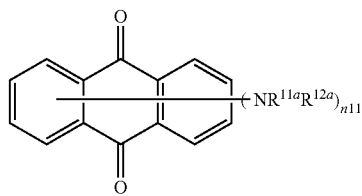

In formula (IX), $R^{11a}$ and $R^{12a}$ each independently represent a hydrogen atom, an alkyl group, an aryl group, or a heterocyclic group, but $R^{11a}$ and $R^{12a}$ do not simultaneously represent hydrogen atoms; $n^{11}$ represents an integer from 1 to 4; and when $n^{11}$ represents an integer from 2 to 4, plural $NR^{11a}R^{12a}$'s may be identical to or different from each other.

<6> The colored composition according to any one of <1> to <5>, wherein a content of the at least one selected from the group consisting of a compound represented by formula (I) and a tautomer thereof is 0.1% to 30% by mass relative to the total solid content of the colored composition.

<7> A colored cured film, obtained by curing the colored composition according to any one of <1> to <6>.

<8> A color filter, including the colored cured film according to <7>.

<9> A method for producing a color filter, the method including: a colored layer forming process of applying the colored composition according to any one of <1> to <6> onto a support to form a colored layer; and a colored cured film forming process of exposing the formed colored layer in a pattern form and developing the colored layer to form a patterned colored cured film.

<10> A liquid crystal display device, including the color filter according to <8> or, a color filter prepared by the method for producing a color filter according to <9>.

<11> A solid-state imaging device including the color filter according to <8> or, a color filter, prepared by the method for producing a color filter according to <9>.

<12> A compound represented by the following formula (I) or a tautomer thereof

Formula (I)

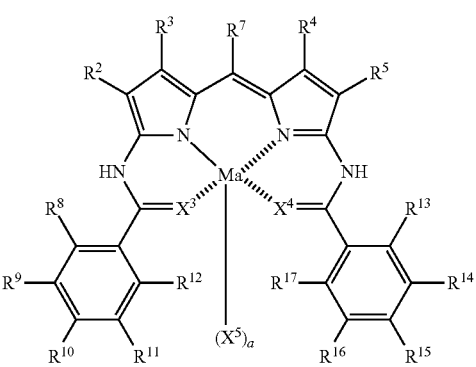

In formula (I), $R^2$ to $R^5$ each independently represent a hydrogen atom or a monovalent substituent; $R^7$ represents a hydrogen atom, a halogen atom, an alkyl group, an aryl group or a heterocyclic group; Ma represents a metal or a metal compound; $X^3$ and $X^4$ each independently represent NR (wherein R represents a hydrogen atom, an alkyl group, an alkenyl group, an aryl group, a heterocyclic group, an acyl group, an alkylsulfonyl group, or an arylsulfonyl group), a nitrogen atom, an oxygen atom, or a sulfur atom; $X^5$ represents a group required to neutralize the charge of Ma; a represents 1 or 2; when a is 2, respective $X^5$'s may be identical to or different from each other; and $R^8$ to $R^{17}$ each independently represent a hydrogen atom or a monovalent substituent, provided that at least one of $R^8$ to $R^{17}$ represents a substituent represented by the following formula (II).

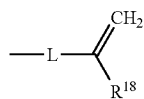

Formula (II)

In formula (II), $R^{18}$ represents a hydrogen atom or a methyl group; L represents a single bond or a divalent linking group; and when the compound represented by formula (I) or a tautomer thereof has plural substituents represented by formula (II), the respective substituents may be identical to or different from each other.

Advantageous Effects of Invention

According to the invention, a colored composition can be provided which is useful for the production of a color filter, has high color purity, is capable of giving a high extinction coefficient when formed into a thin film, is capable of forming a colored cured film having excellent fastness properties (in particular, light resistance), and is capable of giving an excellent voltage retention ratio when a voltage is applied to a liquid crystal display device equipped with a color filter including the colored cured film; a colored cured film obtained using the colored composition; a color filter; and a method of production thereof.

According to the invention, a liquid crystal display device exhibiting clear coloring of the display images and high contrast, and a solid-state imaging device having reduced color unevenness and improved color resolution, can be provided.

According to the invention, a novel dipyrromethene-metal complex compound or a tautomer thereof can be provided which has excellent color purity, a high extinction coefficient enabling the formation of thin layers, and excellent fastness properties (in particular, light resistance), and is useful for the formation of a colored film that is included in a color filter.

DESCRIPTION OF EMBODIMENTS

Hereinafter, a colored composition, a novel dipyrromethene-metal complex compound and a tautomer thereof that are useful in colored compositions, a color filter, a method for producing a color filter, a liquid crystal display device, and a solid-state imaging device, of the invention are described in detail. The explanation of the constituent elements that are described below may be based on representative exemplary embodiments of the invention, but the invention is not intended to be limited to such exemplary embodiments.

Meanwhile, the numerical value range represented by using "to" in the present specification means a range including the numerical values described before and after "to" as the lower limit and the upper limit.

The term "total solid content" as used in the present specification is the total content of all components of the colored composition, excluding the solvent that is a component of the colored composition.

In the present specification, for example, the "alkyl group" represents a "straight-chain, branched or cyclic" alkyl group. Furthermore, in regard to the notation of groups (atomic groups) in the present specification, notation that does not indicate whether a group is substituted or unsubstituted indicates a group including in its scope a group that does not have a substituent as well as a group that has a substituent. For example, the term "alkyl group" includes in its scope an alkyl group that does not have a substituent (unsubstituted alkyl group) as well as an alkyl group that has a substituent (substituted alkyl group).

Furthermore, in the present specification, the term "(meth) acrylate" means both or either of acrylate and methacrylate, and the term "(meth)acryl" means both or either of acryl and methacryl, while the term "(meth)acryloyl" means both or either of acryloyl and methacryloyl.

Furthermore, in the present specification, the terms "monomer" and "monomer" have the same meaning. The monomer according to the present specification refers to a compound which is distinguished from an oligomer and a polymer, and has a weight average molecular weight of 2,000 or less. In the present specification, a polymerizable compound refers to a compound having a polymerizable functional group, and may be a monomer, an oligomer or a polymer. The polymerizable functional group means a group involved in a polymerization reaction.

The term "process" according to the present specification includes not only an independent process, but also a process which can achieve a predetermined action even in the case where the relevant process cannot be clearly distinguished from another process.

The term "radiation" according to the invention include in its scope visible light, ultraviolet radiation, far-ultraviolet radiation, electron beams, X-rays, and the like.

The invention relates to a colored composition including at least one selected from the group consisting of a compound represented by formula (I) and a tautomer thereof.

The compound represented by formula (I) or a tautomer thereof has a polymerizable substituent represented by formula (II) at a particular position, so that when the compound represented by formula (I) or a tautomer thereof is used as a colorant, a color filter having an excellent voltage retention ratio, and excellent heat resistance, light resistance, contrast and luminance can be provided.

The action of the invention is not clearly understood but is speculated as follows.

That is, it is contemplated that a decrease in the voltage retention ratio of a color filter is caused by a metal complex compound dissolved out from the color filter into liquid crystals when an electric field is applied to the color filter. Therefore, it is speculated that if the metal complex compound could be immobilized in the film of the color filter, suppression of a decrease in the voltage retention ratio would be possible.

The compound represented by formula (I) or a tautomer thereof has a polymerizable substituent represented by formula (II) at a particular position, so that it is contemplated that in the exposure process or heat treatment process at the time of color filter production, when the compound or a tautomer thereof forms a covalent bond with another polymerizable component (for example, a monomer or a binder polymer) that is present in the color filter, the dipyrromethene-metal complex compound or a tautomer thereof is immobilized in the film, and dissolution into liquid crystals is suppressed.

<<Colored Composition>>

The colored composition of the invention includes at least one selected from the group consisting of a compound represented by formula (I) that is described below and a tautomer thereof, and the colored composition is preferably constituted as a composition which has photosensitivity, further using a polymerizable compound and a photopolymerization initiator.

Furthermore, the colored composition of the invention is preferably constituted to further include, if necessary, an alkali-soluble binder and an organic solvent, and can be constituted further using various additives, if necessary.

Moreover, the colored composition of the invention may include another dye or pigment having a structure different from the structure of the dipyrromethene-metal complex compound or a tautomer thereof of the invention, and a dispersion thereof.

<<Compound Represented by Formula (I) or Tautomeric Compound Thereof>>

The colored composition of the invention includes at least one selected from the group consisting of a compound represented by formula (I) that is described below and a tautomer thereof (hereinafter, may be appropriately referred to as "dipyrromethene-metal complex compound"), and two or more thereof may be used in combination.

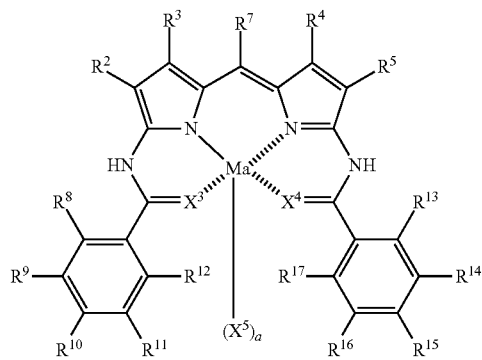

Formula (I)

In formula (I), $R^2$, $R^3$, $R^4$ and $R^5$ each independently represent a hydrogen atom or a monovalent substituent. $R^7$ represents a hydrogen atom, a halogen atom, an alkyl group, an aryl group, or a heterocyclic group. Ma represents a metal or a metal compound, and $X^3$ and $X^4$ each independently represent NR, a nitrogen atom, an oxygen atom, or a sulfur atom wherein R represents a hydrogen atom, an alkyl group, an alkenyl group, an aryl group, a heterocyclic group, an acyl group, an alkylsulfonyl group, or an arylsulfonyl group.

$X^5$ represents a group required to neutralize the charge of Ma, and a represents 1 or 2. When a is 2, respective $X^5$'s may be identical to or different from each other. $R^8$ to $R^{17}$ each independently represent a hydrogen atom or a monovalent substituent. However, at least one of $R^8$ to $R^{17}$ represents a substituent represented by the following formula (II).

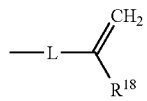

Formula (II)

In formula (II), $R^{18}$ represents a hydrogen atom or a methyl group. L represents a single bond or a divalent linking group. When the compound represented by formula (I) or a tautomer thereof has a plurality substituents represented by formula (II), the respective substituents may be identical to or different from each other.

Examples of the monovalent substituent represented by $R^2$ to $R^5$ in formula (I) include a halogen atom (examples include a fluorine atom, a chlorine atom, a bromine atom, and an iodine atom), an alkyl group (preferably, a straight-chain, branched or cyclic alkyl group having 1 to 48 carbon atoms, and more preferably 1 to 24 carbon atoms; and examples include a methyl group, an ethyl group, a propyl group, an isopropyl group, a butyl group, a t-butyl group, a pentyl group, a hexyl group, a heptyl group, an octyl group, a 2-ethylhexyl group, a dodecyl group, a hexadecyl group, a cyclopropyl group, a cyclopentyl group, a cyclohexyl group, a 1-norbornyl group, and a 1-adamantyl group), an alkenyl group (preferably, an alkenyl group having 2 to 48 carbon atoms, and more preferably 2 to 18 carbon atoms; examples include a vinyl group, an allyl group, and a 3-buten-1-yl group), an aryl group (preferably, an aryl group having 6 to 48 carbon atoms, and more preferably 6 to 24 carbon atoms; examples include a phenyl group and a naphthyl group), a heterocyclic group (preferably, a heterocyclic group having 1 to 32 carbon atoms, and more preferably 1 to 18 carbon atoms; examples include a 2-thienyl group, a 4-pyridyl group, a 2-furyl group, a 2-pyrimidinyl group, a 1-pyridyl group, a 2-benzothiazolyl group, a 1-imidazolyl group, a 1-pyrazolyl group, and a benzotriazol-1-yl group), a silyl group (preferably a silyl group having 3 to 38 carbon atoms, and more preferably 3 to 18 carbon atoms; examples include a trimethylsilyl group, a triethylsilyl group, a tributylsilyl group, a t-butyldimethylsilyl group, and a t-hexyldimethylsilyl group), a hydroxyl group, a cyano group, a nitro group, an alkoxy group (preferably, an alkoxy group having 1 to 48 carbon atoms, and more preferably 1 to 24 carbon atoms (examples include a methoxy group, an ethoxy group, a 1-butoxy group, a 2-butoxy group, an isopropoxy group, a t-butoxy group, and a dodecyloxy group) or a cycloalkyloxy group (examples include a cyclopentyloxy group and a cyclohexyloxy group)), an aryloxy group (preferably, an aryloxy group having 6 to 48 carbon atoms, and more preferably 6 to 24 carbon atoms; examples include a phenoxy group and a 1-naphthoxy group), a heterocyclic oxy group (preferably, a heterocyclic oxy group having 1 to 32 carbon atoms, and more preferably 1 to 18 carbon atoms; examples include a 1-phenyltetrazole-5-oxy group, and a 2-tetrahydropyranyloxy group), a silyloxy group (preferably, a silyloxy group having 1 to 32 carbon atoms, and more preferably 1 to 18 carbon atoms; examples include a trimethylsilyloxy group, a t-butyldimethylsilyloxy group, and a diphenylmethylsilyloxy group), an acyloxy group (preferably, an acyloxy group having 2 to 48 carbon atoms, and more preferably 2 to 24 carbon atoms; examples include an acetoxy group, a pivaloyloxy group, a benzoyloxy group, and a dodecanoyloxy group), an alkoxycarbonyloxy group (preferably, an alkoxycarbonyloxy group having 2 to 48 carbon atoms, and more preferably 2 to 24 carbon atoms (examples include an ethoxycarbonyloxy group and a t-butoxycarbonyloxy group) or a cycloalkyloxycarbonyloxy group (examples include a cyclohexyloxycarbonyloxy group)), an aryloxycarbonyloxy group (preferably, an aryloxycarbonyloxy group having 7 to 32 carbon atoms, and more preferably 7 to 24 carbon atoms; examples include a phenoxycarbonyloxy group), a carbamoyloxy group (preferably, a carbamoyloxy group having 1 to 48 carbon atoms, and more preferably 1 to 24 carbon atoms; examples include an N,N-dimethylcarbamoyloxy group, an N-butylcarbamoyloxy group, an N-phenylcarbamoyloxy group, and an N-ethyl-N-phenylcarbamoyloxy group), a sulfamoyloxy group (preferably, a sulfamoyloxy group having 1 to 32 carbon atoms, and more preferably 1 to 24 carbon atoms; examples include an N,N-diethylsulfamoyloxy group and an N-propylsulfamoyloxy group), an alkylsulfonyloxy group (preferably, an alkylsulfonyloxy group having 1 to 38 carbon atoms, and more preferably 1 to 24 carbon atoms; examples include a methylsulfonyloxy group, a hexadecylsulfonyloxy group, and a cyclohexylsulfonyloxy group), an arylsulfonyloxy group (preferably, an arylsulfonyloxy group having 6 to 32 carbon atoms, and more preferably 6 to 24 carbon atoms; examples include a phenylsulfonyloxy group), an acyl group (preferably, an acyl group having 1 to 48 carbon atoms, and more preferably 1 to 24 carbon atoms; examples include a formyl group, an acetyl group, a pivaloyl group, a benzoyl group, a tetradecanoyl group, and a cyclohexanoyl group), an alkoxycarbonyl group (preferably, an alkoxycarbonyl group having 2 to 48 carbon atoms, and more preferably 2 to 24 carbon atoms; examples include a methoxycarbonyl group, an ethoxycarbonyl group, an octadecyloxycarbonyl group, a cyclohexyloxycarbonyl group, and a 2,6-di-tert-butyl-4-methylcyclohexyloxycarbonyl group), an aryloxycarbonyl group (preferably, an aryloxycarbonyl group having 7 to 32 carbon atoms, and more preferably 7 to 24 carbon atoms; examples include a phenoxycarbonyl group), a carbamoyl group (preferably, a carbamoyl group having 1 to 48 carbon atoms, and more preferably 1 to 24 carbon atoms; examples include a carbamoyl group, an N,N-diethylcarbamoyl group, an N-ethyl-N-octylcarbamoyl group, an N,N-dibutylcarbamoyl group, an N-propylcarbamoyl group, an N-phenylcarbamoyl group, an N-methyl-N-phenylcarbamoyl group, and an N,N-dicyclohexylcarbamoyl group), an amino group (preferably, an amino group having 32 or fewer carbon atoms, and more preferably 24 or fewer carbon atoms; examples include an amino group, a methylamino group, an N,N-diethylamino group, a tetradecylamino group, a 2-ethylhexylamino group, and a cyclohexylamino group), an anilino group (preferably, an anilino group having 6 to 32 carbon atoms, and more preferably 6 to 24 carbon atoms; examples include an anilino group and an N-methylanilino group), a heterocyclic amino group (preferably, a heterocyclic amino group having 1 to 32 carbon atoms, and more preferably 1 to 18 carbon atoms; examples include a 4-pyridylamino group), a carbonamide group (preferably, a carbonamide group having 2 to 48 carbon atoms, and more preferably 2 to 24 carbon atoms; examples include an acetamide group, a benzamide group, a tetradecaneamide group, a pivaloylamide group, and a cyclohexanamide group), a ureido group (preferably, a ureido group having 1 to 32 carbon atoms, and more preferably 1 to 24 carbon atoms; examples include a ureido group, an N,N-dimethylureido group, and an N-phenylureido group), an imide group (preferably, an imide group having 36 or fewer carbon atoms, and more preferably 24 or fewer carbon atoms; examples include an N-succinimide group and an N-phthalimide group), an alkoxycarbonylamino group (preferably, an alkoxycarbonylamino group having 2 to 48 carbon atoms, and more preferably 2 to 24 carbon atoms; examples include a methoxycarbonylamino group, an ethoxycarbonylamino group, a t-butoxycarbonylamino group, an octadecyloxycarbonylamino group, and a cyclohexyloxycarbonylamino group), an aryloxycarbonylamino group (preferably, an aryloxycarbonylamino group having 7 to 32 carbon atoms, and more preferably 7 to 24 carbon atoms; examples include a phenoxycarbonylamino group), a sulfonamide group (preferably, a sulfonamide group having 1 to 48 carbon atoms, and more preferably 1 to 24 carbon atoms; examples include a methanesulfonamide group, a butanesulfonamide group, a benzenesulfonamide group, a hexadecanesulfonamide group, and a cyclohexanesulfonamide group), a sulfamoylamino group (preferably, a sulfamoylamino group having 1 to 48 carbon atoms, and more preferably 1 to 24 carbon atoms; examples include an N,N-dipropylsulfamoylamino group and an N-ethyl-N-dodecylsulfamoylamino group), an azo group (preferably, an azo group having 1 to 32 carbon atoms, and more preferably 1 to 24 carbon atoms; examples include a phenylazo group and a 3-pyrazolylazo group), an alkylthio group (preferably, an alkylthio group having 1 to 48 carbon atoms, and more preferably 1 to 24 carbon atoms; examples include a methylthio group, an ethylthio group, an octylthio group, and a cyclohexylthio group), an arylthio group (preferably, an arylthio group having 6 to 48 carbon atoms, and more preferably 6 to 24 carbon atoms; examples include a phenylthio group), a heterocyclic thio group (preferably, a heterocyclic thio group having 1 to 32 carbon atoms, and more preferably 1 to 18 carbon atoms; examples include a 2-benzothiazolylthio group, a 2-pyridylthio group, and a 1-phenyltetrazolylthio group), an alkylsulfinyl group (preferably, an alkylsulfinyl group having 1 to 32 carbon atoms, and more preferably 1 to 24 carbon atoms; examples include a dodecanesulfinyl group), an arylsulfinyl group (preferably, an arylsulfinyl group having 6 to 32 carbon atoms, and more preferably 6 to 24 carbon atoms; examples include a phenylsulfinyl group), an alkylsulfonyl group (Preferably, an alkylsulfonyl group having 1 to 48 carbon atoms, and more preferably 1 to 24 carbon atoms; examples include a methylsulfonyl group, an ethylsulfonyl group, a propylsulfonyl group, a butylsulfonyl group, an isopropylsulfonyl group, a 2-ethylhexylsulfonyl group, a hexadecylsulfonyl group, an octylsulfonyl group, and a cyclohexylsulfonyl group), an arylsulfonyl group (preferably, an arylsulfonyl group having 6 to 48 carbon atoms, and more preferably 6 to 24 carbon atoms; examples include a phenylsulfonyl group and a 1-naphthylsulfonyl group), a sulfamoyl group (preferably, a sulfamoyl group having 32 or fewer carbon atoms, and more preferably 24 or fewer carbon atoms; examples include a sulfamoyl group, an N,N-dipropylsulfamoyl group, an N-ethyl-N-dodecylsulfamoyl group, an N-ethyl-N-phenylsulfamoyl group, and an N-cyclohexylsulfamoyl group), a sulfo group, a phosphonyl group (preferably, a phosphonyl group having 1 to 32 carbon atoms, and more preferably 1 to 24 carbon atoms; examples include a phenoxyphosphonyl group, an octyloxyphosphonyl group, and a phenylphosphonyl group), and a phosphinoylamino group (preferably, a phosphinoylamino group having 1 to 32 carbon atoms, and more preferably 1 to 24 carbon atoms; examples include a diethoxyphosphinoylamino group and a dioctyloxyphosphinoylamino group).

When the monovalent substituent represented by $R^2$ to $R^5$ in formula (I) is a group which can be further substituted, the monovalent substituent represented by $R^2$ to $R^5$ may further have a monovalent substituent described for $R^2$ to $R^5$. When the monovalent substituent represented by $R^2$ to $R^5$ has two or more monovalent substituents, the respective monovalent substituents may be identical to or different from each other.

In formula (I), $R^2$ and $R^3$, or/and $R^4$ and $R^5$ may be each independently bonded to each other to form a 5-membered, 6-membered or 7-membered ring.

The ring thus formed may be a saturated ring or an unsaturated ring. Examples of this 5-membered, 6-membered or 7-membered saturated ring, or 5-membered, 6-membered or 7-membered unsaturated ring include a pyrrole ring, a furan ring, a thiophene ring, a pyrazole ring, an imidazole ring, a triazole ring, an oxazole ring, a thiazole ring, a pyrrolidine ring, a piperidine ring, a cyclopentene ring, a cyclohexene ring, a benzene ring, a pyridine ring, a pyrazine ring, and a pyridazine ring. Preferred examples include a benzene ring and a pyridine ring.

When the 5-membered, 6-membered or 7-membered ring formed by $R^2$ and $R^3$, or/and $R^4$ and $R^5$ in formula (I) is a group which can be further substituted, the ring may further have a monovalent substituent described for $R^2$ to $R^5$, and when the 5-membered, 6-membered or 7-membered ring has two or more monovalent substituents, the respective monovalent substituents may be identical to or different from each other.

In formula (I), the substituents for $R^2$ and $R^5$ are each preferably, among the substituents described above, an alkoxycarbonyl group, an aryloxycarbonyl group, a carbamoyl group, an alkylsulfonyl group, an arylsulfonyl group, a nitrile group, an imide group, or a carbamoylsulfonyl group; more preferably an alkoxycarbonyl group, an aryloxycarbonyl group, a carbamoyl group, an alkylsulfonyl group, a nitrile group, an imide group, or a carbamoylsulfonyl group; even more preferably an alkoxycarbonyl group, an aryloxycarbonyl group, a carbamoyl group, a nitrile group, an imide group, or a carbamoylsulfonyl group; and particularly preferably an alkoxycarbonyl group, an aryloxycarbonyl group, or a carbamoyl group.

In formula (I), the substituents for $R^3$ and $R^4$ are each preferably, among the substituents described above, an alkyl group, an aryl group, or a heterocyclic group; and more preferably an alkyl group or an aryl group.

The various groups indicated in the preferred embodiment described above may be unsubstituted, or may have any of the substituents described above.

In formula (I), when $R^3$ and $R^4$ represent an alkyl group, the alkyl group is preferably a straight-chain, branched or cyclic alkyl group having 1 to 12 carbon atoms, and specific examples thereof include a methyl group, an ethyl group, an n-propyl group, an isopropyl group, a cyclopropyl group, an n-butyl group, an i-butyl group, a t-butyl group, a cyclobutyl group, a cyclopentyl group, a cyclohexyl group, and a benzyl group. The alkyl group is more preferably a branched or cyclic alkyl group having 1 to 12 carbon atoms, and specific examples thereof include an isopropyl group, a cyclopropyl group, an i-butyl group, a t-butyl group, a cyclobutyl group, a cyclopentyl group, or a cyclohexyl group. The alkyl group is even more preferably a secondary alkyl group or tertiary alkyl group having 1 to 12 carbon atoms, and more specific examples thereof include an isopropyl group, a cyclopropyl group, an i-butyl group, a t-butyl group, a cyclobutyl group, or a cyclohexyl group.

The various groups indicated in the preferred embodiment described above may be unsubstituted, or may have any of the substituents described above.

In formula (I), when $R^3$ and $R^4$ represent an aryl group, the aryl group is preferably a phenyl group or a naphthyl group, and more preferably a phenyl group.

When $R^3$ and $R^4$ represent a heterocyclic group, the heterocyclic group is preferably a 2-thienyl group, a 4-pyridyl group, a 3-pyridyl group, a 2-pyridyl group, a 2-furyl group, a 2-pyrimidinyl group, a 2-benzothiazolyl group, a 1-imidazolyl group, a 1-pyrazolyl group, or a benzotriazol-1-yl group, and more preferably a 2-thienyl group, a 4-pyridyl group, a 2-furyl group, a 2-pyrimidinyl group, or a 1-pyridyl group.

The various groups indicated in the preferred embodiment described above may be unsubstituted, or may have any of the substituents described above.

In formula (I), $R^7$ represents a hydrogen atom, a halogen atom, an alkyl group, an aryl group, or a heterocyclic group.

When $R^7$ is not a hydrogen atom, that is, when $R^7$ is a halogen atom, an alkyl group, an aryl group, or a heterocyclic group, $R^7$ represents a group that is the same as the halogen atom, alkyl group, aryl group or heterocyclic group described as the substituents represented by $R^2$ to $R^5$, and the preferable range thereof is also the same as the preferable range of the halogen atom, alkyl group, aryl group or heterocyclic group described as the substituents represented by $R^2$ to $R^5$.

When the alkyl group, aryl group or heterocyclic group represented by $R^7$ in formula (I) is a group which can be further substituted, the group may be substituted with the substituents described above as the monovalent substituent represented by $R^2$ to $R^5$. When the alkyl group, aryl group or heterocyclic group represented by $R^7$ is substituted with two or more substituents, those substituents may be identical to or different from each other.

Ma in formula (I) represents a metal or a metal compound. Ma may be any of a metal atom or a metal compound capable of forming a metal complex, and examples thereof include a divalent metal atom, a divalent metal oxide, a divalent metal hydroxide, or a divalent metal chloride.

Examples of the metal include Zn, Mg, Si, Sn, Rh, Pt, Pd, Mo, Mn, Pb, Cu, Ni, Co, Fe, and B.

Examples of the metal compound include metal chlorides such as AlCl, InCl, FeCl, $TiCl_2$, $SnCl_2$, $SiCl_2$, and $GeCl_2$; metal oxides such as TiO and VO; and metal hydroxides such as $Si(OH)_2$.

Among these, from the viewpoints of the stability, spectroscopic characteristics, heat resistance, light resistance, production suitability and the like of the complex, Ma in formula (I) is preferably Fe, Zn, Mg, Si, Pt, Pd, Mo, Mn, Cu, Ni, Co, TiO, B or VO; more preferably Fe, Zn, Mg, Si, Pt, Pd, Cu, Ni, Co, B or VO; and most preferably Fe, Zn, Cu, Co, B or VO (V=O). Among these, particularly Zn is preferred.

In formula (I), $X^3$ and $X^4$ each independently represent NR, a nitrogen atom, an oxygen atom, or a sulfur atom.

R represents a hydrogen atom, an alkyl group (preferably, a straight-chain, branched or cyclic alkyl group having 1 to 36 carbon atoms, and more preferably 1 to 12 carbon atoms; examples include a methyl group, an ethyl group, a propyl group, an isopropyl group, a butyl group, an isobutyl group, a t-butyl group, a hexyl group, a 2-ethylhexyl group, a dodecyl group, a cyclopropyl group, a cyclopentyl group, a cyclohexyl group, and a 1-adamantyl group), an alkenyl group (preferably, an alkenyl group having 2 to 24 carbon atoms, and more preferably 2 to 12 carbon atoms; examples include a vinyl group, an allyl group, and a 3-buten-1-yl group), an aryl group (preferably, an aryl group having 6 to 36 carbon atoms, and more preferably 6 to 18 carbon atoms; examples include a phenyl group and a naphthyl group), a heterocyclic group (preferably, a heterocyclic group having 1 to 24 carbon atoms, and more preferably 1 to 12 carbon atoms; examples include a 2-thienyl group, a 4-pyridyl group, a 2-furyl group, a 2-pyrimidinyl group, a 1-pyridyl group, a 2-benzothiazolyl group, a 1-imidazolyl group, a 1-pyrazolyl group, and a benzotriazol-1-yl group), an acyl group (preferably, an acyl group having 1 to 24 carbon atoms, and more preferably 2 to 18 carbon atoms; examples include an acetyl group, a pivaloyl group, a 2-ethylhexyl group, a benzoyl group, and a cyclohexanoyl group), an alkylsulfonyl group (preferably, an alkylsulfonyl group having 1 to 24 carbon atoms, and more preferably 1 to 18 carbon atoms; examples include a methylsulfonyl group, an ethylsulfonyl group, an isopropylsulfonyl group, and a cyclohexylsulfonyl group), or an arylsulfonyl group (preferably, an arylsulfonyl group having 6 to 24 carbon atoms, and more preferably 6 to 18 carbon atoms; and examples include a phenylsulfonyl group, and a naphthylsulfonyl group).

Furthermore, when R can be further substituted, R may be further substituted with a substituent, and when R is substituted with plural substituents, those substituents may be identical to or different from each other.

$X^3$ and $X^4$ are preferably each independently an oxygen atom or a sulfur atom, and particularly preferably, $X^3$ and $X^4$ each are an oxygen atom.

In formula (I), $X^5$ represents a group required to neutralize the charge of Ma, and examples thereof include a halogen atom, a hydroxyl group, a carboxylic acid group, a phosphoric acid group, a sulfonic acid group, R—CONHCO—R(R's each independently represent an alkyl group, an aryl group, or a heterocyclic group), and R—CONHSO$_2$—R(R's each independently represent an alkyl group, an aryl group or a heterocyclic group). Among these, from the viewpoint of production, a halogen atom, a hydroxyl group, a carboxylic acid group, a sulfonic acid group, R—CONHCO—R, or R—CONHSO$_2$—R is preferred, and a hydroxyl group, a carboxylic acid group, or R—CONHCO—R is more preferred.

a represents 1 or 2.

In formula (I), $R^8$ to $R^{17}$ each independently represent a hydrogen atom or a monovalent substituent. When two or more among $R^8$ to $R^{17}$ represent monovalent substituents, those may be identical to or different from each other. Examples of the monovalent substituent represented by $R^8$ to $R^{17}$ include the groups mentioned as examples of the monovalent substituent represented by $R^2$ to $R^5$. The monovalent substituent represented by $R^8$ to $R^{17}$ may be further substituted with any of the groups described as substituents for $R^2$ to $R^5$, and when the monovalent substituent is substituted with plural substituents, those substituents may be identical to or different from each other.

In formula (I), at least one of $R^8$ to $R^{17}$ represents a substituent represented by formula (II).

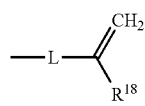

Formula (II)

In formula (II), $R^{18}$ represents a hydrogen atom or a methyl group.

In formula (II), L represents a single bond or a divalent linking group. The divalent linking group is, for example, preferably an alkylene group, an aralkylene group, an arylene group, or a divalent heterocyclic group, or a divalent linking group formed to include a group selected from the group consisting of an alkylene group, an aralkylene group, an arylene group and a divalent heterocyclic group, and a group selected from the group consisting of —O—, —S—, —CO—, —SO$_2$—, —N(Rb)—, —COO—, —OCO—, —CON(Rc)-, —N(Rc)CO—, —N(Rc)COO—, —OOCN (Rc)-, —N(Rc)CON(Rd)-, —SO$_2$N(Rc)- and —N(Rc) SO$_2$—.

The divalent linking group is more preferably an alkylene group, an aralkylene group or an arylene group, or a divalent linking group formed to include a group selected from the group consisting of an alkylene group, an aralkylene group and an arylene group, and a group selected from the group consisting of —O—, —S—, —CO—, —SO$_2$—, —N(Rb)—, —COO—, —OCO—, —CON(Rc)- and —N(Rc)CO—.

The alkylene group in the case where L represents an alkylene group is preferably a straight-chain, branched or cyclic alkylene group having 1 to 18 carbon atoms, and more preferably 1 to 12 carbon atoms, and examples thereof include methylene, ethylene, propylene, butylene, cyclopropylene, cyclobutylene, and cyclohexylene.

The aralkylene group in the case where L represents an aralkylene group is preferably an aralkylene group having 7 to 18 carbon atoms, and more preferably 7 to 16 carbon atoms, and examples thereof include benzylene and phenethylene.

The arylene group in the case where L represents an arylene group is preferably an arylene group having 6 to 18 carbon atoms, and more preferably 6 to 12 carbon atoms, and examples thereof include o-phenylene, m-phenylene, p-phenylene, and 1,4-naphthylene.

Examples of the heterocyclic ring that is contained in the divalent heterocyclic group in the case where L represents a divalent heterocyclic group, include a pyridine ring, a pyrrole ring, a thiophene ring, and a furan ring.

When L represents an alkylene group, an aralkylene group, an arylene group or a divalent heterocyclic group, and those groups can be further substituted, L may be substituted with any of the groups described as the substituents for $R^2$ to $R^5$, and when L is substituted with two or more substituents, those substituents may be identical to or different from each other.

L may also be a divalent group that is formed by combining two or more divalent groups selected from the group consisting of an alkylene group, an aralkylene group, an arylene group, a divalent heterocyclic group, —O—, —S—, —CO—, —SO$_2$—, —N(Rb)—, —COO—, —OCO—, —CON(Rc)-, —N(Rc)CO—, —N(Rc)COO—, —OOCN (Rc)-, —N(Rc)CON(Rd)-, —SO$_2$N(Rc)- and —N(Rc) SO$_2$—.

Rb, Rc and Rd each independently represent a hydrogen atom or a monovalent substituent.

Examples of the monovalent substituent represented by Rb include an alkyl group, an alkenyl group, an aryl group, a heterocyclic group, an acyl group, an alkylsulfonyl group, and an arylsulfonyl group, and those groups have the same definitions as the alkyl group, alkenyl group, aryl group, heterocyclic group, acyl group, alkylsulfonyl group and arylsulfonyl group described as the substituents for $R^2$ to $R^5$, while the groups also have the same preferred ranges as those described as the substituents for $R^2$ to $R^5$.

When the alkyl group, alkenyl group, aryl group, heterocyclic group, acyl group, alkylsulfonyl group or arylsulfonyl group represented by Rb is a group that can be further substituted, those groups may be substituted with any of the groups described as the substituents for $R^2$ to $R^5$, and when those groups are substituted with two or more substituents, those substituents may be identical to or different from each other.

Examples of the monovalent substituent represented by Rc include an alkyl group, an alkenyl group, an aryl group, and a heterocyclic group, and those groups have the same definitions as the alkyl group, alkenyl group, aryl group and heterocyclic group described as the substituents for $R^2$ to $R^5$, while the groups also have the same preferred ranges as those described as the substituents for $R^2$ to $R^5$.

When the alkyl group, alkenyl group, aryl group or heterocyclic group represented by Rc is a group that can be further substituted, those groups may be substituted with any of the groups described as the substituents for $R^2$ to $R^5$, and when those groups are substituted with two or more substituents, those substituents may be identical to or different from each other.

Examples of the monovalent substituent represented by Rd include an alkyl group, an alkenyl group, an aryl group, and a heterocyclic group, and those groups have the same definitions as the alkyl group, alkenyl group, aryl group and heterocyclic group described as the substituents for $R^2$ to $R^5$, while the groups also have the same preferred ranges as those described as the substituents for $R^2$ to $R^5$.

When the alkyl group, alkenyl group, aryl group or heterocyclic group represented by Rd is a group that can be further substituted, those groups may be substituted with any of the groups described as the substituents for $R^2$ to $R^5$, and when those groups are substituted with two or more substituents, those substituents may be identical to or different from each other.

Regarding the number of substitutions of the substituent represented by formula (II), from the viewpoint that the compound represented by formula (I) is immobilized by larger number of covalent bonds with a monomer and another polymerizable compound, it is preferable that the compound represented by formula (I) have two or more substituents represented by formula (II).

Regarding the position of substitution of the substituent represented by formula (II), from the viewpoint of the ease of synthesis or the like, it is preferable that at least any one of $R^8$ to $R^{12}$ in formula (I) is a substituent represented by formula (II), and at least any one of $R^{13}$ to $R^{17}$ is a substituent represented by formula (II). More preferably, the mode of substitution for $R^8$ to $R^{12}$ and $R^{13}$ to $R^{17}$ is symmetric.

Being symmetrical in the present specification means that in formula (I), the substituents represented by $R^8$, $R^9$, $R^{10}$, $R^{11}$ and $R^{12}$ are respectively identical to the substituents represented by $R^{13}$, $R^{14}$, $R^{15}$, $R^{16}$ and $R^{17}$ (or $R^{17}$, $R^{16}$, $R^{15}$, $R^{14}$ and $R^{13}$).

A preferred embodiment of the compound represented by formula (I) is described below.

That is, in a preferred embodiment, $R^2$ and $R^5$ each independently represent a hydrogen atom, a halogen atom, an alkyl group, an alkenyl group, an aryl group, a heterocyclic group, a hydroxyl group, a cyano group, a nitro group, an alkoxy group, an aryloxy group, a heterocyclic oxy group, an acyl group, an alkoxycarbonyl group, an aryloxycarbonyl group, a carbamoyl group, an imide group, an alkoxycarbonylamino group, a sulfonamide group, an azo group, an alkylthio group, an arylthio group, a heterocyclic thio group, an alkylsulfonyl group, an arylsulfonyl group, or a sulfamoyl group;

$R^3$ and $R^4$ each independently represent a hydrogen atom, a halogen atom, an alkyl group, an alkenyl group, an aryl group, a heterocyclic group, a silyl group, a hydroxyl group, a cyano group, an alkoxy group, an aryloxy group, a heterocyclic oxy group, an acyl group, an alkoxycarbonyl group, a carbamoyl group, an anilino group, a carbonamide group, a ureido group, an imide group, an alkoxycarbonylamino group, a sulfonamide group, an azo group, an alkylthio group, an arylthio group, a heterocyclic thio group, an alkylsulfonyl group, an arylsulfonyl group, a sulfamoyl group, or a phosphinoylamino group;

$R^7$ represents a hydrogen atom, a halogen atom, an alkyl group, an aryl group, or a heterocyclic group; Ma represents Zn, Mg, Si, Pt, Pd, Mo, Mn, Cu, Ni, Co, TiO, B or VO;

$X^3$ and $X^4$ each independently represent NR (wherein R represents a hydrogen atom, an alkyl group, or a heterocyclic group) or an oxygen atom; $X^5$ represents a group which is bonded via an oxygen atom or a nitrogen atom; a represents 0 or 1; and $R^8$ to $R^{17}$ each independently represent a hydrogen atom, a halogen atom, an alkyl group, an aryl group, a heterocyclic group, a hydroxyl group, a cyano group, a nitro group, an alkoxy group, an aryloxy group, a heterocyclic oxy group, an acyl group, an alkoxycarbonyl group, an aryloxycarbonyl group, a carbamoyl group, an imide group, an alkoxycarbonylamino group, a sulfonamide group, an azo group, an alkylthio group, an arylthio group, a heterocyclic thio group, an alkylsulfonyl group, an arylsulfonyl group, or a sulfamoyl group.

A preferred embodiment of the substituent represented by formula (II) that is contained in formula (I) is described below.

Examples of the preferred embodiment of the substituent represented by formula (II) include an embodiment in which L represents a single bond or a divalent linking group, and the divalent linking group is an alkylene group, an aralkylene group, an arylene group, or a divalent heterocyclic group, or the divalent linking group is a divalent linking group formed to include a group selected from the group consisting of an alkylene group, an aralkylene group, an arylene group and a divalent heterocyclic group, and a group selected from the group consisting of —O—, —S—, —CO—, —SO$_2$—, —N(Rb)-, —COO—, —OCO—, —CON(Rc)-, —N(Rc)CO—, —N(Rc) COO—, —OOCN(Rc)-, —N(Rc)CON(Rd)-, —SO$_2$N(Rc)- and —N(Rc)SO$_2$—.

Furthermore, regarding the preferred position of substitution of the substituent represented by formula (II) contained in formula (I), there may be mentioned an embodiment in which at least any one of $R^8$ to $R^{12}$ in formula (I) is a substituent represented by formula (II), and at least any one of $R^{13}$ to $R^{17}$ is a substituent represented by formula (II), while the mode of substitution for $R^8$ to $R^{12}$ and $R^{13}$ to $R^{17}$ is symmetric.

A more preferred embodiment of the compound represented by formula (I) is described below.

That is, examples of the more preferred embodiment of the compound represented by formula (I) include an embodiment in which $R^2$ and $R^5$ each independently represent an alkyl group, an alkenyl group, an aryl group, a heterocyclic group, a cyano group, a nitro group, an acyl group, an alkoxycarbonyl group, an aryloxycarbonyl group, a carbamoyl group, an imide group, an alkylsulfonyl group, an arylsulfonyl group, or a sulfamoyl group;

$R^3$ and $R^4$ each independently represent a hydrogen atom, an alkyl group, an alkenyl group, an aryl group, a heterocyclic group, a cyano group, an acyl group, an alkoxycarbonyl group, a carbamoyl group, a carbonamide group, a ureido group, an imide group, an alkoxycarbonylamino group, a sulfonamide group, an alkylthio group, an arylthio group, a heterocyclic thio group, an alkylsulfonyl group, an arylsulfonyl group, or a sulfamoyl group;

$R^7$ represents a hydrogen atom, a halogen atom, an alkyl group, an aryl group, or a heterocyclic group; Ma represents Zn, Mg, Si, Pt, Pd, Cu, Ni, Co, B or VO; $X^3$ and $X^4$ are oxygen atoms; $X^5$ represents a group which is bonded via an oxygen atom or a nitrogen atom;

a represents 0 or 1; and $R^8$ to $R^{17}$ each independently represent an alkyl group, an alkenyl group, an aryl group, a heterocyclic group, a cyano group, a nitro group, an acyl group, an alkoxycarbonyl group, an aryloxycarbonyl group, a carbamoyl group, an imide group, an alkylsulfonyl group, an arylsulfonyl group, or a sulfamoyl group.

A more preferred embodiment of the substituent represented by formula (II) contained in formula (I) is described below.

Examples of the more preferred embodiment of the substituent represented by formula (II) include an embodiment in which L represents a single bond or a divalent linking group; and the divalent linking group is an alkylene group, an aralkylene group or an arylene group, or a divalent linking group formed to include a group selected from the group consisting of an alkylene group, an aralkylene group and an arylene group, and a group selected from the group consisting of —O—, —S—, —CO—, —SO2-, —N(Rb)—, —COO—, —OCO—, —CON(Rc)- and —N(Rc)CO—.

Regarding a more preferred position of substitution of the substituent represented by formula (II) contained in formula (I), there may be mentioned an embodiment in which at least any one of $R^8$ to $R^{12}$ in formula (I) is a substituent represented by formula (II), and at least any one of $R^{13}$ and $R^{17}$ is a substituent represented by formula (II), while the mode of substitution for $R^8$ to $R^{12}$ and $R^{13}$ to $R^{17}$ is symmetric.

The compound represented by formula (I) may be a tautomer.

The tautomer according to the invention may be any compound having a structure which can be formed as result of the movement of one hydrogen atom in the molecule, and for example, may have a structure of any one of formula (a) to formula (f) described below.

Formula (a)

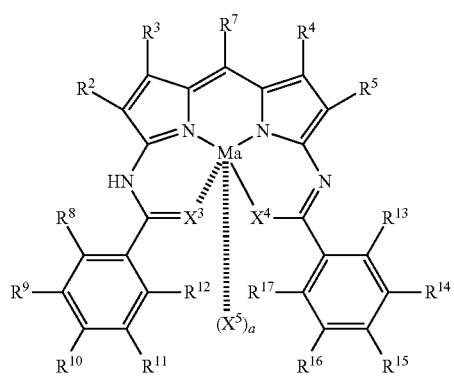

Formula (b)

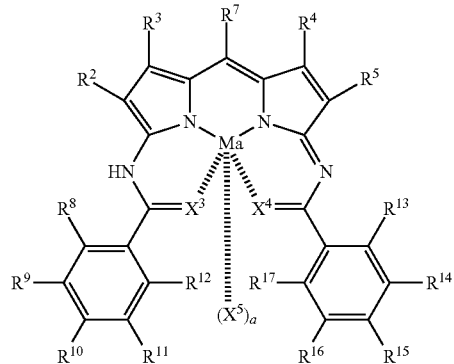

Formula (c)

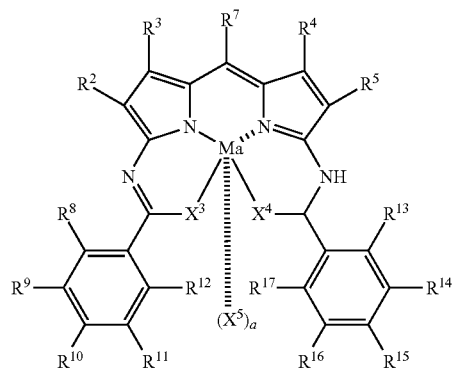

Formula (d)

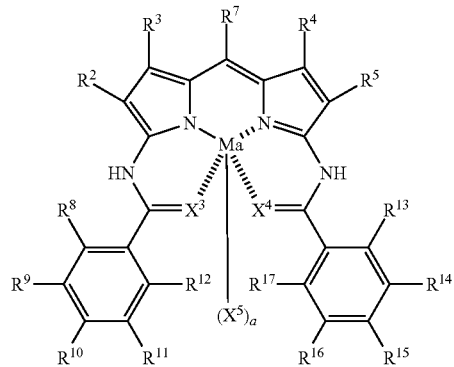

Formula (e)

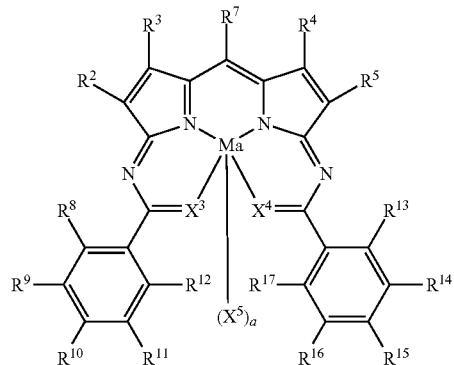

Formula (f)

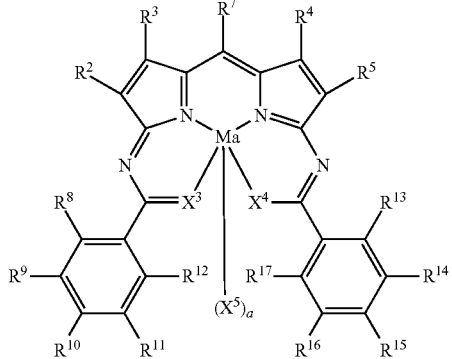

Formula (h)

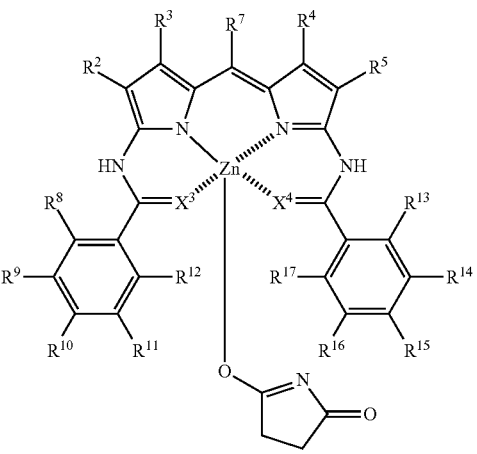

The structures described above are examples of the tautomeric structures, and various isomeric structures can be obtained depending on the structures of $R^2$ to $R^5$, $R^7$ to $R^{17}$, and $X^3$ to $X^5$.

Here, $R^2$ to $R^5$, $R^7$ to $R^{17}$, $X^3$ to $X^5$, Ma and a in formula (a) to formula (f) have the same definitions as $R^2$ to $R^5$, $R^7$ to $R^{17}$, $X^3$ to $X^5$, Ma and a indicated in formula (I), respectively.

For example, when the "group capable of bonding with Ma" for $X^5$ is a monovalent group derived from succinic acid imide, further two kinds of isomeric structures may be considered.

Formula (g)

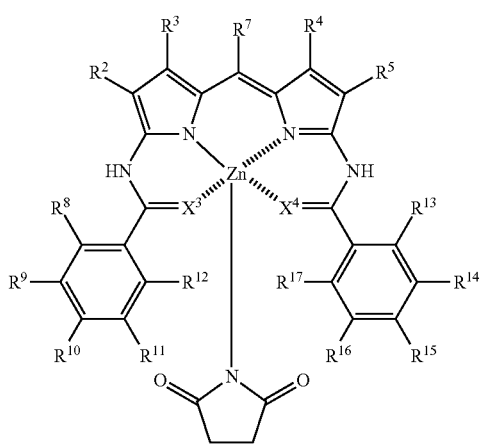

$R^2$ to $R^5$, $R^7$ to $R^{17}$, and $X^3$ to $X^4$ in formula (g) and formula (h) have the same definitions as $R^2$ to $R^5$, $R^7$ to $R^{17}$, and $X^3$ to $X^4$ in formula (I), respectively.

The content of the compound represented by formula (I) or a tautomer thereof in a colored composition according to the invention may vary with the molecular weight and the extinction coefficient of the compound, but the content is preferably, on a mass basis, 0.1% to 30% by mass, and more preferably 0.5% to 20% by mass, relative to the total solid content of the colored composition.

When the content of the compound represented by formula (I) or a tautomer thereof is in the range described above, it is advantageous from the viewpoint that a good color density (for example, a color density suitable for liquid crystal display) is obtained, and satisfactory patterning of the pixels is obtained.

The molar extinction coefficient of the dipyrromethene-metal complex compound or a tautomer thereof according to the invention is preferably as high as possible, from the viewpoint of the film thickness. Also, the maximum absorption wavelength, λmax, is preferably 520 nm to 580 nm, and more preferably 530 nm to 570 nm, from the viewpoint of an enhancement of color purity. Meanwhile, the maximum absorption wavelength and the molar extinction coefficient are measured using a spectrophotometer, UV-1800PC (manufactured by Shimadzu Corp.).

Next, specific examples of the dipyrromethene-metal complex compound according to the invention will be described below. However, the dipyrromethene-metal complex compound is not limited to these.

The following specific examples A-1 to A-16 represent compounds in which the mode of substitution is symmetric. Here, when it is said to be symmetric, it is implied that in the compound formulas described below, the substituents represented by $R^8$, $R^9$, $R^{10}$, $R^{11}$ and $R^{12}$ are the same as the substituents represented by $R^{13}$, $R^{14}$, $R^{15}$, $R^{16}$ and $R^{17}$ (or $R^{17}$, $R^{16}$, $R^{15}$, $R^{14}$ and $R^{13}$), respectively. The following table indicates the cases in which the substituents represented by $R^8$, $R^9$, $R^{10}$, $R^{11}$ and $R^{12}$ are the same as the substituents represented by $R^{13}$, $R^{14}$, $R^{15}$, $R^{16}$ and $R^{17}$, respectively.

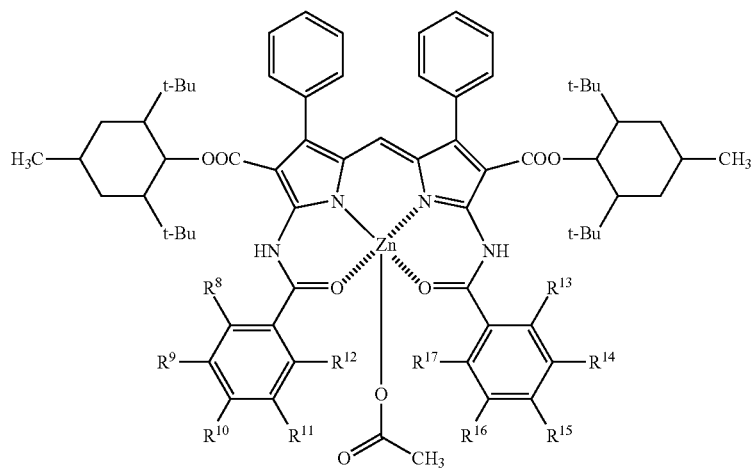
| Compound No. | $R^8 = R^{13}$ | $R^9 = R^{14}$ | $R^{10} = R^{15}$ | $R^{11} = R^{16}$ | $R^{12} = R^{17}$ |
|---|---|---|---|---|---|
| A-1 | ![CH2=C(CH3)C(=O)OCH2CH2OC(=O)CH3] | —H | —H | —H | —H |
| A-2 | ![CH2=CH–] | —H | —H | —H | —H |
| A-3 | —H | ![CH2=CH-CH2CH2CH2–] | —H | —H | —H |
| A-4 | —H | —H | ![CH2=CH-(CH2)4–] | —H | —H |
| A-5 | —H | —H | ![CH2=CH-CH2CH2-OCH3] | —H | —H |
| A-6 | ![CH2=C(CH3)C(=O)OCH2CH(OH)CH2OCH3] | —H | —OCH3 | —H | —H |
| A-7 | —H | ![CH2=CH-CH2-O-CH(OH)CH2OC(=O)CH3] | —CH3 | —H | —H |
| A-8 | ![CH2=CH-CH2-CH(CH3)OC(=O)CH3] | —H | —CH3 | —H | —H |
| A-9 | ![CH2=C(CH3)C(=O)NHCH3] | —H | —OCH3 | —H | —H |
| A-10 | —H | ![CH2=C(CH3)C(=O)NHCH3] | —H | —CH3 | —H |

-continued
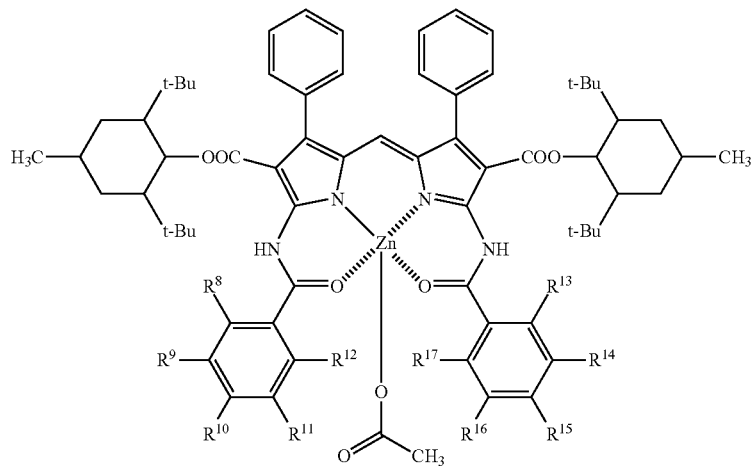
| Compound No. | $R^8 = R^{13}$ | $R^9 = R^{14}$ | $R^{10} = R^{15}$ | $R^{11} = R^{16}$ | $R^{12} = R^{17}$ |
|---|---|---|---|---|---|
| A-11 | —H | ![methoxy-hydroxy-propyl methacrylate group] | —Br | —H | —H |
| A-12 | ![p-tolyl methacrylate group] | —H | —H | —H | —H |
| A-13 | ![3-methyl-3-butenyl acetate group] | —H | ![3-methyl-3-butenyl acetate group] | —H | —H |
| A-14 | —H | ![methacryloyloxy acetate group] | ![allyl acetate group] | —H | —H |
| A-15 | —C$_2$H$_5$ | —H | ![allyl group] | —H | —C$_2$H$_5$ |
| A-16 | ![methallyl acetate group] | —H | —H | ![phenyl group] | —H |

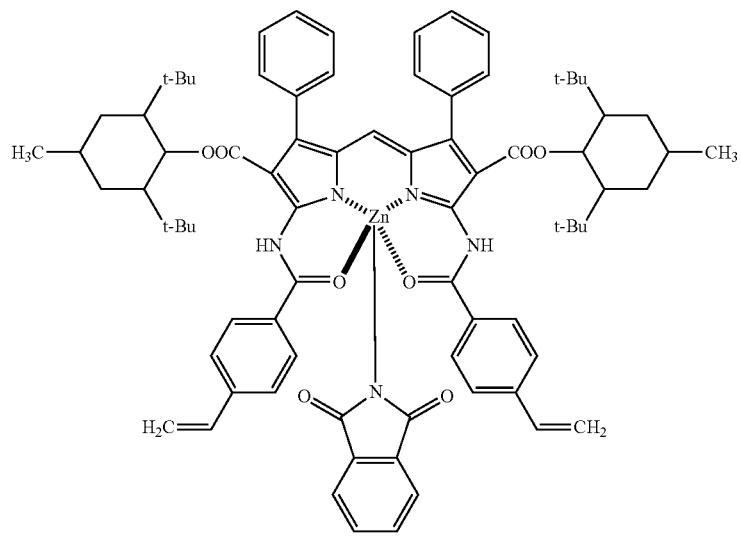
B-1
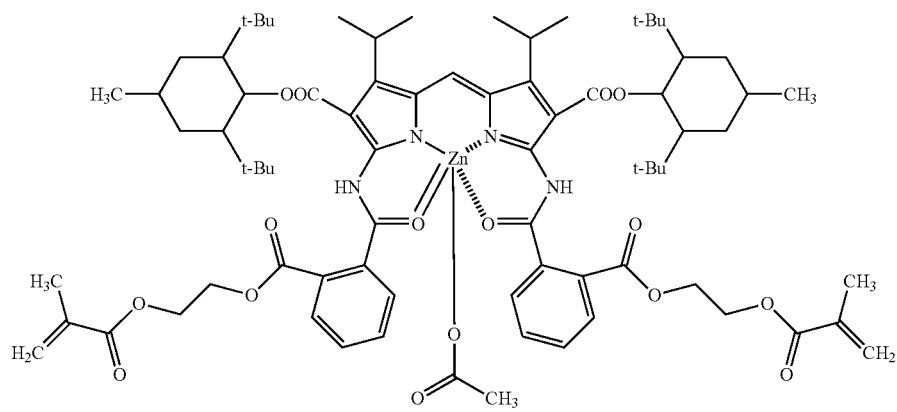
B-2
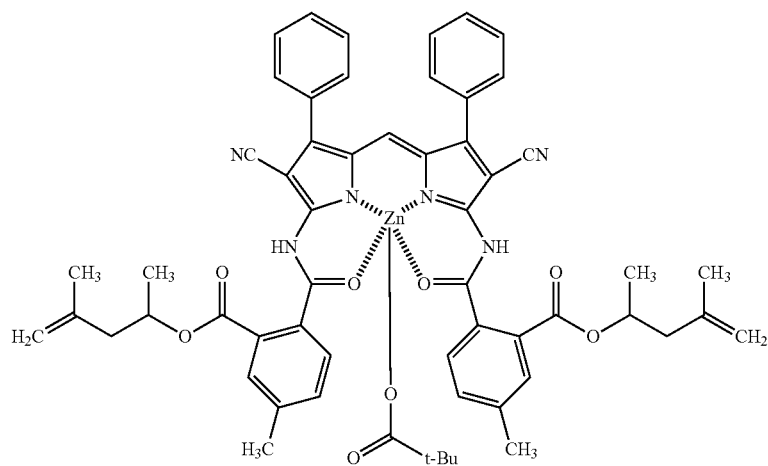
B-3

-continued
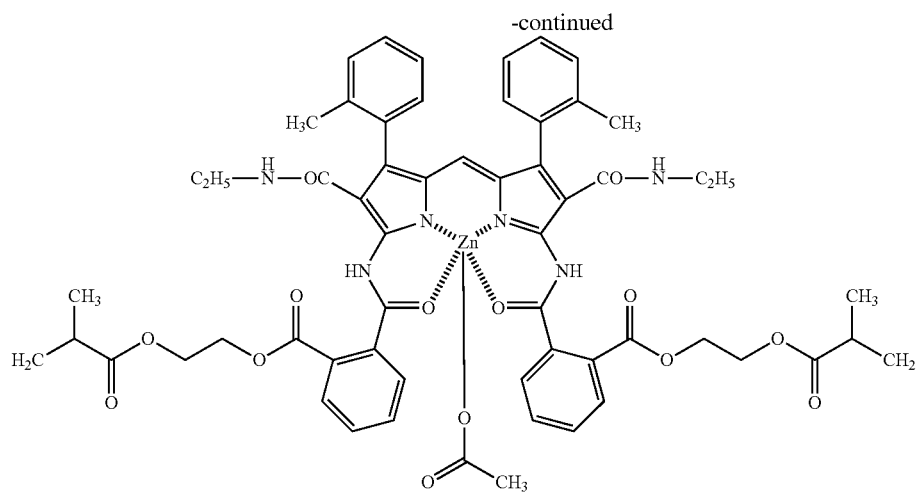
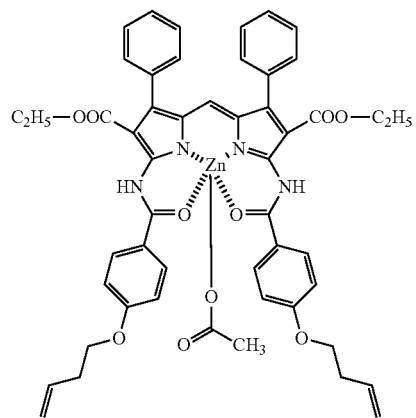
B-5
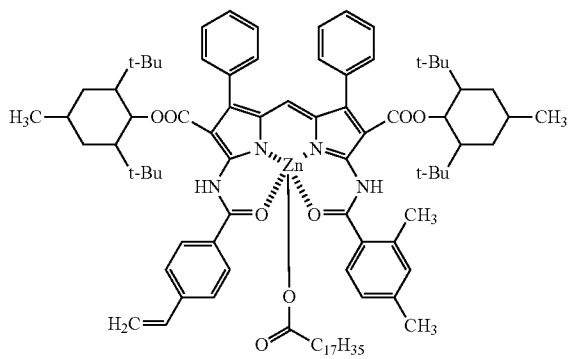
C-1
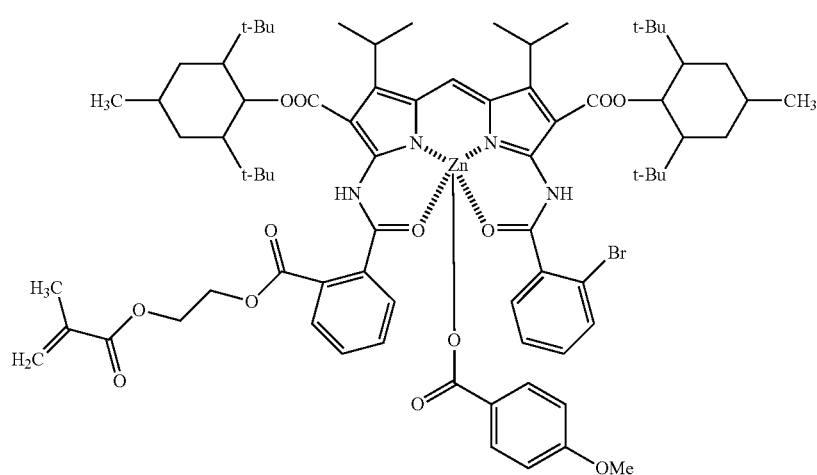
C-2

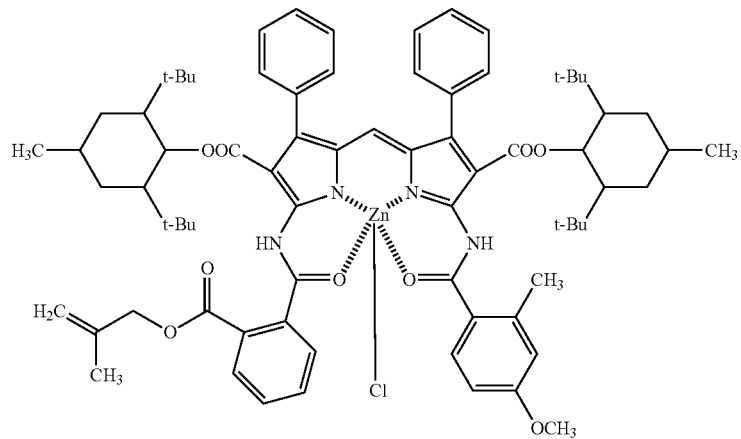
C-3
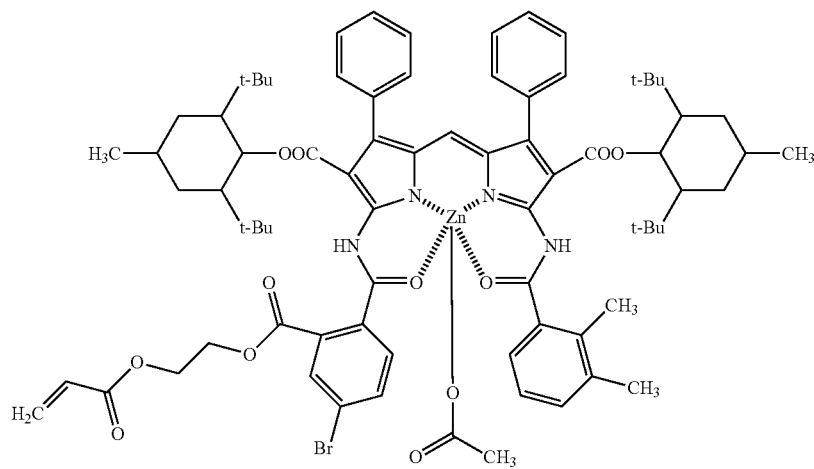
C-4
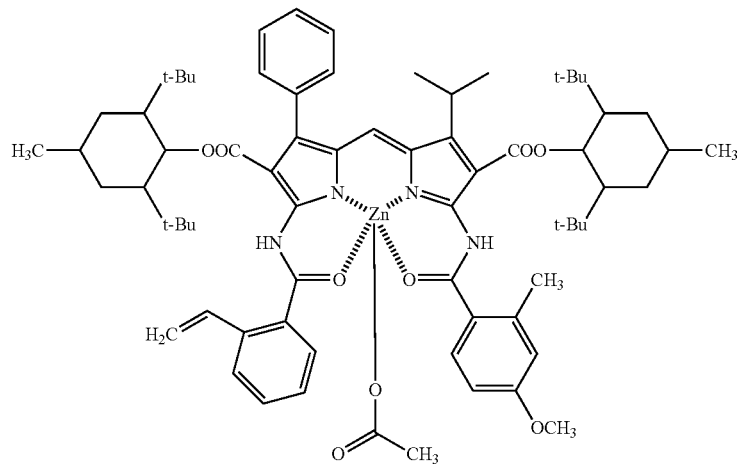
C-5

-continued
C-6
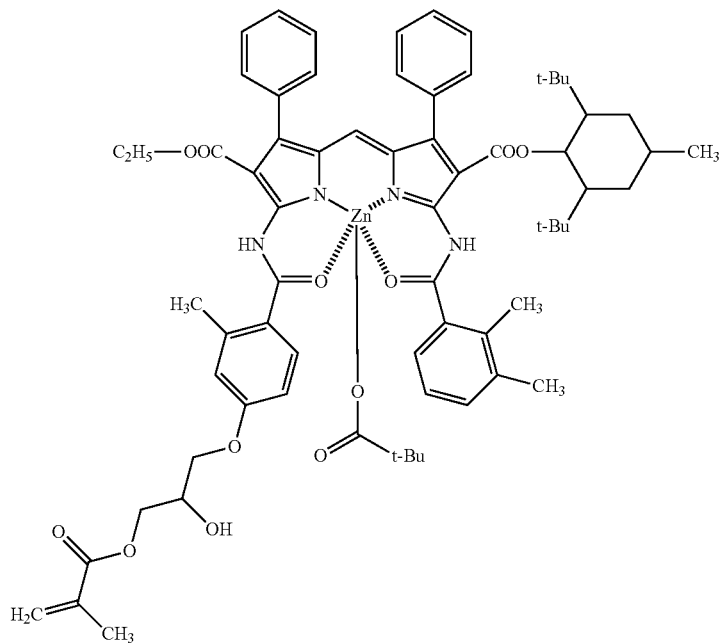
D-1
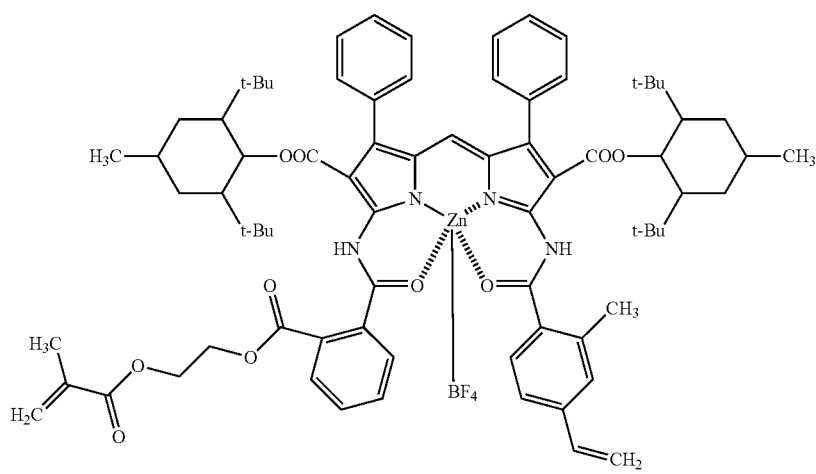
D-2
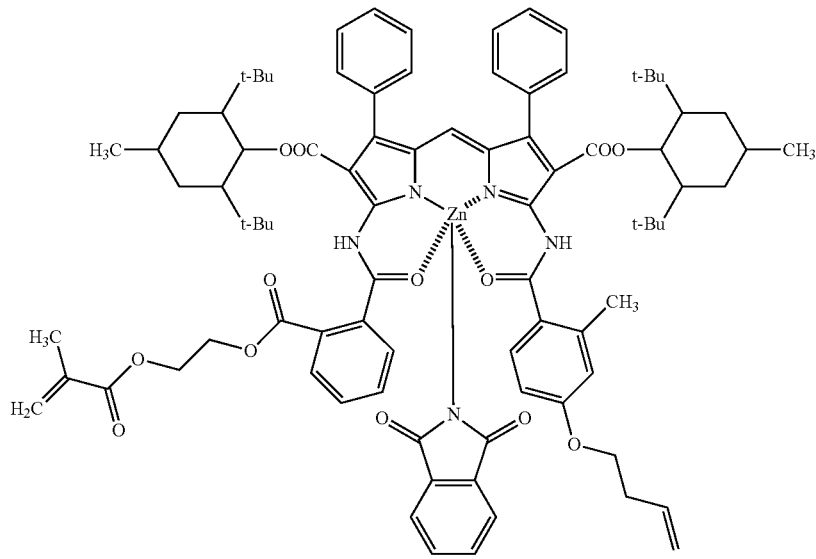

-continued
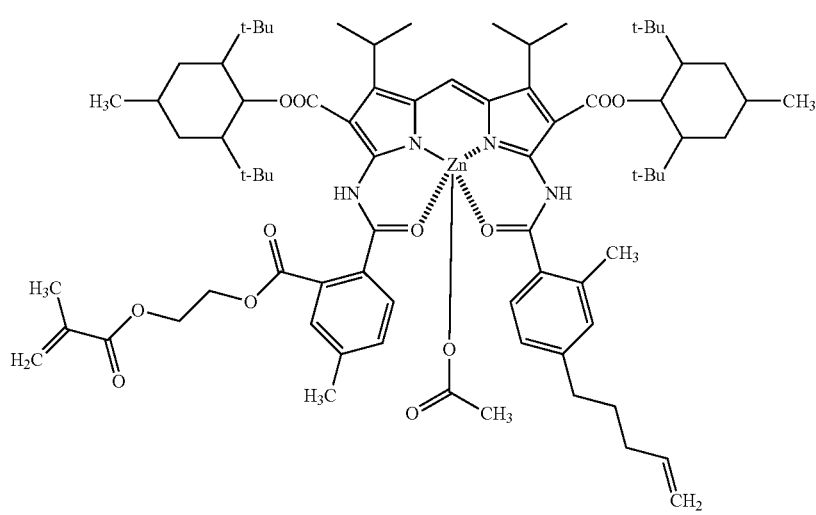
D-3
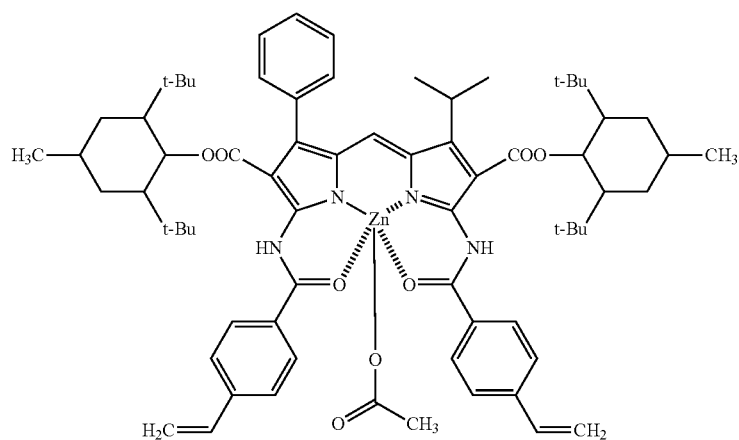
D-4
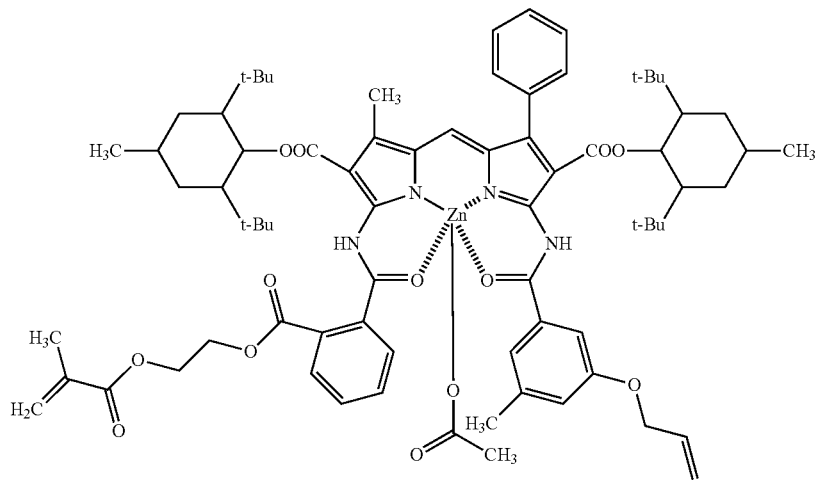
D-5

D-6
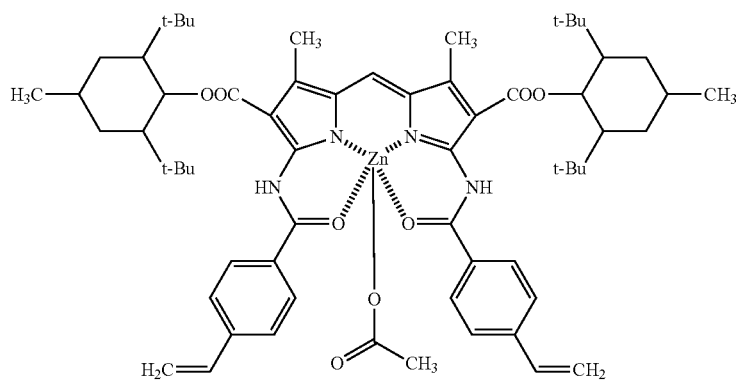
D-7
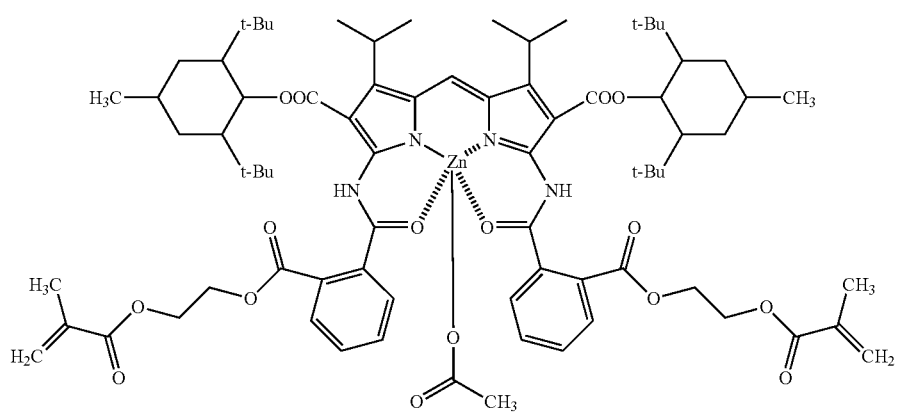
Reaction scheme A for Exemplary Compound A-1 is described below.
Reaction Scheme
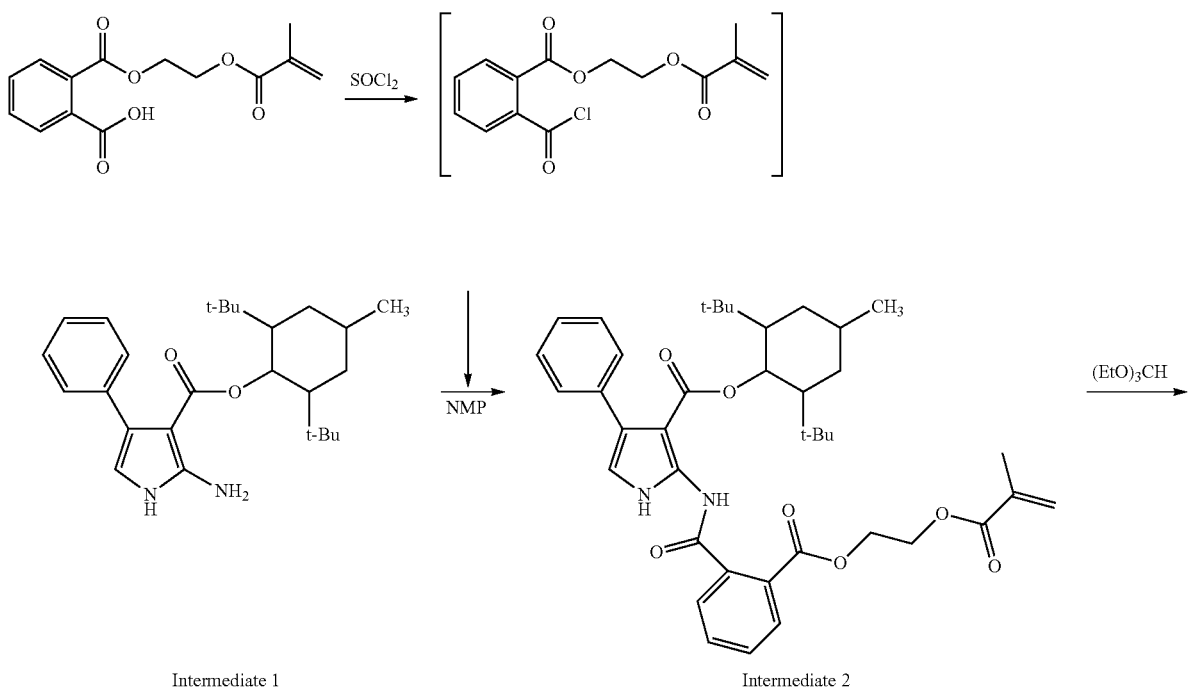
Intermediate 1
Intermediate 2

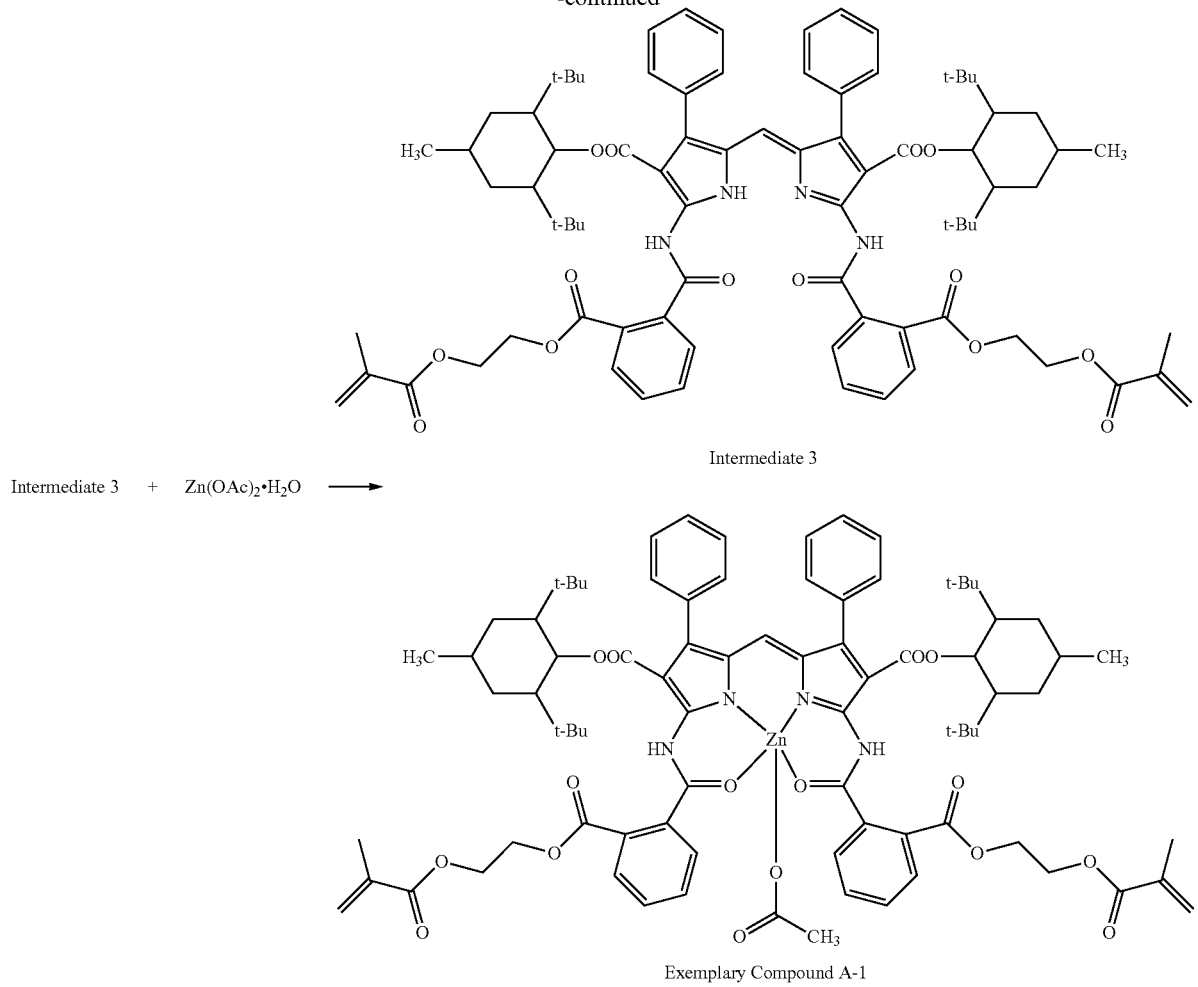

Exemplary Compound A-1

(Synthesis of Intermediate 1)

Intermediate 1 can be synthesized by the method described in U.S. Patent Application Publication No. 2008/0076044.

(Synthesis of Intermediate 2)

40.7 g (0.14 mol) of 2-methacryloyloxyethylphthalic acid was added to 60 ml of N-methylpyrrolidone, and the mixture was stirred in an ice bath. To this solution, 17.3 g (0.14 mol) of thionyl chloride was added dropwise, and the resulting mixture was stirred for one hour in an ice bath and for another one hour at room temperature. Thus, an acid halide solution was obtained.

100 ml of N-methylpyrrolidone was added to 49.2 g (0.12 mol) of Intermediate 1 obtained by the method described in U.S. Patent Application Publication No. 2008/0076044, and the mixture was stirred under ice cooling. Subsequently, the solution described above was added dropwise thereto. Thereafter, the resulting mixture was stirred for 1 hour under ice cooling, and for another 3 hours at room temperature.

After completion of the reaction, the reaction liquid was dissolved in 500 ml of ethyl acetate, and the solution was subjected to purification by liquid-liquid separation using 500 ml of water. The organic layer was dried over sodium sulfate and then filtered, and the filtrate was concentrated under reduced pressure. A solid thus obtained was washed with acetonitrile and dried. In this manner, 65 g (yield: 81%) of Intermediate 2 was obtained.

Furthermore, the details of $^1$H-NMR (CDCl$_3$) were as follows: δ: 11.04 (s, 1H), 10.86 (s, 1H), 7.92 (d, 1H), 7.72-7.35 (m, 9H), 6.35 (s, 1H), 6.11 (s, 1H), 5.82 (s, 1H), 5.56 (s, 1H), 4.58 (m, 2H), 4.42 (m, 2H), 1.95 (s, 3H), 1.27-1.12 (m, 4H), 1.06-0.92 (m, 2H), 0.84 (s, 18H), 0.70 (d, 3H), 0.63-0.47 (m, 2H).

(Synthesis of Intermediate 3)

33.5 g (0.05 mol) of Intermediate 2 and 3.7 g (0.025 mol) of triethyl ortho-formate were added to 50 ml of acetic anhydride, and the mixture was stirred at room temperature. 75 ml of trifluoroacetic acid was added dropwise to this solution, and the resulting mixture was stirred for 5 hours at room temperature. After completion of the reaction, the reaction liquid was poured into a solution obtained by adding 112 g of sodium hydrogen carbonate to 170 ml of ethyl acetate and 750 ml of water, the mixture was stirred for one hour, and then a precipitate was filtered. A solid thus obtained was purified by silica gel chromatography using a solution of hexane/ethyl acetate=5/1, and thus 13.5 g (40%) of Intermediate 3 was obtained.

Furthermore, the details of $^1$H-NMR (CDCl$_3$) were as follows: δ: 11.08 (s, 2H), 7.92 (m, 4H), 7.39-7.13 (m, 14H), 6.15 (s, 1H), 6.02 (s, 2H), 5.98 (s, 2H), 5.44 (s, 2H), 4.56 (m, 4H), 4.40 (m, 4H), 1.95 (s, 6H), 1.30-1.08 (m, 8H), 0.98-0.92 (m, 4H), 0.84 (m, 36H), 0.65 (d, 6H), 0.50-0.35 (m, 4H).

(Synthesis of Exemplary Compound A-1)

6.8 g (0.005 mol) of Intermediate 3 was added to 50 ml of tetrahydrofuran, and the mixture was stirred at room temperature. A liquid obtained by adding 1.3 g (0.006 mol) of zinc acetate dihydrate to 25 ml of methanol was added to the liquid, and the resulting mixture was stirred for 3 hours. Thereafter, the reaction liquid and a precipitated solid were filtered, and the filter residue thus obtained was added to 150 ml of methanol. The resulting mixture was stirred for one hour. Thereafter, the mixture was concentrated under reduced pressure, and a solid thus obtained was purified by silica gel chromatography. In this manner, 5.2 g (70%) of Exemplary Compound A-1 was obtained.

Furthermore, the details of $^1$H-NMR (CDCl$_3$) were as follows: δ: 11.38 (s, 2H), 7.93 (t, 4H), 7.71-7.52 (m, 4H), 7.32-7.10 (m, 12H), 6.28 (s, 1H), 6.08 (s, 2H), 5.80 (s, 2H), 5.53 (s, 2H), 4.43 (m, 4H), 4.25 (m, 4H), 1.86 (s, 6H), 1.22 (m, 6H), 0.98 (d, 4H), 0.88 (s, 36H), 0.64 (d, 6H), 0.52 (m, 2H), 0.28 (m, 2H).

The dipyrromethene-metal complex compound according to the invention or tautomers thereof can all be synthesized according to the reaction scheme A. Furthermore, if necessary, the dipyrromethene-metal complex compound according to the invention or a tautomer thereof can be synthesized by making reference to the methods described in, for example, U.S. Pat. Nos. 4,774,339; 5,433,896; JP-A No. 2001-240761; JP-A No. 2002-155052; WO 2008/0076044 A; Japanese Patent No. 3614586; Aust. J. Chem, 1965, 11, 1835-1845; or J. H. Boger et al, Heteroatom Chemistry, Vol. 1, No. 5, 389 (1990).

<Anthraquinone Compound>

The colored composition of the invention is constituted using at least one or more selected from compounds represented by formula (I) and tautomers thereof, and may further include an anthraquinone compound.

When the colored composition includes an anthraquinone compound, the contrast of a color filter obtained by using the colored composition of the invention can be effectively increased.

The anthraquinone compound in the invention is a compound having an absorption maximum in the range of 400 nm to 700 nm, and in this invention, the anthraquinone compound preferably has an absorption maximum in the range of 500 nm to 700 nm, and particularly preferably has an absorption maximum in the range of 550 nm to 700 nm. There are no particular limitations in terms of structure as long as the compound is an anthraquinone compound having such an absorption maximum, and the contrast enhancing effect is excellent.

Among the anthraquinone compounds in the invention, preferred compounds are aminoanthraquinone compounds represented by the following formula (IX).

Among these aminoanthraquinone compounds, from the viewpoint of the absorption characteristics, a compound represented by the following formula (X) is more preferred, and also from the viewpoint of heat stability, a compound represented by the following formula (XI) is more preferred. Furthermore, from the viewpoint of achieving a balance between the absorption characteristics and heat stability, a compound represented by the following formula (XII) or the following formula (XIII) is particularly preferred.

First, an aminoanthraquinone compound represented by the following formula (IX) is described.

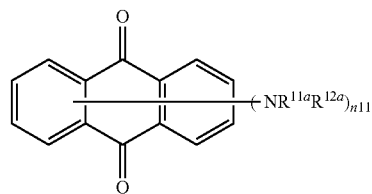

Formula (IX)

In formula (IX), $R^{11a}$ and $R^{12a}$ each independently represent a hydrogen atom, an alkyl group, an aryl group, or a heterocyclic group, but $R^{11a}$ and $R^{12a}$ do not simultaneously represent hydrogen atoms.

The alkyl group represented by $R^{11a}$ and $R^{12a}$ is preferably an alkyl group having 1 to 30 carbon atoms, more preferably 1 to 20 carbon atoms, and particularly preferably 1 to 10 carbon atoms, and examples thereof include methyl, ethyl, isopropyl, tert-butyl, n-octyl, n-decyl, n-hexadecyl, cyclopropyl, cyclopentyl, and cyclohexyl.

The aryl group represented by $R^{11a}$ and $R^{12a}$ is preferably an aryl group having 6 to 30 carbon atoms, more preferably 6 to 20 carbon atoms, and particularly preferably 6 to 12 carbon atoms, and examples thereof include phenyl, o-methylphenyl, p-methylphenyl, 2,6-dimethylphenyl, 2,6-diethylphenylbiphenyl, 2,6-dibromophenyl, naphthyl, anthranil, and phenanthryl.

The heterocyclic group represented by $R^{11a}$ and $R^{12a}$ is preferably a heterocyclic group having 1 to 30 carbon atoms, and more preferably 1 to 12 carbon atoms, and the heterocyclic group contains, as a heteroatom, for example, a nitrogen atom, an oxygen atom, or a sulfur atom. Examples of the heterocyclic group include imidazolyl, pyridyl, quinolyl, furyl, thienyl, benzoxazolyl, benzimidazolyl, benzothiazolyl, naphthothiazolyl, benzoxazolyl, a carbazolyl group, and an azepinyl group.

The alkyl group, aryl group and heterocyclic group represented by $R^{11a}$ and $R^{12a}$ may further have a substituent.

Examples of the substituents in the case where any of those groups have a substituent, include an alkyl group (preferably, an alkyl group having 1 to 30 carbon atoms, more preferably 1 to 20 carbon atoms, and particularly preferably 1 to 10 carbon atoms; examples include methyl, ethyl, isopropyl, tert-butyl, n-octyl, n-decyl, n-hexadecyl, cyclopropyl, cyclopentyl, and cyclohexyl), an alkenyl group (preferably, an alkenyl group having 2 to 30 carbon atoms, more preferably 2 to 20 carbon atoms, and particularly preferably 2 to 10 carbon atoms; examples include vinyl, allyl, 2-butenyl, and 3-pentenyl), an alkynyl group (preferably, an alkynyl group having 2 to 30 carbon atoms, more preferably 2 to 20 carbon atoms, and particularly preferably 2 to 10 carbon atoms; examples include propargyl and 3-pentynyl), an aryl group (preferably, an aryl group having 6 to 30 carbon atoms, more preferably 6 to 20 carbon atoms, and particularly preferably 6 to 12 carbon atoms; examples include phenyl, p-methylphenyl, biphenyl, naphthyl, anthranil, and phenanthryl), an amino group (preferably, an amino group having 0 to 30 carbon atoms, more preferably 0 to 20 carbon atoms, and particularly preferably 0 to 10 carbon atoms, which includes an alkylamino group, an arylamino group, and a heterocyclic amino group; specific examples include amino, methylamino, dimethylamino, diethylamino, dibenzylamino, diphenylamino, and ditolylamino), an alkoxy group (preferably, an alkoxy group having 1 to 30 carbon atoms, more preferably 1 to 20 carbon atoms, and particularly preferably 1 to 10 carbon atoms; examples include methoxy, ethoxy, butoxy, and 2-ethylhexyloxy), an aryloxy group (preferably, an aryloxy group having 6 to 30 carbon atoms, more preferably 6 to 20 carbon atoms, and particularly preferably 6 to 12 carbon atoms; examples include phenyloxy, 1-naphthyloxy, and 2-naphthyloxy), an aromatic heterocyclic oxy group (preferably, an aromatic heterocyclic oxy group having 1 to 30 carbon atoms, more preferably 1 to 20 carbon atoms, and particularly preferably 1 to 12 carbon atoms; examples include pyridyloxy, pyrazyloxy, pyrimidyloxy, and quinolyloxy), an acyl group (preferably, an acyl group having 1 to 30 carbon atoms, more preferably 1 to 20 carbon atoms, and particularly preferably 1 to 12 carbon atoms; examples include acetyl, benzoyl, formyl, and pivaloyl), an alkoxycarbonyl group (preferably, an alkoxycarbonyl group having 2 to 30 carbon atoms, more preferably 2 to 20 carbon atoms, and particularly preferably 2 to 12 carbon atoms; examples include methoxycarbonyl and ethoxycarbonyl), an aryloxycarbonyl group (preferably, an aryloxycarbonyl group having 7 to 30 carbon atoms, more preferably 7 to 20 carbon atoms, and particularly preferably 7 to 12 carbon atoms; examples include phenyloxycarbonyl), an acyloxy group (preferably, an acyloxy group having 2 to 30 carbon atoms, more preferably 2 to 20 carbon atoms, and particularly preferably 2 to 10 carbon atoms; examples include acetoxy and benzoyloxy), an acylamino group (preferably, an acylamino group having 2 to 30 carbon atoms, more preferably 2 to 20 carbon atoms, and particularly preferably 2 to 10 carbon atoms; examples include acetylamino and benzoylamino), an alkoxycarbonylamino group (preferably, an alkoxycarbonylamino group having 2 to 30 carbon atoms, more preferably 2 to 20 carbon atoms, and particularly preferably 2 to 12 carbon atoms; examples include methoxycarbonylamino), an aryloxycarbonylamino group (preferably, an aryloxycarbonyloamino group having 7 to 30 carbon atoms, more preferably 7 to 20 carbon atoms, and particularly preferably 7 to 12 carbon atoms; examples include phenyloxycarbonylamino), a sulfonylamino group (preferably, a sulfonylamino group having 1 to 30 carbon atoms, more preferably 1 to 20 carbon atoms, and particularly preferably 1 to 12 carbon atoms; examples include methanesulfonylamino and benzenesulfonylamino), a sulfamoyl group (preferably, a sulfamoyl group having 0 to 30 carbon atoms, more preferably 0 to 20 carbon atoms, and particularly preferably 0 to 12 carbon atoms; examples include sulfamoyl, methylsulfamoyl, dimethylsulfamoyl, and phenylsulfamoyl), a carbamoyl group (preferably, a carbamoyl group having 1 to 30 carbon atoms, more preferably 1 to 20 carbon atoms, and particularly preferably 1 to 12 carbon atoms; examples include carbamoyl, methylcarbamoyl, diethylcarbamoyl, and phenylcarbamoyl), an alkylthio group (preferably, an alkylthio group having 1 to 30 carbon atoms, more preferably 1 to 20 carbon atoms, and particularly preferably 1 to 12 carbon atoms; examples include methylthio and ethylthio), an arylthio group (preferably, an arylthio group having 6 to 30 carbon atoms, more preferably 6 to 20 carbon atoms, and particularly preferably 6 to 12 carbon atoms; examples include phenylthio), an aromatic heterocyclic thio group (preferably, an aromatic heterocyclic thio group having 1 to 30 carbon atoms, more preferably 1 to 20 carbon atoms, and particularly preferably 1 to 12 carbon atoms; examples include pyridylthio, 2-benzimidazolylthio, 2-benzoxazolylthio, and 2-benzothiazolylthio), a sulfonyl group (preferably, a sulfonyl group having 1 to 30 carbon atoms, more preferably 1 to 20 carbon atoms, and particularly preferably 1 to 12 carbon atoms; examples include mesyl and tosyl), a sulfinyl group (preferably, a sulfinyl group having 1 to 30 carbon atoms, more preferably 1 to 20 carbon atoms, and particularly preferably 1 to 12 carbon atoms; examples include methanesulfinyl and benzenesulfinyl), a ureido group (preferably, a ureido group having 1 to 30 carbon atoms, more preferably 1 to 20 carbon atoms, and particularly preferably 1 to 12 carbon atoms; examples include ureido, methylureido, and phenylureido), a phosphoric amide group (preferably, a phosphoric amide group having 1 to 30 carbon atoms, more preferably 1 to 20 carbon atoms, and particularly preferably 1 to 12 carbon atoms; examples include diethylphosphoric amide and phenylphosphoric amide), a hydroxyl group, a mercapto group, a halogen atom (examples include a fluorine atom, a chlorine atom, a bromine atom, and an iodine atom), a cyano group, a sulfo group, a carboxyl group, a nitro group, a hydroxamic acid group, a sulfino group, a hydrazino group, an imino group, a heterocyclic group (preferably, a heterocyclic group having 1 to 30 carbon atoms, and more preferably 1 to 12 carbon atoms, which contains, as a heteroatom, for example, a nitrogen atom, an oxygen atom or a sulfur atom; specific examples include imidazolyl, pyridyl, quinolyl, furyl, thienyl, piperidyl, morpholino, benzoxazolyl, benzimidazolyl, benzothiazolyl, a carbazolyl group, and an azepinyl group), and a silyl group (preferably, a silyl group having 3 to 40 carbon atoms, more preferably 3 to 30 carbon atoms, and particularly preferably 3 to 24 carbon atoms; examples include trimethylsilyl and triphenylsilyl). These substituents may be further substituted.

In formula (IX), $n^{11}$ represents an integer from 1 to 4, and when $n^{11}$ is an integer from 2 to 4, plural $NR^{11a}R^{12a}$ may be identical to or different from each other.

Next, a diaminoanthraquinone compound represented by formula (X) is described.

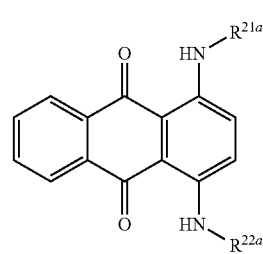

Formula (X)

In formula (X), $R^{21a}$ and $R^{22a}$ each independently represent an alkyl group or an aryl group.

The alkyl group represented by $R^{21a}$ and $R^{22a}$ is preferably an alkyl group having 1 to 30 carbon atoms, more preferably 1 to 20 carbon atoms, and particularly preferably 1 to 10 carbon atoms, and examples thereof include methyl, ethyl, isopropyl, tert-butyl, n-octyl, n-decyl, n-hexadecyl, cyclopropyl, cyclopentyl, and cyclohexyl.

The aryl group represented by $R^{21a}$ and $R^{22a}$ is preferably an aryl group having 6 to 30 carbon atoms, more preferably 6 to 20 carbon atoms, and particularly preferably 6 to 12 carbon atoms, and examples thereof include phenyl, o-methylphenyl, p-methylphenyl, 2,6-dimethylphenyl, 2,6-diethylphenylbiphenyl, 2,6-dibromophenyl, naphthyl, anthranil, and phenanthryl.

The alkyl group and aryl group represented by $R^{21a}$ and $R^{22a}$ may further have a substituent, and examples of the substituents include those described above as examples of the substituents for the alkyl group, aryl group and heterocyclic group represented by $R^{11a}$ and $R^{12a}$ in the formula (IX). Among them, preferred examples of the substituents include an alkyl group, an aryl group, an amino group, an alkoxy group, an aryloxy group, an acyl group, an alkoxycarbonyl group, an aryloxycarbonyl group, an acyloxy group, an acylamino group, a sulfonylamino group, a sulfamoyl group, a sulfonyl group, a ureido group, a hydroxyl group, a halogen atom, a sulfo group, and a carboxyl group. The details and preferred embodiments of these are as described above.

Next, a diaminoanthraquinone compound represented by formula (XI) is described.

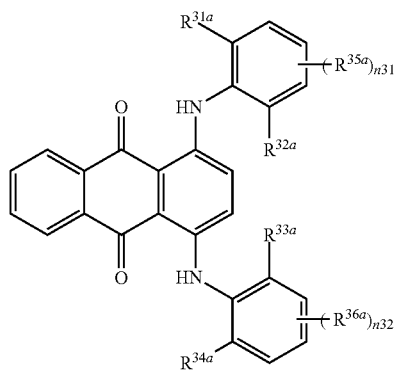

Formula (XI)

In formula (XI), $R^{31a}$, $R^{32a}$, $R^{33a}$ and $R^{34a}$ each independently represent an alkyl group or a halogen atom.

The alkyl group represented by $R^{31a}$, $R^{32a}$, $R^{33a}$ and $R^{34a}$ is preferably an alkyl group having 1 to 10 carbon atoms, more preferably 1 to 5 carbon atoms, and particularly preferably 1 to 2 carbon atoms, and examples thereof include methyl, ethyl, isopropyl, tert-butyl, n-octyl, n-decyl, n-hexadecyl, cyclopropyl, cyclopentyl, and cyclohexyl.

Examples of the halogen atom represented by $R^{31a}$, $R^{32a}$, $R^{33a}$ and $R^{34a}$ include a fluorine atom, a chlorine atom, a bromine atom, an iodine atom, and a chlorine atom and a bromine atom are preferred.

In formula (XI), $R^{35a}$ and $R^{36a}$ each independently represent an alkyl group, an alkoxy group, an aryloxy group, a sulfo group or a salt thereof, an aminosulfonyl group, an alkoxysulfonyl group, or an aryloxysulfonyl group.

The alkyl group represented by $R^{35a}$ and $R^{36a}$ has the same definition as the alkyl group represented by $R^{31a}$, $R^{32a}$, $R^{33a}$ and $R^{34a}$, and preferable embodiments of the alkyl group represented by $R^{35a}$ and $R^{36a}$ are the same as those of the aforementioned alkyl group.

The alkoxy group represented by $R^{35a}$ and $R^{36a}$ is preferably an alkoxy group having 1 to 30 carbon atoms, more preferably 1 to 20 carbon atoms, and particularly preferably 1 to 10 carbon atoms, and examples thereof include methoxy, ethoxy, butoxy, and 2-ethylhexyloxy.

The aryloxy group represented by $R^{35a}$ and $R^{36a}$ is preferably an aryloxy group having 6 to 30 carbon atoms, more preferably 6 to 20 carbon atoms, and particularly preferably 6 to 12 carbon atoms, and examples thereof include phenyloxy, 1-naphthyloxy, and 2-naphthyloxy.

The sulfo group and a salt thereof represented by $R^{35a}$ and $R^{36a}$ are preferably a sulfonic acid group and a group derived from a sulfonic acid salt. The sulfonic acid salt is preferably a quaternary ammonium salt or a salt of an amine, and is particularly preferably a sulfonic acid salt having 4 to 30 (preferably 10 to 30, and more preferably 15 to 30) carbon atoms.

The aminosulfonyl group represented by $R^{35a}$ and $R^{36a}$ is preferably an aminosulfonyl group having 1 to 30 carbon atoms, more preferably 2 to 20 carbon atoms, and particularly preferably 2 to 15 carbon atoms, and specific examples thereof include an ethylaminosulfonyl group, a propylaminosulfonyl group, an isopropylaminosulfonyl group, a butylaminosulfonyl group, an isobutylaminosulfonyl group, a sec-butylaminosulfonyl group, a pentylaminosulfonyl group, an isopentylaminosulfonyl group, a hexylaminosulfonyl group, a cyclohexylaminosulfonyl group, a 2-ethylhexylaminosulfonyl group, a decylaminosulfonyl group, a dodecylaminosulfonyl group, and a phenylaminosulfonyl group. Examples of the dialkylaminosulfonyl group include a dimethylaminosulfonyl group, a diethylaminosulfonyl group, a dipropylaminosulfonyl group, a diisopropylaminosulfonyl group, a dibutylaminosulfonyl group, a di-sec-butylaminosulfonyl group, a di-sec-propylaminosulfonyl group, a dihexylaminosulfonyl group, a methylethylaminosulfonyl group, a methylbutylaminosulfonyl group, an ethylbutylaminosulfonyl group, and a phenylmethylaminosulfonyl group. Among these, a dialkylaminosulfonyl group having an alkyl moiety having 4 to 15 carbon atoms is particularly preferred.

The alkoxysulfonyl group represented by $R^{35a}$ and $R^{36a}$ is preferably an alkoxysulfonyl group having 1 to 30 carbon atoms, more preferably 2 to 20 carbon atoms, even more preferably 2 to 15 carbon atoms, and particularly preferably 4 to 15 carbon atoms, and specific examples thereof include a butoxysulfonyl group, a hexyloxysulfonyl group, a decyloxysulfonyl group, and a dodecyloxysulfonyl group.

The aryloxysulfonyl group represented by $R^{35a}$ and $R^{36a}$ is preferably an aryloxysulfonyl group having 6 to 30 carbon atoms, more preferably 6 to 20 carbon atoms, and particularly preferably 6 to 15 carbon atoms, and specific examples thereof include a phenoxysulfonyl group and a tolyloxysulfonyl group.

$R^{35a}$ and $R^{36a}$ may further have a substituent, and examples of the substituents include those described above as the examples of the substituents for the alkyl group, aryl group and heterocyclic group represented by $R^{11a}$ and $R^{12a}$ in formula (IX).

In formula (XI), $n^{31}$ and $n^{32}$ each represent an integer from 0 to 2, and when $n^{31}$ and $n^{32}$ are each 2, plural $R^{35a}$'s and plural $R^{36a}$'s may be identical to or different from each other.

Among the compounds described above, a compound selected from diaminoanthraquinone compounds represented by the following formula (XII) or the following formula (XIII) is preferred.

(Diaminoanthraquinone Compound Represented by Formula (XII))

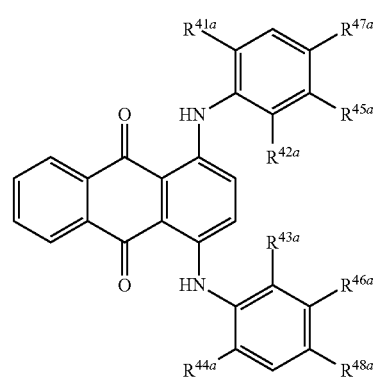

Formula (XII)

In formula (XII), $R^{41a}$, $R^{42a}$, $R^{43a}$ and $R^{44a}$ each independently represent an alkyl group or a halogen atom. $R^{41a}$, $R^{42a}$, $R^{43a}$ and $R^{44a}$ have the same definitions as the alkyl group or the halogen atom for $R^{31a}$, $R^{32a}$, $R^{33a}$ and $R^{34a}$ in formula (XI) as described above, and the preferable embodiments are the same as those of the alkyl group or the halogen atom for $R^{31a}$, $R^{32a}$, $R^{33a}$ and $R^{34a}$ in formula (XI) as described above.

$R^{45a}$, $R^{46a}$, $R^{47a}$ and $R^{48a}$ in formula (XII) each independently represent an alkyl group, a sulfo group or a salt thereof, or an aminosulfonyl group. Any one of $R^{45a}$ and $R^{47a}$, and any one of $R^{46a}$ and $R^{48a}$ each represent a sulfo group or a salt thereof, or an aminosulfonyl group. $R^{45a}$, $R^{46a}$, $R^{47a}$ and $R^{48a}$ have the same definitions as the alkyl group, sulfo group or a salt thereof, or aminosulfonyl group represented by $R^{35a}$ and $R^{36a}$ in formula (XI), and preferable embodiments are the same as those of the alkyl group, sulfo group or a salt thereof, or aminosulfonyl group represented by $R^{35a}$ and $R^{36a}$ in formula (XI).

(Diaminoanthraquinone Compound Represented by Formula (XIII))

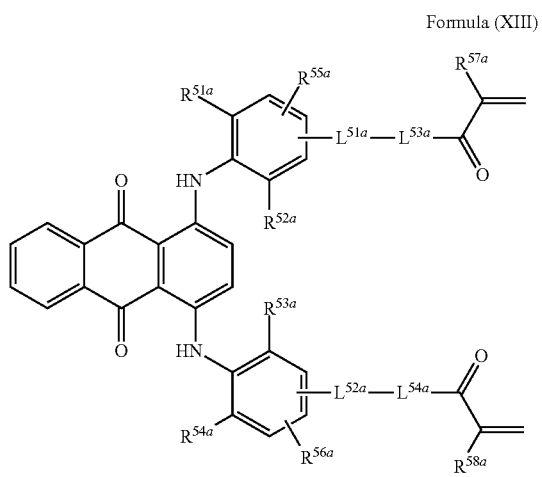

Formula (XIII)

In formula (XIII), $R^{51a}$, $R^{52a}$, $R^{53a}$ and $R^{54a}$ each independently represent an alkyl group or a halogen atom, and have the same definitions as the alkyl group or the halogen atom for $R^{31a}$, $R^{32a}$, and $R^{34a}$ in formula (XI), and preferable embodiments are the same as as those of the alkyl group or the halogen atom for $R^{31a}$, $R^{32a}$, $R^{33a}$ and $R^{34a}$ in formula (XI).

In formula (XIII), $R^{55a}$ and $R^{56a}$ each independently represent a hydrogen atom or an alkyl group, and the alkyl group has the same definition as the alkyl group for $R^{31a}$, $R^{32a}$, $R^{33a}$ and $R^{34a}$ in formula (XI), and preferable embodiment are the same as the alkyl group for $R^{31a}$, $R^{32a}$, $R^{33a}$ and $R^{34a}$ in formula (XI).

$R^{57a}$ and $R^{58a}$ each independently represent a hydrogen atom or an alkyl group, and the alkyl group is preferably an alkyl group having 1 to 10 carbon atoms, more preferably an alkyl group having 1 to 5 carbon atoms, and particularly preferably a methyl group.

In formula (XIII), $L^{51a}$ and $L^{52a}$ each independently represent a divalent linking group, and preferred examples include an alkylene group having 1 to 10 carbon atoms, an arylene group having 6 to 20 carbon atoms, —O—, —S—, —NR—, —SO$_2$—, —CO—, and a divalent linking group formed by combining two or more of these groups. $L^{51a}$ and $L^{52a}$ are each more preferably an alkylene group having 1 to 10 carbon atoms, an arylene group having 6 to 12 carbon atoms, a sulfonylamino group, or a divalent linking group formed by combining two or more of these groups; and particularly preferably an alkylene group having 1 to 10 carbon atoms, a sulfonylamino group, or a divalent linking group formed by combining two or more of these groups.

The alkylene group having 1 to 10 carbon atoms, or a divalent linking group formed by combining the alkylene group having 1 to 10 carbon atoms with —O— or the like, may be unsubstituted or substituted, and examples include ethylene, propylene, a butylene group, an ethyleneoxy group, a propyleneoxy group, an ethyleneaminosulfonyl group, a propyleneaminosulfonyl group, a butyleneaminosulfonyl group, a pentyleneaminosulfonyl group, and a 1-methylethylenesulfonyl group. Among them, an alkyleneaminosulfonyl group having 2 to 10 carbon atoms (examples: an ethyleneaminosulfonyl group, a propyleneaminosulfonyl group, a butyleneaminosulfonyl group, or a pentyleneaminosulfonyl group) is preferred.

The arylene group having 6 to 20 carbon atoms, or a divalent linking group formed by combining the arylene group having 6 to 20 carbon atoms with —O— or the like, may be unsubstituted or substituted, and examples include phenylene, biphenylene, and a phenyleneaminosulfonyl group. Among these, an aryleneaminosulfonyl group having 6 to 12 carbon atoms (examples: a phenyleneaminosulfonyl group) is preferred.

Furthermore, R of —NR— represents a hydrogen atom or an alkyl group having 1 to 10 carbon atoms. Specific examples of the alkyl group include a methyl group, an ethyl group, a propyl group, an isobutyl group, a butyl group, an isobutyl group, a sec-butyl group, and a 2-ethylhexyl group.

In formula (XIII), $L^{53a}$ and $L^{54a}$ each independently represent an oxygen atom or a —NH— group.

Among those described above, a preferred anthraquinone compound in the invention is a compound selected from diaminoanthraquinone compounds represented by formula (XII) or formula (XIII), and the cases described below are particularly preferred. That is, in regard to formula (XII), a case in which $R^{41a}$, $R^{42a}$, $R^{43a}$ and $R^{44a}$ are each a methyl group, an ethyl group or a bromine atom; $R^{45a}$ and $R^{46a}$ are each an aminosulfonyl group having 2 to 15 carbon atoms; and $R^{47a}$ and $R^{48a}$ are each a methyl group, is preferred; and in regard to formula (XIII), a case in which $R^{51a}$, $R^{52a}$, $R^{53a}$ and $R^{54a}$ are each a methyl group, an ethyl group, or a bromine atom; $R^{55a}$ and $R^{56a}$ are each a hydrogen atom or a methyl group; $R^{57a}$ and $R^{58a}$ are each a hydrogen atom or a methyl group; $L^{51a}$ and $L^{52a}$ are each an alkyleneaminosulfonyl group having 1 to 10 carbon atoms, an aralkyleneaminosulfonyl group having 7 to 12 carbon atoms, or an alkyleneoxy group having 2 to 10 carbon atoms; and $L^{53a}$ and $L^{54a}$ are each an oxygen atom, is preferred.

In this case, a case in which the compound is used in combination with a dipyrromethene-metal complex compound represented by formula (I) is preferable from the viewpoint that the effects of the invention are more effectively provided.

Hereinbelow, specific examples of the anthraquinone compound according to the invention are described. However, the invention is not intended to be limited to these.

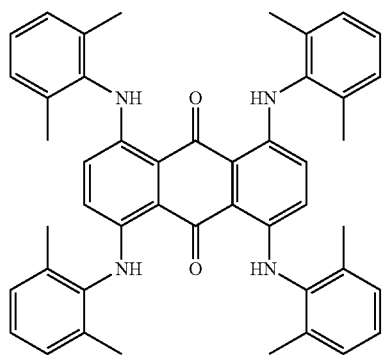
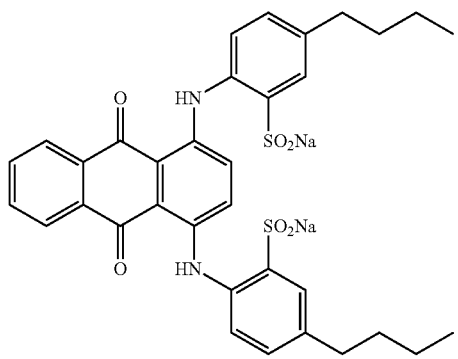
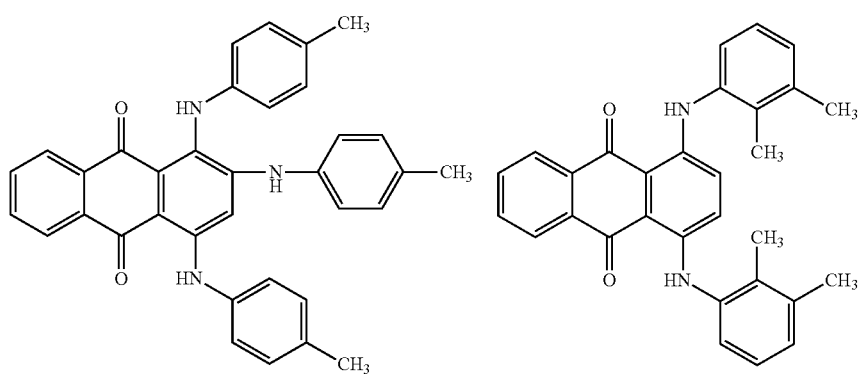
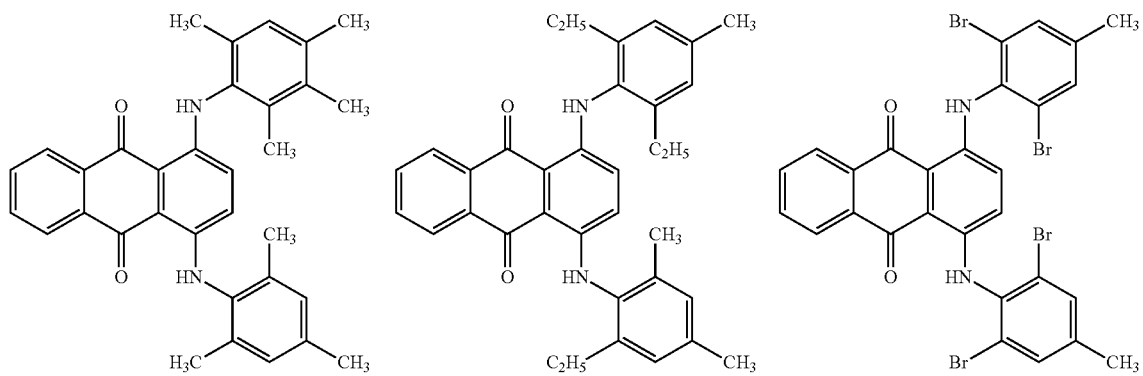
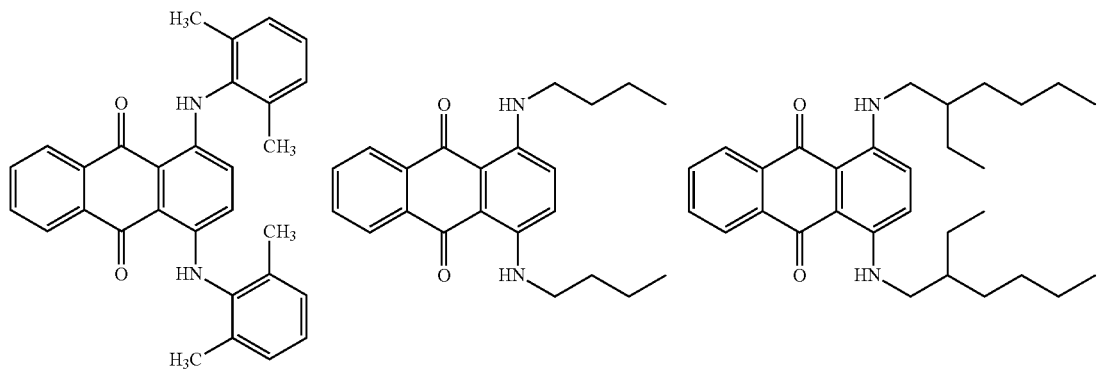

-continued
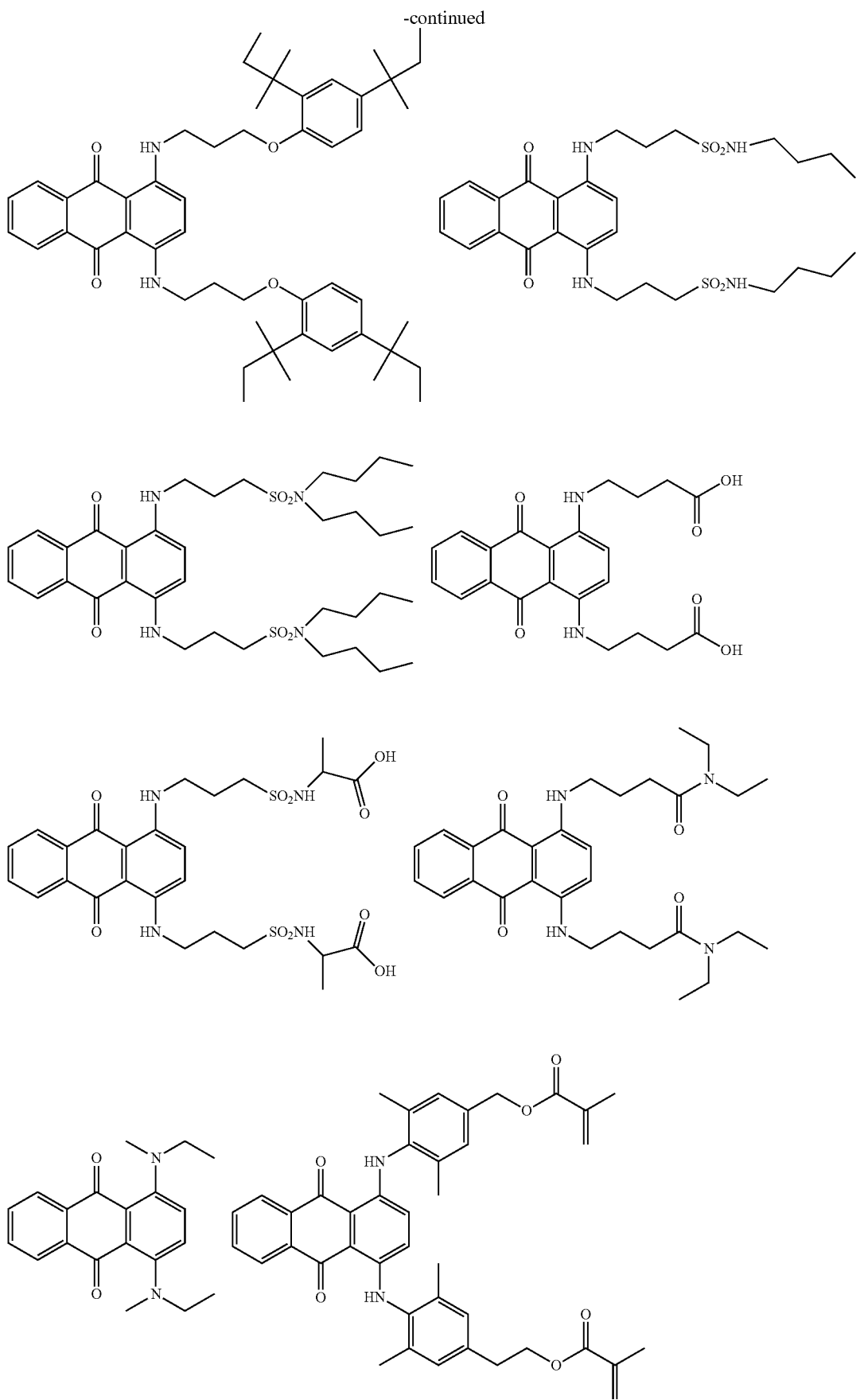

-continued
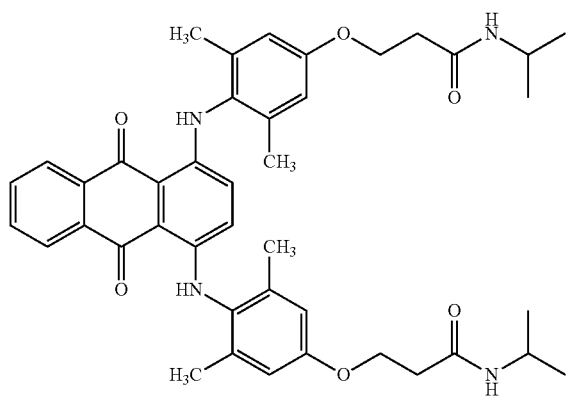
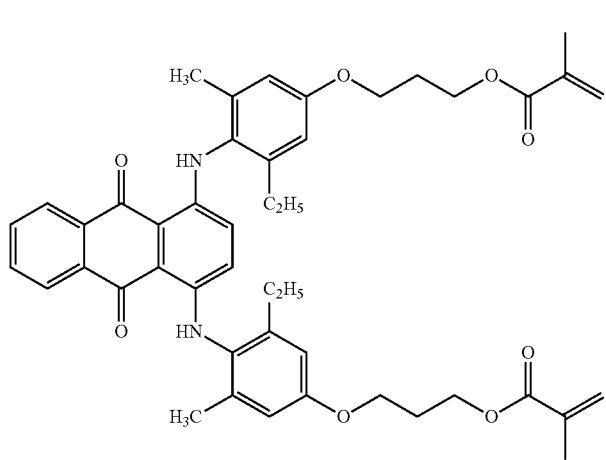
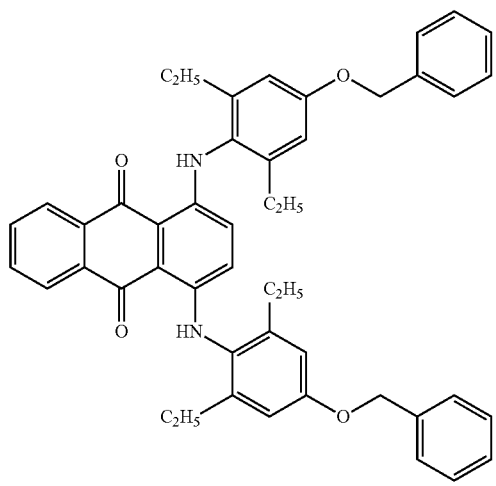
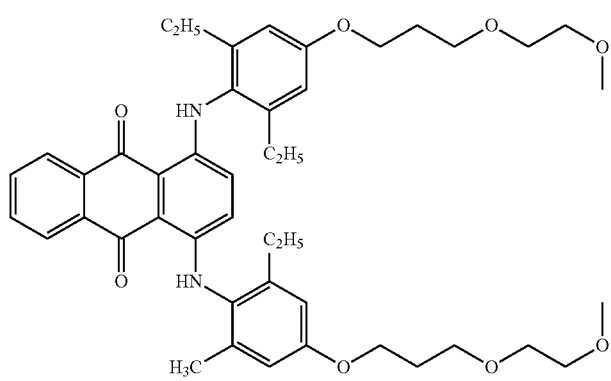
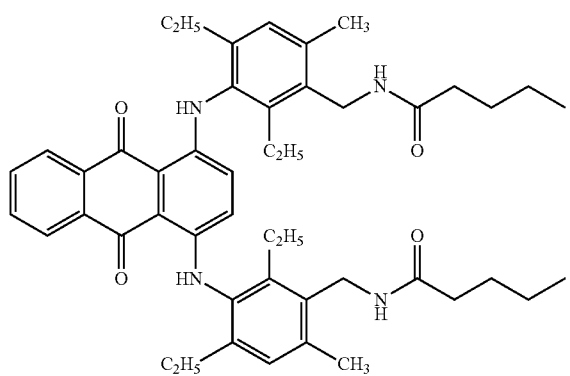

-continued
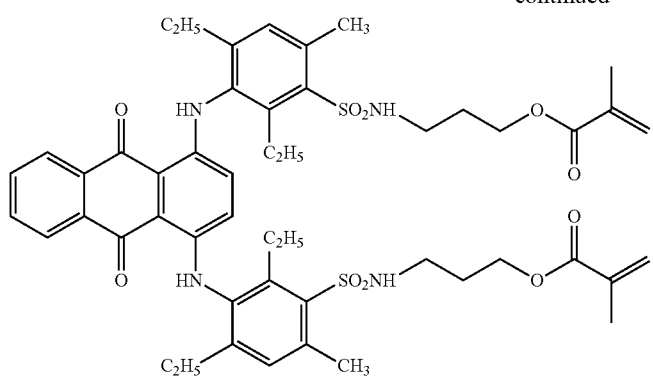
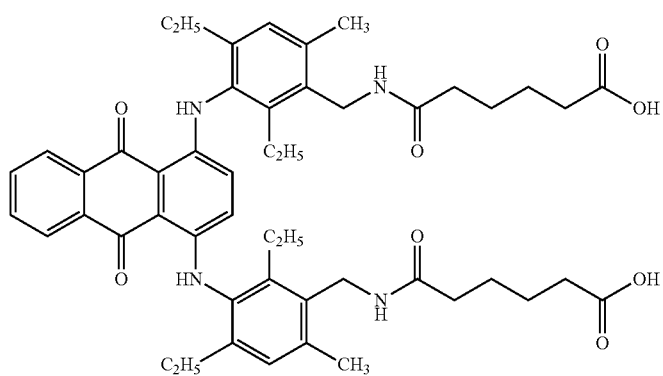
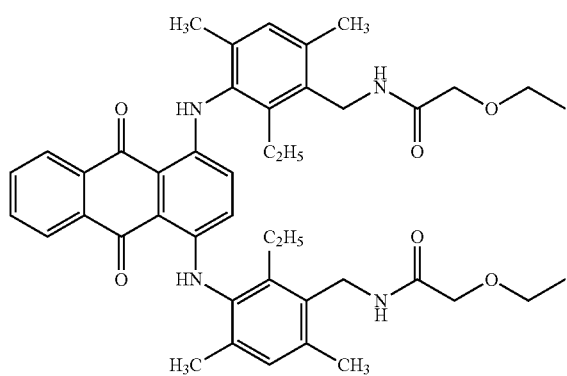
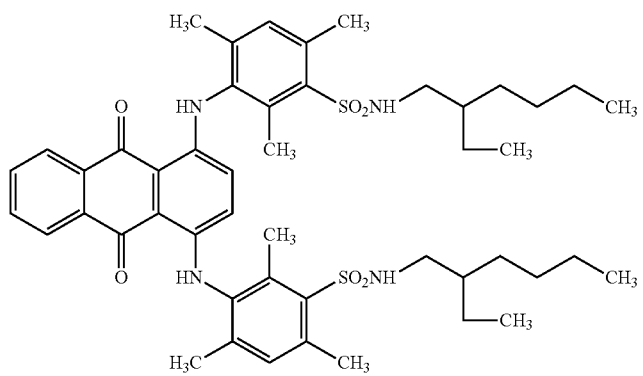
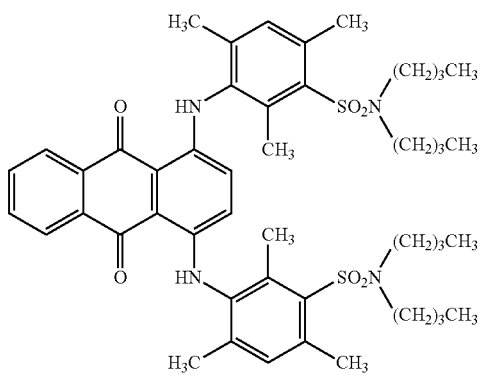

-continued
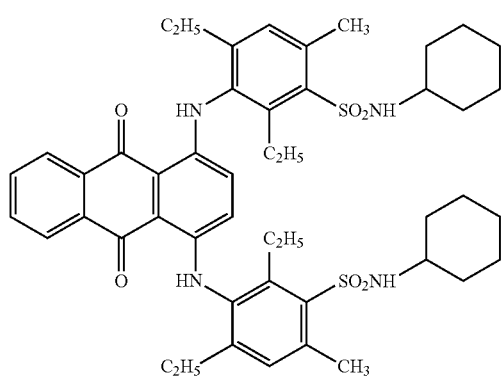
55
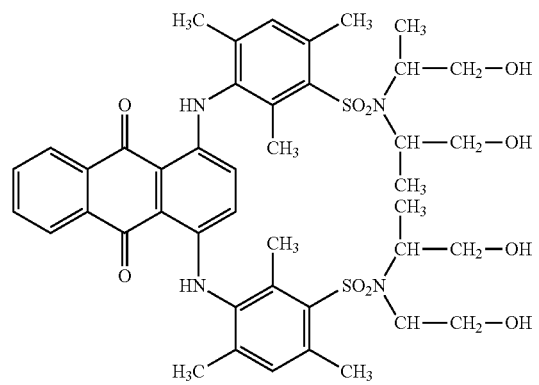
56
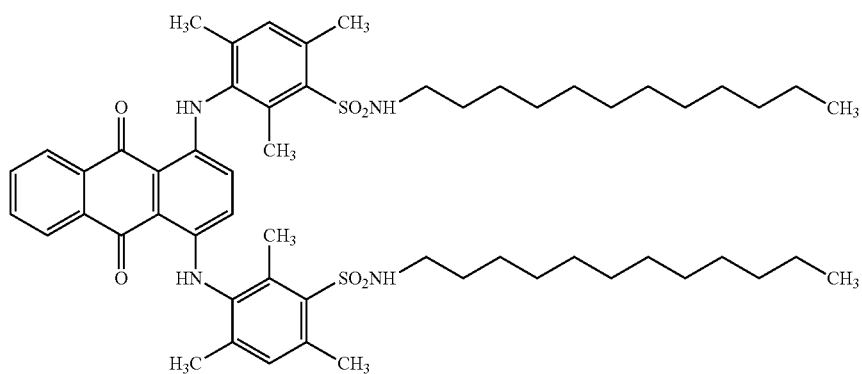
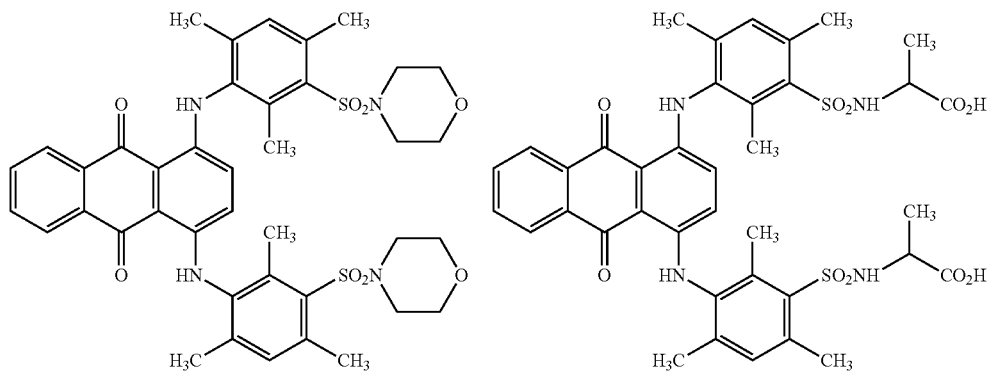
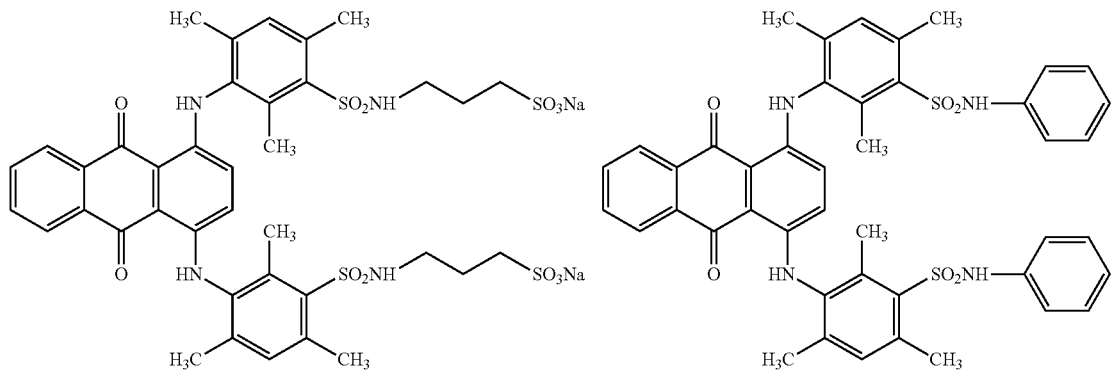

-continued
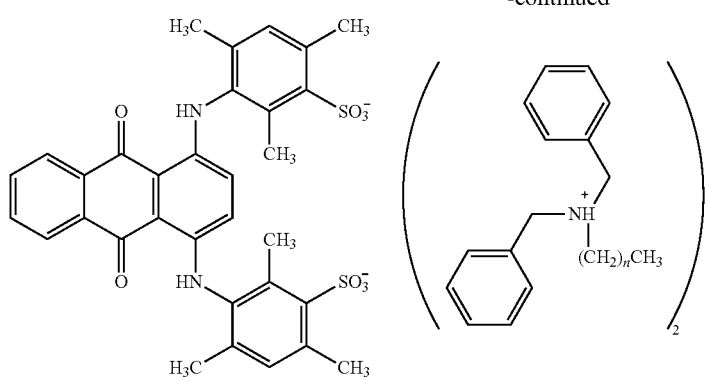
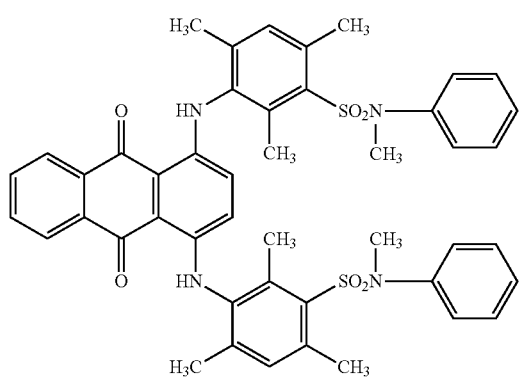
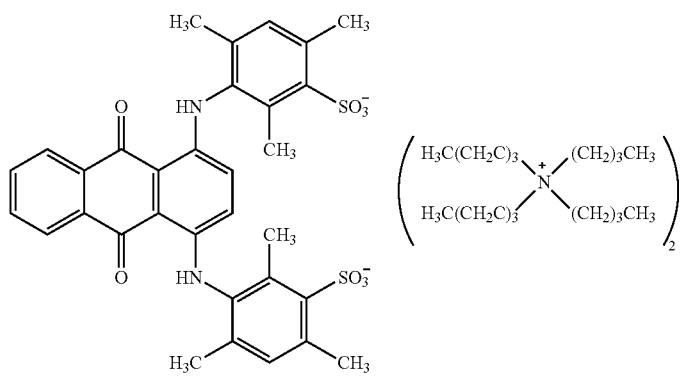
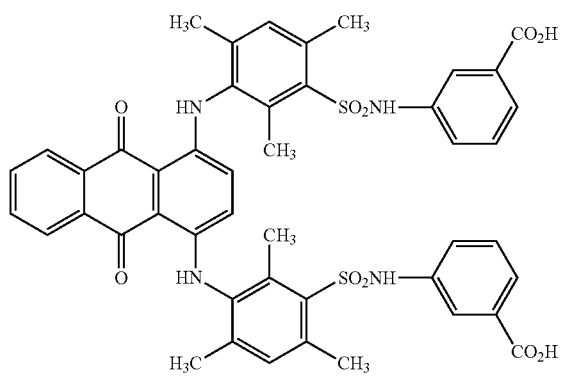

-continued
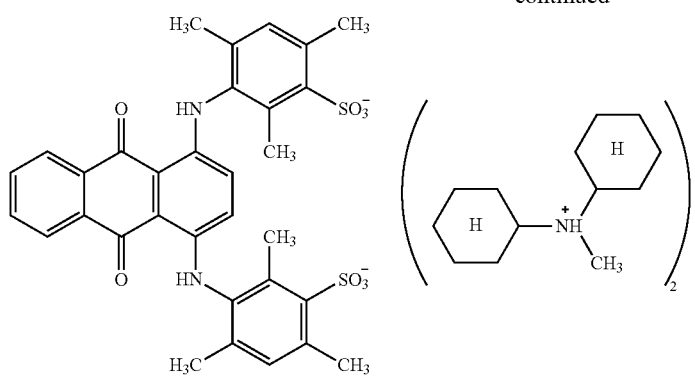
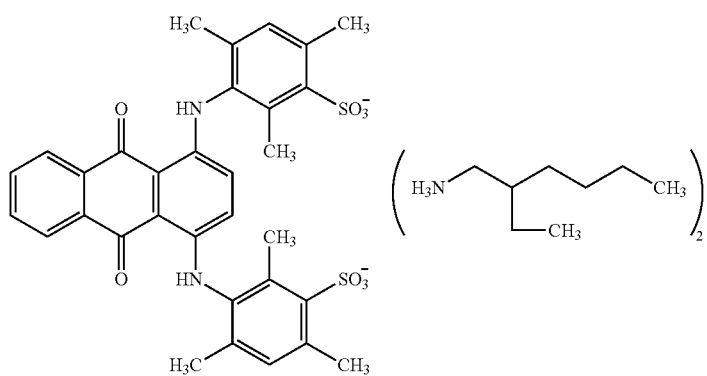
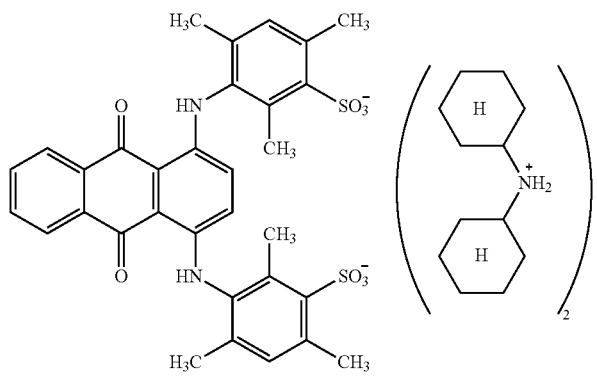
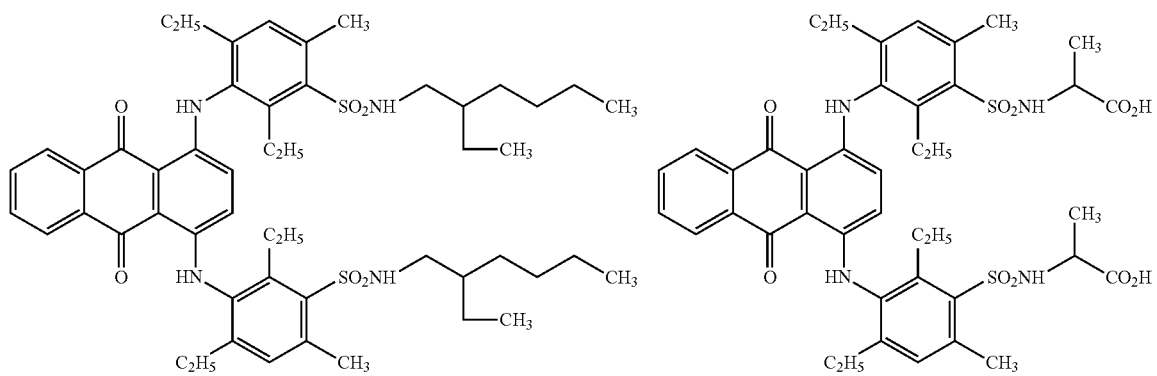

61 62

-continued

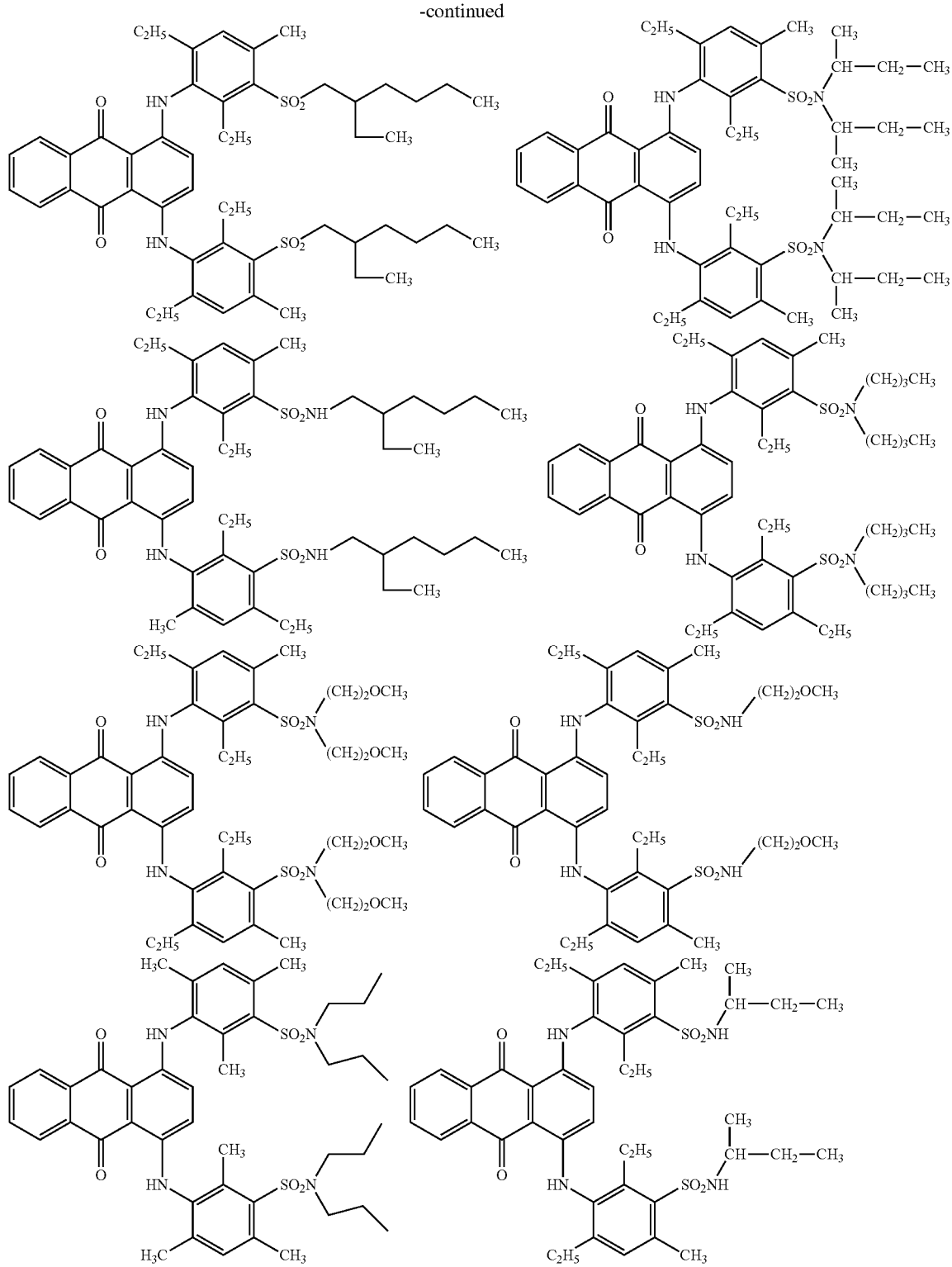

The proportion of the anthraquinone compound relative to the total amount of all the dye compounds including the compound represented by formula (I) or a tautomer thereof is preferably 50% by mass or less, more preferably in the range of 2% by mass to 50% by mass, and even more preferably in the range of 10% by mass to 50% by mass. When the proportion of the anthraquinone compound is 50% by mass or less, the color of colored images is satisfactory, and the contrast can be more effectively increased, while fastness properties are maintained.

<Dyes Having Another Structure>

In the colored composition of the invention, dyes having another structure can be used in addition to the pyrromethene dye. There are no particular limitations on the dyes having another structure, and any known dyes can be used. Examples include those coloring materials described in JP-A Nos. S64-90403, S64-91102, H1-94301, H6-11614, Japanese Patent No. 2592207, U.S. Pat. Nos. 4,808,501, 5,667,920, 5,059,500, JP-A Nos. H5-333207, H6-35183, H6-51115, H6-194828, H8-211599, H4-249549, H10-123316, H11-302283, H7-286107, 2001-4823, H8-15522, H8-29771, H8-146215, H11-343437, H8-62416, 2002-14220, 2002-14221, 2002-14222, 2002-14223, H8-302224, H8-73758, H8-179120, H8-151531, H6-230210, and the like.

Examples of the chemical structure of the dyes having other structures include pyrazole azo-based dyes, anilinoazo-based dyes, triphenylmethane-based dyes, anthraquinone-based dyes, anthrapyridone-based dyes, benzylidene-based dyes, oxonol-based, pyrazolotriazole azo-based dyes, pyridone azo-based dyes, cyanine-based dyes, phenothiazine-based dyes, pyrrolopyrazole azomethine-based dyes, xanthene-based dyes, squarylium-based dyes, phthalocyanine-based dyes, benzopyrane-based dyes, and indigo-based dyes. Among them, xanthene-based or squarylium-based dyes are preferred in view of hue.

The colored composition of the invention may include a single kind of dye, or may use two or more kinds of dyes in combination.

The content of the dye in the colored composition is preferably, on a mass basis, 0.1% to 30% by mass, and more preferably 0.5% to 20% by mass, relative to the total solid content of the colored composition. When the content of the dye is adjusted to the range described above, it is advantageous in that a good color density (for example, a color density suitable for liquid crystal display) is obtained, and good patterning of pixels can be provided.

(Pigment)

In the colored composition of the invention, the dye described above and a pigment can be used in combination. Regarding the pigment, a pigment having an average primary particle diameter of from 10 nm to 30 nm is preferred. With this embodiment, a colored composition having excellent hue and contrast is obtained.

Regarding the pigment, various inorganic pigments and organic pigments that are conventionally known can be used, but from the viewpoint of fastness properties, it is preferable to use an organic pigment. Examples of the organic pigment in the invention include the organic pigments described in paragraph [0093] of JP-A No. 2009-256572.

Furthermore, in particular,
C.I. Pigment Red 177, 224, 242, 254, 255, 264,
C.I. Pigment Yellow 138, 139, 150, 180, 185,
C.I. Pigment Orange 36, 38, 71,
C.I. Pigment Green 7, 36, 58,
C.I. Pigment Blue 15:6, and
C.I. Pigment Violet 23 are suitable from the viewpoint of color reproducibility, but the invention is not intended to be limited to these. One kind of these organic pigments can be used singly, or two or more kinds thereof can be used in various combinations in order to increase the color purity.

In the case of using a pigment, the content of the pigment in the colored composition of the invention is preferably 0.5% to 50% by mass, and more preferably 1% to 30% by mass, relative to the total solid content of the composition. When the content of the pigment is in the range described above, it is effective for securing excellent color characteristics.

<Pigment Dispersant>

The colored composition of the invention can include a pigment dispersant, if a pigment is included, together with the compound represented by formula (I) or a tautomer thereof.

Examples of the pigment dispersant that can be used in the invention include polymeric dispersants [for example, a polyamidoamine and salts thereof, a polycarboxylic acid and salts thereof, a high molecular weight unsaturated acid ester, a modified polyurethane, a modified polyester, a modified poly(meth)acrylate, a (meth)acrylic copolymer, and a naphthalenesulfonic acid-formalin condensate], and surfactants such as polyoxyethylene alkyl phosphoric acid esters, polyoxyethylene alkylamines, and alkanolamines; and pigment derivatives.

The polymeric dispersants can be further classified, based on the structure, into straight-chain polymers, terminal-modified polymers, graft polymers, and block polymers.

Examples of the terminal-modified polymers having an anchoring site to the pigment surface include those polymers having a phosphoric acid group at a terminal as described in JP-A No. H3-112992, Japanese Patent Application National Publication (Laid-Open) No. 2003-533455 and the like; polymers having a sulfonic acid group at a terminal as described in JP-A No. 2002-273191 and the like; and polymers having a partial skeleton of an organic coloring matter or a heterocyclic ring as described in JP-A No. H9-77994 and the like. Furthermore, a polymer having two or more anchoring sites to the pigment surface (an acid group, a basic group, a partial skeleton of an organic coloring matter, or a heterocyclic ring) introduced to a terminal of the polymer as described in JP-A No. 2007-277514, is also preferred due to excellent dispersion stability.

Examples of the graft polymer having an anchoring site to the pigment surface include polyester-based dispersants, and specific examples include a reaction product between a poly(lower alkyleneimine) and a polyester as described in JP-A No. S54-37082, Japanese Patent Application National Publication (Laid-Open) No. H8-507960, JP-A No. 2009-258668 and the like; a reaction product between a polyallylamine and a polyester as described in JP-A No. H9-169821 and the like; a copolymer of a macromonomer and a nitrogen atom monomer as described in JP-A Nos. H10-339949 and 2004-37986 and the like; a graft polymer having a partial skeleton of an organic coloring matter or a heterocyclic ring as described in JP-A Nos. 2003-238837, 2008-9426 and 2008-81732 and the like; and a copolymer of a macromonomer and an acid group-containing monomer as described in JP-A No. 2010-106268 and the like. Particularly, an amphoteric dispersed resin having a basic group and an acidic group as described in JP-A No. 2009-203462 is particularly preferred from the viewpoints of the dispersibility and dispersion stability of the pigment dispersion, and the developability exhibited by a colored composition using the pigment dispersion.

Regarding the macromonomer used when a graft polymer having an anchoring site to the pigment surface is produced by radical polymerization, known macromonomers can be used, and examples include macromonomers AA-6 (polymethyl methacrylate having a methacryloyl group as a terminal group), AS-6 (polystyrene having a methacryloyl group as a terminal group), AN-6S (a copolymer of styrene and acrylonitrile, having a methacryloyl group as a terminal group), and AB-6 (polybutyl acrylate having a methacryloyl group as a terminal group), all manufactured by Toagosei Co., Ltd.; PLACCEL FM5 (∈-caprolactone 5-mol equivalent adduct of 2-hydroxyethyl methacrylate) and FA10L (∈-caprolactone 10-mol equivalent adduct of 2-hydroxyethyl acrylate), all manufactured by Daicel Corp.; and the polyester-based macromonomer described in JP-A No. H2-272009. Among these, a polyester-based macromonomer having excellent flexibility and solvophilicity is particularly preferred from the viewpoints of the dispersibility and dispersion stability of the pigment dispersion, and the developability exhibited by a colored composition using the pigment dispersion. Furthermore, a polyester-based macromonomer described in JP-A No. H2-272009 is most preferred.

Regarding the block polymer having an anchoring site to the pigment surface, the block polymers described in JP-A Nos. 2003-49110 and 2009-52010 and the like are preferred.

The pigment dispersant that can be used in the invention is available also as a commercially available product, and specific examples thereof include "DA-7301" manufactured by Kusumoto Chemicals, Ltd.; "DISPERBYK-101 (polyamidoamine phosphate), 107 (carboxylic acid ester), 110 (copolymer containing an acid group), 130 (polyamide), 161, 162, 163, 164, 165, 166, 170 (polymeric copolymer)", "BYK-P104, P105 (high molecular weight unsaturated polycarboxylic acid)", all manufactured by BYK Chemie GmbH; "EFKA4047, 4050-4010-4165 (polyurethane-based), EFKA4330-4340 (block copolymers), 4400-4402 (modified polyacrylate), 5010 (polyester amide), 5765 (high molecular weight polycarboxylic acid salt), 6220 (fatty acid polyester), 6745 (phthalocyanine derivative), 6750 (azo pigment derivative)", all manufactured by EFKA GmbH; "AJISPER PB821, PB822, PB880, PB881" manufactured by Ajinomoto Fine-Techno Co., Inc.; "FLOWLEN TG-710 (urethane oligomer)" "POLYFLOW No. 50E, No. 300 (acrylic copolymers)", all manufactured by Kyoeisha Chemical Co., Ltd.; "DISPARLON KS-860, 873SN, 874,#2150 (aliphatic polyvalent carboxylic acid), #7004 (polyether ester), DA-703-50, DA-705, DA-725", all manufactured by Kusumoto Chemicals, Ltd.; "DEMOL RN, N (naphthalenesulfonic acid-formalin polycondensate), MS, C, SN-B (aromatic sulfonic acid-formalin polycondensate)", "HOMOGENOL L-18 (polymeric polycarboxylic acid)", "EMULGEN 920, 930, 935, 985 (polyoxyethylene nonyl phenyl ether)", "ACETAMIN 86 (stearylamine acetate)", all manufactured by Kao Corp.; "SOLSPERSE 5000 (phthalocyanine derivative), 22000 (azo pigment derivative), 13240 (polyester amine), 3000, 17000, 27000 (polymer having a functional moiety at a terminal), 24000, 28000, 32000, 38500 (graft polymer)", all manufactured by Lubrizol Japan, Ltd.; "NIKKOL T106 (polyoxyethylene sorbitan monooleate), MYS-IEX (polyoxyethylene monostearate)", all manufactured by Nikko Chemicals Co., Ltd.; HINOACT T-8000E and the like manufactured by Kawaken Fine Chemicals Co., Ltd.; organosiloxane polymer KP341 manufactured by Shin-Etsu Chemical Co., Ltd.; "W001: cationic surfactant", nonionic surfactants such as polyoxyethylene lauryl ether, polyoxyethylene stearyl ether, polyoxyethylene oleyl ether, polyoxyethylene octyl phenyl ether, polyoxyethylene nonyl phenyl ether, polyethylene glycol dilaurate, polyethylene glycol distearate, and sorbitan fatty acid esters, anionic surfactants such as "W004, W005, W017", all manufactured by Yusho Co., Ltd.; "EFKA-46, EFKA-47, EFKA-47EA, EFKA POLYMER 100, EFKA POLYMER 400, EFKA POLYMER 401, EFKA POLYMER 450", all manufactured by Morishita & Co., Ltd.; and "DISPERSE AID 6, DISPERSE AID 8, DISPERSE AID 15, DISPERSE AID 9100", all manufactured by San Nopco, Ltd.; as well as "ADEKA PLURONIC L31, F38, L42, L44, L61, L64, F68, L72, P95, F77, P84, F87, P94, L101, P103, F108, L121, P-123", all manufactured by Adeka Corp.; and "IONET (trade name) S-20" manufactured by Sanyo Chemical Industries, Ltd.

One kind of these pigment dispersants may be used singly, or two or more kinds may be used in combination. According to the invention, it is particularly preferable to use a pigment derivative and a polymeric dispersant in combination. With respect to the pigment dispersant of the invention, an alkali-soluble resin may also be used in combination with a terminal-modified polymer having an anchoring site to the pigment surface, a graft polymer, or a block copolymer. Examples of the alkali-soluble resin include (meth)acrylic acid copolymers, itaconic acid copolymers, crotonic acid copolymers, maleic acid copolymers, partially esterified maleic acid copolymers, acidic cellulose derivatives having a carboxylic acid at a side chain, and resins obtained by modifying a polymer having a hydroxyl group with an acid anhydride; however, (meth)acrylic acid copolymers are particularly preferred. N-position-substituted maleimide monomer copolymers described in JP-A No. H10-300922, ether dimer copolymers described in JP-A No. 2004-300204, and the alkali-soluble resins containing polymerizable groups described in JP-A No. H7-319161 are also preferable.

The content of the pigment dispersant in the colored composition is preferably 1 part by mass to 80 parts by mass, more preferably 5 parts by mass to 70 parts by mass, and even more preferably 10 parts by mass to 60 parts by mass, relative to 100 parts by mass of the pigment.

Specifically, when a polymeric dispersant is to be used, the amount of use thereof is, on a mass basis, preferably in the range of 5 parts to 100 parts, and more preferably in the range of 10 parts to 80 parts, relative to 100 parts by mass of the pigment.

When a pigment derivative is used in combination, the amount of use of the pigment derivative is, on a mass basis, preferably in the range of 1 part to 30 parts, more preferably in the range of 3 parts to 20 parts, and particularly preferably in the range of 5 parts to 15 parts, relative to 100 parts by mass of the pigment.

<Polymerizable Compound>

The colored composition of the invention preferably includes at least one polymerizable compound. The polymerizable compound is, for example, a polymerizable compound having at least one ethylenically unsaturated double bond, and can be selected for use from known components that constitute compositions. Examples include the components described in paragraphs [0010] to [0020] of JP-A No. 2006-23696, and the components described in paragraphs [0027] to [0053] of JP-A No. 2006-64921.

Furthermore, a urethane addition polymerizable compound which is produced using an addition reaction of an isocyanate and a hydroxyl group is also preferable, and the urethane acrylates described in JP-A No. S51-37193, Japanese Patent Application Publication (JP-B) Nos. H2-32293, and H2-16765, and the urethane compounds having an ethylene oxide skeleton described in JP-B Nos. S58-49860, S56-17654, S62-39417, and S62-39418 are also preferable.

Other examples include polyfunctional acrylates or methacrylates, such as the polyester acrylates described in JP-A No. S48-64183, JP-B Nos. S49-43191 and S52-30490, and the epoxy acrylates obtained by allowing epoxy resins to react with (meth)acrylic acid. Furthermore, the compounds introduced as photocurable monomers and oligomers in Journal of the Adhesion Society of Japan, Vol. 20, No. 7, pp. 300-308 (1984) can also be used.

Specific examples thereof include pentaerythritol tri(meth)acrylate, pentaerythritol tetra(meth)acrylate, dipentaerythritol penta(meth)acrylate, dipentaerythritol hexa(meth)acrylate, tri((meth)acryloyloxyethyl) isocyanurate, EO-modification products of pentaerythritol tetra(meth)acrylate, EO-modification products of dipentaerythritol hexa(meth)acrylate. Preferred examples of commercially available products include NK ESTER A-TMMT, NK ESTER A-TMM-3, NK OLIGO UA-32P, NK OLIGO UA-7200 (all manufactured by Shin Nakamura Chemical Co., Ltd.);

ARONIX M-305, ARONIX M-306, ARONIX M-309, ARONIX M-450, ARONIX M-402, TO-1382 (all manufactured by Toagosei Co., Ltd.); V#802 (manufactured by Osaka Organic Chemical Industry, Ltd.); KAYARAD D-330, KAYARAD D-320, KAYARAD D-310, and KAYARAD DPHA (all manufactured by Nippon Kayaku Co., Ltd.).

One kind of these polymerizable compounds may be used singly, or two or more kinds may be used in combination.

The content of the polymerizable compound (in the case of two or more kinds, the total content) in the total solid content of the colored composition is preferably 10% by mass to 80% by mass, more preferably 15% by mass to 75% by mass, and particularly preferably 20% by mass to 60% by mass.

<Photopolymerization Initiator>

The colored composition of the invention preferably includes at least one photopolymerization initiator. There are no particular limitations on the photopolymerization initiator as long as the compound is capable of polymerizing the polymerizable compound, and it is preferable that the photopolymerization initiator be selected from the viewpoints of characteristics, initiation efficiency, absorption wavelength, availability, cost, and the like.

The photopolymerization initiator is a compound which is sensitized by exposure light and initiates and accelerates the polymerization of a polymerizable compound. A compound which responds to active light rays having a wavelength of 300 nm or greater, and initiates and accelerates the polymerization of a polymerizable compound is preferred. Furthermore, even for a photopolymerization initiator which does not directly respond to active light ray having a wavelength of 300 nm or greater, the photopolymerization initiator can be preferably used in combination with a photosensitizer.

Specific examples thereof include an oxime ester compound, an organic halogenated compound, an oxydiazole compound, a carbonyl compound, a ketal compound, a benzoin compound, an acridine compound, an organic peroxide, an azo compound, a coumarin compound, an azide compound, a metallocene compound, a hexaarylbiimidazole compound, an organic boric acid compound, a disulfonic acid compound, an onium salt compound, an acylphosphine (oxide), a benzophenone compound, an acetophenone compound, and derivatives thereof.

Among these, from the viewpoint of sensitivity, an oxime ester compound and a hexaarylbiimidazole compound are preferred.

Regarding the oxime ester compound, the compounds described in JP-A Nos. 2000-80068, 2001-233842, Japanese Patent Application National Publication (Laid-Open) No. 2004-534797, WO 2005/080337 A, WO 2006/018973 A, JP-A Nos. 2007-210991, 2007-231000, 2007-269779 and 2009-191061 and WO 2009/131189 can be used.

Specific examples include
2-(O-benzoyloxime)-1-[4-(phenylthio)phenyl]-1,2-butanedione,
2-(O-benzoyloxime)-1-[4-(phenylthio)phenyl]-1,2-pentanedione,
2-(O-benzoyloxime)-1-[4-(phenylthio)phenyl]-1,2-hexanedione,
2-(O-benzoyloxime)-1-[4-(phenylthio)phenyl]-1,2-heptanedione,
2-(O-benzoyloxime)-1-[4-(phenylthio)phenyl]-1,2-octanedione,
2-(O-benzoyloxime)-1-[4-(methylphenylthio)phenyl]-1,2-butanedione,
2-(O-benzoyloxime)-1-[4-(ethylphenylthio)phenyl]-1,2-butanedione,
2-(O-benzoyloxime)-1-[4-(butylphenylthio)phenyl]-1,2-butanedione,
1-(O-acetyloxime)-1-[9-ethyl-6-(2-methylbenzoyl)-9H-carbazol-3-yl]ethanone,
1-(O-acetyloxime)-1-[9-methyl-6-(2-methylbenzoyl)-9H-carbazol-3-yl]ethanone,
1-(O-acetyloxime)-1-[9-propyl-6-(2-methylbenzoyl)-9H-carbazol-3-yl]ethanone,
1-(O-acetyloxime)-1-[9-ethyl-6-(2-ethylbenzoyl)-9H-carbazol-3-yl]ethanone,
1-(O-acetyloxime)-1-[9-ethyl-6-(2-butylbenzoyl)-9H-carbazol-3-yl]ethanone,
2-(benzoyloxyimino)-1-[4-(phenylthio)phenyl]-1-octanone, and
2-(acetoxyimino)-4-(4-chlorophenylthio)-1-[9-ethyl-6-(2-methylbenzoyl)-9H-carbazol-3-yl]-1-butanone. However, the oxime ester compound is not limited to these examples.

Furthermore, in this invention, from the viewpoints of sensitivity, stability over time, and coloration at the time of post-heating, a compound represented by the following formula (1) is also suitable as the oxime-based compound.

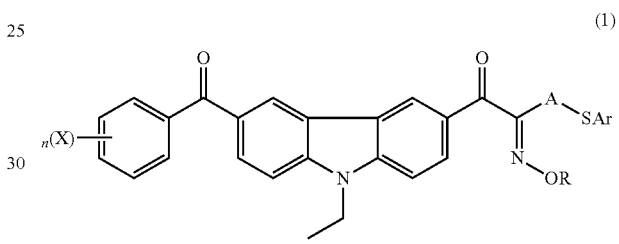

(1)

In formula (1), R and X each independently represent a monovalent substituent, A represents a divalent organic group, and Ar represents an aryl group. n represents an integer from 0 to 5.

In formula (1), R is preferably an acyl group from the viewpoint of high sensitivity, and specifically, an acetyl group, a propionyl group, a benzoyl group, and a toluoyl group are preferred.

In formula (1), from the viewpoint of increasing the sensitivity and suppressing coloration with the passage of heating time, A is preferably an unsubstituted alkylene group, an alkylene group substituted with an alkyl group (for example, a methyl group, an ethyl group, a tert-butyl group, or a dodecyl group), an alkylene group substituted with an alkenyl group (for example, a vinyl group or an allyl group), or an alkylene group substituted with an aryl group (for example, a phenyl group, a p-tolyl group, a xylyl group, a coumenyl group, a naphthyl group, an anthryl group, a phenanthryl group, or a styryl group).

In formula (1), Ar is preferably a substituted or unsubstituted phenyl group from the viewpoint of increasing the sensitivity and suppressing coloration with the passage of heating time. In the case of a substituted phenyl group, the substituent for the phenyl group is preferably a halogen atom such as a fluorine atom, a chlorine atom, a bromine atom, or an iodine atom.

In formula (1), from the viewpoint of enhancing the solvent solubility and the absorption efficiency in the longer wavelength region, X is preferably an alkyl group which may be substituted, an aryl group which may be substituted, an alkenyl group which may be substituted, an alkynyl group which may be substituted, an alkoxy group which may be substituted, an aryloxy group which may be substituted, an alkylthioxy group which may be substituted, an arylthioxy group which may be substituted, or an amino group which may be substituted.

n in formula (1) is preferably an integer of 1 or 2.

In formula (1), R and X each independently represent a monovalent substituent, A represents a divalent organic group, and Ar represents an aryl group. n represents an integer from 0 to 5.

Specific examples of the organic halogenated compound include compounds described in Wakabayashi et al., "Bull. Chem. Soc. Japan", 42, 2924 (1969); U.S. Pat. No. 3,905,815, JP-B No. S46-4605, JP-A Nos. S48-36281, S55-32070, S60-239736, S61-169835, S61-169837, S62-58241, S62-212401, S63-70243, S63-298339; M. P. Hutt, "Journal of Heterocyclic Chemistry" 1 (No. 3), (1970), and the like. Particularly, an oxazole compound or an s-triazine compound, both substituted with a trihalomethyl group, may be used.

Examples of the hexaarylbiimidazole compound include various compounds described in, for example, JP-B No. H6-29285, U.S. Pat. Nos. 3,479,185, 4,311,783, and 4,622,286, and specific examples include
2,2'-bis(o-chlorophenyl)-4,4',5,5'-tetraphenylbiimidazole,
2,2'-bis(o-bromophenyl)-4,4',5,5'-tetraphenylbiimidazole,
2,2'-bis(o,p-dichlorophenyl)-4,4',5,5'-tetraphenylbiimidazole,
2,2'-bis(o-chlorophenyl)-4,4',5,5'-tetra(m-methoxyphenyl) biimidazole,
2,2'-bis(o,o'-dichlorophenyl)-4,4',5,5'-tetraphenylbiimidazole,
2,2'-bis(o-nitrophenyl)-4,4',5,5'-tetraphenylbiimidazole,
2,2'-bis(o-methylphenyl)-4,4',5,5'-tetraphenylbiimidazole, and
2,2'-bis(o-trifluorophenyl)-4,4',5,5'-tetraphenylbiimidazole.

One kind of the photopolymerization initiator can be used singly or two or more kinds of the phoropolymerization initiators can be used in combination. Furthermore, when an initiator which does not have absorption at the exposure wavelength is used, it is necessary to use a sensitizer.

The total content of the photopolymerization initiator is preferably 0.5% to 30% by weight, more preferably 2% to 20% by weight, and most preferably 5% to 18% by mass, relative to the total solid content in the colored photosensitive resin composition. When the content is in this range, the sensitivity at the time of exposure is high, and the color characteristics are also good.

<Organic Solvent>

The colored composition of the invention can be configured to include an organic solvent.

There are essentially no particular limitations on the organic solvent as long as the solubility of the various components or the coatability of the colored composition is satisfied. However, it is particularly preferable that the organic solvent be selected in consideration of the solubility of the ultraviolet absorber, the alkali-soluble resin or the dispersant, coatability, and safety. Furthermore, when the colored composition according to the invention is prepared, it is preferable to incorporate at least two kinds of organic solvents.

Preferable examples of the organic solvent include: as esters, ethyl acetate, n-butyl acetate, isobutyl acetate, amyl formate, isoamyl acetate, isobutyl acetate, butyl propionate, isopropyl butyrate, ethyl butyrate, butyl butyrate, methyl lactate, ethyl lactate, and alkyl oxyacetates (for example, methyl oxyacetate, ethyl oxyacetate, butyl oxyacetate (for example, methyl methoxyacetate, ethyl methoxyacetate, butyl methoxyacetate, methyl ethoxyacetate, and ethyl ethoxyacetate)), 3-oxypropionic acid alkyl esters (for example, methyl 3-oxypropionate, and ethyl 3-oxypropionate (for example, methyl 3-methoxypropionate, ethyl 3-methoxypropionate, methyl 3-ethoxypropionate, and ethyl 3-ethoxypropionate)), 2-oxypropionic acid alkyl esters (for example, methyl 2-oxypropionate, ethyl 2-oxypropionate, and propyl 2-oxypropionate (for example, methyl 2-methoxypropionate, ethyl 2-methoxypropionate, propyl 2-methoxypropionate, methyl 2-ethoxypropionate, and ethyl 2-ethoxypropionate)), methyl 2-oxy-2-methylpropionate and ethyl 2-oxy-2-methylpropionate (for example, methyl 2-methoxy-2-methylpropionate and ethyl 2-ethoxy-2-methylpropionate), methyl pyruvate, ethyl pyruvate, propyl pyruvate, methyl acetoacetate, ethyl acetoacetate, methyl 2-oxobutanoate, and ethyl 2-oxobutanoate; as ethers, diethylene glycol dimethyl ether, tetrahydrofuran, ethylene glycol monomethyl ether, ethylene glycol monoethyl ether, methyl cellosolve acetate, ethyl cellosolve acetate, diethylene glycol monomethyl ether, diethylene glycol monoethyl ether, diethylene glycol monobutyl ether, propylene glycol monomethyl ether, propylene glycol monomethyl ether acetate, propylene glycol monoethyl ether acetate, propylene glycol monopropyl ether acetate, methyl 3-ethoxypropionate, and ethyl 3-ethoxypropionate; as ketones, methyl ethyl ketone, cyclohexanone, 2-heptanone, 3-heptanone; and as aromatic hydrocarbons, toluene and xylene.

It is also preferable to mix two or more kinds of these organic solvents from the viewpoints of the solubility of the ultraviolet absorber and the alkali-soluble resin, and an improvement of the coated surface. In this case, the organic solvent is particularly preferably a mixed solution composed of two or more kinds selected from methyl 3-ethoxypropionate, ethyl 3-ethoxypropionate, ethyl cellosolve acetate, ethyl acetate, diethylene glycol dimethyl ether, butyl acetate, methyl 3-methoxypropionate, 2-heptanone, cyclohexanone, ethyl carbitol acetate, butyl carbitol acetate, propylene glycol methyl ether, and propylene glycol methyl ether acetate.

The content of the organic solvent in the colored composition is preferably an amount such that the total solid concentration of the composition is 5% by mass to 80% by mass, more preferably 5% by mass to 60% by mass, and particularly preferably 10% by mass to 50% by mass, from the viewpoint of coatability.

<Other Components>

The colored composition of the invention may further include, in addition to the various components described above, other components such as an alkali-soluble binder and a crosslinking agent to the extent that the effects of the invention are not impaired.

(Alkali-Soluble Binder)

The alkali-soluble binder is not particularly limited as long as it has alkali solubility, and can be preferably selected from the viewpoints of heat resistance, developability, availability and the like.

It is preferable that The alkali-soluble binder be a linear organic high molecular weight polymer and be soluble in organic solvents and developable with a weakly alkaline aqueous solution. Examples of such a linear organic high molecular weight polymer include polymers having a carboxylic acid at a side chain, for example, methacrylic acid copolymers, acrylic acid copolymers, itaconic acid copolymers, crotonic acid copolymers, maleic acid copolymers, and partially esterified maleic acid copolymers described in JP-A No. S59-44615, JP-B Nos. S54-34327, S58-12577, and S54-25957, and JP-A Nos. S59-53836, and S59-71048. Similarly, acidic cellulose derivatives having a carboxylic acid at a side chain are useful.

In addition to the compounds mentioned above, a product obtained by adding an acid anhydride to a polymer having a hydroxyl group, or a polyhydroxystyrene-based resin, a polysiloxane-based resin, a poly(2-hydroxyethyl (meth)acrylate), polyvinylpyrrolidone, polyethylene oxide, polyvinyl alcohol, and the like are also useful as the alkali-soluble binder according to the invention. The linear organic high molecular weight polymer may be a product obtained by copolymerizing monomers that are hydrophilic. Examples thereof include alkoxy alkyl (meth)acrylate, hydroxyalkyl (meth)acrylate, glycerol (meth)acrylate, (meth)acrylamide, N-methylolacrylamide, secondary or tertiary alkyl acrylamide, dialkylaminoalkyl (meth)acrylate, morpholine (meth) acrylate, N-vinylpyrrolidone, N-vinylcaprolactam, vinylimidazole, vinyltriazole, methyl (meth)acrylate, ethyl (meth) acrylate, branched or straight-chained propyl (meth)acrylate, branched or straight-chained butyl (meth)acrylate, and phenoxyhydroxypropyl (meth)acrylate. In addition to those, monomers containing a tetrahydrofurfuryl group, a phosphoric acid group, a phosphoric acid ester group, a quaternary ammonium salt group, an ethyleneoxy chain, a propyleneoxy chain, a sulfonic acid group and a group derived from a salt thereof, a morpholinoethyl group or the like are also useful as the monomers that are hydrophilic.

Furthermore, the alkali-soluble binder may have a polymerizable group in a side chain in order to enhance the crosslinking efficiency, and for example, polymers containing an allyl group, a (meth)acryl group, an allyloxyalkyl group or the like in side chains are also useful. Examples of the polymers containing the polymerizable groups mentioned above include commercially available DIANAL NR series (manufactured by Mitsubishi Rayon Co., Ltd.); PHOTOMER 6173 (COOH group-containing polyurethane acrylic oligomer, manufactured by Diamond Shamrock Co., Ltd.); VISCOAT R-264 and KS RESIST 106 (all manufactured by Osaka Organic Chemical Industry, Ltd.); CYCLOMER P Series and PLACCEL CF200 Series (all manufactured by Daicel Chemical Industries, Ltd.), and EBECRYL 3800 (manufactured by Daicel-Cytec Co., Ltd.). Furthermore, in order to increase the strength of the cured coating film, alcohol-soluble nylon, a polyether of 2,2-bis(4-hydroxyphenyl) propane and epichlorohydrin, and the like are also useful.

Among these various alkali-soluble binders, from the viewpoint of heat resistance, a polyhydroxystyrene-based resin, a polysiloxane-based resin, an acrylic resin, an acrylamide-based resin, and an acryl/acrylamide copolymer resin are preferred; and from the viewpoint of the control of developability, an acrylic resin, an acrylamide-based resin, and an acryl/acrylamide copolymer resin are preferred.

Preferred examples of the acrylic resin include copolymers formed from monomers selected from benzyl (meth)acrylate, (meth)acrylic acid, hydroxyethyl (meth)acrylate, and (meth) acrylamide; commercially available DIANAL NR series (manufactured by Mitsubishi Rayon Co., Ltd.), KS RESIST 106 (manufactured by Osaka Organic Chemical Industry, Ltd.); CYCLOMER P Series and PLACCEL CF200 Series (all manufactured by Daicel Chemical Industries, Ltd.).

From the viewpoints of developability, liquid viscosity, and the like, the alkali-soluble binder is preferably a polymer having a weight average molecular weight (value measured by a GPC method and calculated relative to polystyrene standards) of 1000 to $2 \times 10^5$, more preferably a polymer having a weight average molecular weight of 2000 to $1 \times 10^5$, and particularly preferably a polymer having a weight average molecular weight of 5000 to $5 \times 10^4$. One kind of the alkali-soluble binders may be used singly, or two or more kinds of the alkali soluble binders may be used in combination.

(Crosslinking Agent)

When a crosslinking agent is complementarily used in the colored composition of the invention, the hardness of a colored cured film formed by curing the colored composition can be further increased.

There are no particular limitations on the crosslinking agent as long as the agent can achieve film curing by a crosslinking reaction, and examples thereof include (a) an epoxy resin, (b) a melamine compound, a guanamine compound, a glycoluril compound or a urea compound, all of which are substituted with at least one substituent selected from a methylol group, an alkoxymethyl group, and an acyloxymethyl group; and (c) a phenol compound, a naphthol compound, or a hydroxyanthracene compound, all of which are substituted with at least one substituent selected from a methylol group, an alkoxymethyl group, and an acyloxymethyl group. Among them, a polyfunctional epoxy resin is preferred.

For the details on specific examples of the crosslinking agent and the like, reference can be made to the description of paragraphs [0134] to [0147] of JP-A No. 2004-295116.

(Polymerization Inhibitor)

The colored composition of the invention may include a polymerization inhibitor.

The polymerization inhibitor is a substance which takes the role of conducting hydrogen donation (or hydrogen-giving), energy donation (or energy-giving), electron donation (or electron-giving) or the like, on a polymerization initiating species, such as a radical, that has generated in a colored photosensitive resin composition under the action of light or heat, to deactivate the polymerization initiating species, and suppress unintended initiation of polymerization. The polymerization inhibitors described in paragraphs [0154] to [0173] of JP-A No. 2007-334322, and the like can be used.

Among these, preferred examples of the polymerization inhibitor include p-methoxyphenol.

The content of the polymerization inhibitor in the colored composition of the invention is preferably 0.0001% by mass to 5% by mass, more preferably 0.001% by mass to 5% by mass, and particularly preferably 0.001% by mass to 1% by mass, relative to the total mass of the polymerizable compound.

(Surfactant)

The colored photosensitive resin composition of the invention may include a surfactant.

Regarding the surfactant, any of anionic, cationic, nonionic and amphoteric surfactants can be used, but a preferred surfactant is a nonionic surfactant. Specific examples include the nonionic surfactants described in paragraph [0058] of JP-A No. 2009-098616, and among them, fluorine-based surfactants are preferred.

Examples of other surfactants that can be used in the invention include commercially available products such as MEGAFACE F142D, MEGAFACE F172, MEGAFACE F173, MEGAFACE F176, MEGAFACE F177, MEGAFACE F183, MEGAFACE F479, MEGAFACE F482, MEGAFACE F554, MEGAFACE F780, MEGAFACE F781, MEGAFACE F781-F, MEGAFACE R30, MEGAFACE R08, MEGAFACE F-4725F, MEGAFACE BL20, MEGAFACE R-61, MEGAFACE R-90 (manufactured by DIC Corp.); FLUORAD FC-135, FLUORAD FC-170C, FLUORAD FC-430, FLUORAD FC-431, NOVEC FC-4430 (manufactured by Sumitomo 3M, Ltd.); ASAHI GUARD AG7105, 7000, 950, 7600, SURFLON S-112, SURFLON S-113, SURFLON S-131, SURFLON S-141, SURFLON S-145, SURFLON S-382, SURFLON SC-101, SURFLON SC-102, SURFLON SC-103, SURFLON SC-104, SURFLON SC-105, SURFLON SC-106 (manufactured by Asahi Glass Co., Ltd.);

EFTOP EF351, EFTOP 352, EFTOP 801, EFTOP 802 (manufactured by Mitsubishi Materials Electronic Chemicals Co., Ltd.); and FTERGENT 250 (manufactured by Neos Co., Ltd.).

Preferred example of the surfactant include a copolymer which includes a constituent unit A and a constituent unit B as shown in the following formula (1), and has a weight average molecular weight (Mw), as measured by gel permeation chromatography using tetrahydrofuran as a solvent and calculated relative to polystyrene standards, of from 1,000 to 10,000.

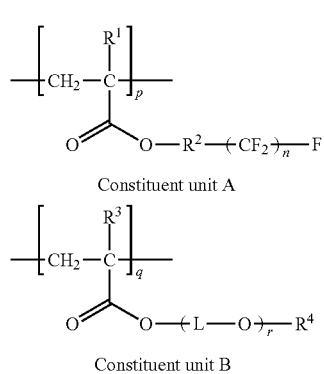

(1)

Constituent unit A

Constituent unit B wherein in formula (1), $R^1$ and $R^3$ each independently represent a hydrogen atom or a methyl group; $R^2$ represents a straight-chain alkylene group having from 1 to 4 carbon atoms; $R^4$ represents a hydrogen atom or an alkyl group having from 1 to 4 carbon atoms; L represents an alkylene group having from 3 to 6 carbon atoms; p and q each represent weight percentage that represents a polymerization ratio, while p represents a numerical value of from 10% by mass to 80% by mass, and q represents a numerical value of from 20% by mass to 90% by mass; r represents an integer from 1 to 18; and n represents an integer from 1 to 10.

L is preferably a branched alkylene group represented by the following formula (2). $R^5$ in formula (2) represents an alkyl group having from 1 to 4 carbon atoms, and from the viewpoints of compatibility and wettability to the surfaces to be coated, $R^5$ is preferably an alkyl group having from 1 to 3 carbon atoms, and more preferably an alkyl group of 2 or 3 carbon atoms. The sum of p and q (p+q) is preferably such that p+q=100, that is, 100% by mass.

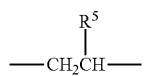

(2)

The weight average molecular weight (Mw) of the copolymer is more preferably from 1,500 to 5,000.

One kind of these surfactants can be used singly, or two or more kinds can be used in combination. The amount of addition of the surfactant in the colored composition of the invention is preferably 0.01% by mass to 2.0% by mass, and particularly preferably 0.02% by mass to 1.0% by mass, in the solid content. When the amount of addition is in this range, satisfactory coatability and uniformity of the cured film are obtained.

(Adhesion Improving Agent)

The colored composition of the invention may include an adhesion improving agent.

The adhesion improving agent is a compound which enhances adhesiveness between a cured film and an inorganic material that constitutes the base material, for example, glass, silicon, silicon compounds such as silicon oxide and silicon nitride, gold, copper, or aluminum. Specific examples include silane coupling agents and thiol-based compounds. The silane coupling agent as an adhesion improving agent is intended to modify the interface, and any known compounds can be used without particular limitations.

Regarding the silane coupling agent, those silane coupling agents described in paragraph [0048] of JP-A No. 2009-98616 are preferred, and among them, γ-glycidoxypropyltrialkoxysilane and γ-methacryloxypropyltrialkoxysilane are more preferred. These can be used singly, or two or more kinds can be used in combination.

The content of the adhesion improving agent in the colored composition of the invention is preferably 0.1% by mass to 20% by mass, and more preferably 0.2% by mass to 5% by mass, relative to the total solid content.

(Sensitizer)

The colored composition of the invention may further include a sensitizer. Typical sensitizers that can be used in the invention include those compounds disclosed in J. V. Crivello, Adv. in Polymer Sci., 62, 1 (1984). Specific examples include pyrene, perylene, acridine, thioxanthone, 2-chlorothioxanthone, benzoflavin, N-vinylcarbazole, 9,10-dibutoxyanthracene, anthraquinone, benzophenone, coumarin, ketocoumarin, phenanthrene, camphor-quinone, and phenothiazine derivatives. The sensitizer is preferably added at a proportion of 50% by mass to 200% by mass based on the photopolymerization initiator.

(Chain Transfer Agent)

The colored composition of the invention can further include a chain transfer agent.

Examples of the chain transfer agent that can be used in the invention include N,N-dialkylaminobenzoic acid alkyl esters such as N,N-dimethylaminobenzoic acid ethyl ester; mercapto compounds containing a heterocyclic ring, such as 2-mercaptobenzothiazole, 2-mercaptobenzoxazole, 2-mercaptobenzimidazole, N-phenylmercaptobenzimidazole, and 1,3,5-tris(3-mercaptobutyloxyethyl)-1,3,5-triazine-2,4,6-(1H,3H,5H)trione; and aliphatic polyfunctional mercapto compounds such as pentaerythritol tetrakis(3-mercaptobutyrate) and 1,4-bis(3-mercaptobutyryloxy)butane.

The chain transfer agents may be used singly, or two or more kinds may be used in combination.

It is preferable that the amount of addition of the chain transfer agent be in the range of 0.01% by mass to 15% by mass relative to the total solid content of the composition of the invention from the viewpoint of reducing the fluctuation of sensitivity, and the amount of addition is more preferably 0.1% by mass to 10% by mass, and particularly preferably 0.5% by mass to 5% by mass.

(Development Accelerating Agent)

In the case of accelerating alkali-solubility in an unexposed region and promoting a further improvement in the developability of the colored composition, a development accelerating agent may also be added. The development accelerating agent is preferably a low molecular weight organic carboxylic acid compound having a molecular weight of 1000 or less, or a low molecular weight phenol compound having a molecular weight of 1000 or less.

Specific examples include aliphatic monocarboxylic acids such as formic acid, acetic acid, propionic acid, butyric acid, valeric acid, pivalic acid, caproic acid, diethylacetic acid, enanthoic acid, and caprylic acid; aliphatic dicarboxylic acids such as oxalic acid, malonic acid, succinic acid, glutaric acid, adipic acid, pimelic acid, suberic acid, azelaic acid, sebacic acid, brassylic acid, methylmalonic acid, ethylmalonic acid, dimethylmalonic acid, methylsuccinic acid, tetramethylsuccinic acid, and citraconic acid; aliphatic tricarboxylic acids such as tricarballylic acid, aconitic acid, and camphoronic acid; aromatic monocarboxylic acids such as benzoic acid, toluic acid, cumic acid, hemellitic acid, and mesitylenic acid; aromatic polycarboxylic acids such as phthalic acid, isophthalic acid, terephthalic acid, trimellitic acid, trimesic acid, mellophanic acid, and pyromellitic acid; phenylacetic acid, hydroatropic acid, hydrocinnamic acid, mandelic acid, phenylsuccinic acid, atropic acid, cinnamic acid, methyl cinnamate, benzyl cinnamate, cinnamylidene acetic acid, coumaric acid, and umbellic acid.

(Other Additives)

In the colored composition, various other additives, for example, a filler, an oxidation inhibitor, an ultraviolet absorber, and an aggregation preventing agent, can be incorporated as necessary. Examples of these additives include agents described in paragraphs [0155] to of JP-A No. 2004-295116.

The colored composition of the invention can include a photostabilizer described in paragraph [0078] of JP-A No. 2004-295116.

<Preparation of Colored Composition>

There are no particular limitations on the mode of preparation of the colored composition of the invention, but for example, the colored composition can be prepared by mixing the components described above such as a compound represented by formula (I) or a tautomer thereof, a polymerizable compound, and a photopolymerization initiator, and as necessary, optional components.

Meanwhile, in the preparation of the colored composition, the components to be included in the colored composition may be mixed all at once. Alternatively, each the components may be dissolved/dispersed in a solvent, and then added in sequence. There are no particular restrictions on the order of introduction when mixing the components, and on the operation conditions. For example, the composition may be prepared dissolving/dispersing all the components simultaneously in a solvent. The composition may also be prepared preparing two or more solutions/dispersion liquids using the components beforehand, and mixing these solutions/dispersion at the time of use (at the time of application).

In the preparation of the colored composition according to the invention, for the purpose of removing foreign matters or reducing defects, it is preferable to mix the components, and then filtering the mixture with a filter. Regarding the filter, any of those conventionally used for filtering applications and the like may be used without particular limitations. Specific examples include filters formed using fluororesins such as PTFE (polytetrafluoroethylene); polyamide-based resins such as nylon-6 and nylon-6,6; and polyolefin resins (including high density, ultrahigh molecular weight resins) such as polyethylene and polypropylene (PP). Among these filter materials, polyamide-based resins such as nylon-6 and nylon-6,6; and polypropylenes (including high density polypropylene) are preferred.

The pore size of the filter is suitably about 0.01 μm to about 7.0 μm, preferably about 0.01 μm to about 2.5 μm, and more preferably about 0.01 μm to about 2.0 μm. When the pore size is set to this range, fine foreign matters that inhibit the preparation of a uniform colored composition in the subsequent processes are reliably removed, and the formation of a uniform and smooth colored composition is enabled.

When a filter is used, different filters may be used in combination. In that case, filtering using a first filter may be carried out only once, or may be carried out two or more times. The first filtering may be carried out using a first filter formed combining plural filters having a pore size different from each other in the range described above. Regarding the pore size as used herein, the nominal values provided by filter manufacturers can be referred to. Regarding commercially available filters, the filter can be selected from various filters supplied by, for example, Pall Corp., Advantec Toyo Kaisha, Ltd., Entegris Japan, Inc. (formerly, Microlith Japan, Inc.), Kitz Micro Filter Corp., and the like.

Regarding a second filter, a filter formed from the same material as that of the first filter described above can be used.

For example, filtering with the first filter may be carried out only for a pigment dispersion, and after other components are incorporated into the pigment dispersion to obtain a colored composition, second filtering may be carried out.

The colored composition of the invention can be applied to color filters for solid-state imaging devices, color filters for liquid crystal display devices, printing inks, inkjet inks, and the like.

Particularly, a colored cured film obtained by curing the colored composition of the invention has high color purity, gives a high extinction coefficient when formed into a thin layer, and has excellent fastness properties and voltage retention ratio. Therefore, the colored cured film is useful for the formation of color pixels in color filters for solid-state imaging devices and color filters for liquid crystal display devices. Furthermore, when the colored cured film is applied to a color filter that is included in a liquid crystal display device, an excellent voltage retention ratio can be obtained when a voltage is applied.

<<Color Filter and Method for Producing the Same>>

The color filter of the invention has a structure including a colored region (colored cured film) that has been formed using the colored composition of the invention, disposed on a support.

The colored region on the support is constituted to include, for example, colored films of red (R), green (G), blue (B), and the like, that constitute pixels of the color filter.

The color filter of the invention may be formed by any method, as long as it is a method capable of forming a patterned colored region (colored cured film) which contains a compound represented by formula (I) or a tautomer thereof and are cured. The color filter of the invention is preferably produced using the method for producing a color filter of the invention.

The method for producing a color filter of the invention includes a colored layer-forming process of applying the colored composition of the invention onto a support to form a colored layer formed from the colored composition; and a colored cured film forming process of exposing the formed colored layer in a pattern form and developing the colored layer to form a patterned colored cured film.

Hereinafter, processes in the production method of the invention are described.

The color filter of the invention is configured to include a substrate, and provided on the substrate, a colored region containing a compound represented by formula (I) or a tautomer thereof as a dye compound. The colored region on the substrate is constituted to include, for example, colored films of, for example, red (R), green (G), and blue (B), which constitute pixels of the color filter. Since the color filter of the invention includes a dipyrromethene-metal complex compound having a predetermined structure, the color filter has clear coloring and high contrast when the color filter is used for image display, and is particularly suitable for a liquid crystal display device.

The color filter of the invention may be formed by any method, as long as it is a method capable of forming a patterned colored cured film which contains a dipyrromethene-metal complex compound and is cured. Preferably, the color filter is produced using the colored composition of the invention.

The method for producing a color filter of the invention includes process (A) of applying the colored composition described above onto a support to form a colored layer (also referred to as colored composition layer); and process (B) of exposing the colored composition layer formed in process (A) in a pattern form (preferably, through a mask) and developing and removing uncured areas of the coating film using a developer liquid to form colored regions (colored pattern). When these processes are carried out, a colored pattern composed of pixels of various colors (three colors or four colors) is formed, and thus a color filter can be obtained. Furthermore, in the method for producing a color filter of the invention, an embodiment further including process (C) of irradiating the colored pattern formed in process (B) with ultraviolet radiation; and process (D) of performing a heating treatment on the colored pattern that has been irradiated with ultraviolet radiation in process (C), is particularly preferred.

When such a method is used, color filters that are used in liquid crystal display devices or solid-state imaging devices can be produced at high quality and at low cost, with less process-related difficulties.

Hereinafter, the method for producing a color filter of the invention are described more specifically.

—Process (A)—

In the method for producing a color filter of the invention, first, the colored composition of the invention as described above is applied by a desired coating method, onto a support directly or with another layer interposed therebetween, a coating film (colored composition layer) formed from the colored composition is formed, and thereafter, if necessary, preliminary curing (prebake) is carried out to dry the colored composition layer.

Examples of the support include alkali-free glass, soda glass, PYREX (registered trademark) glass, and quartz glass, which are used in liquid crystal display devices, products obtained by attaching transparent conductive films on any of these glass plates, and photo-electric conversion device substrates that are used in solid-state imaging devices, for example, silicon substrates or plastic substrates. Furthermore, on each of these supports, a black matrix that separates various pixels may be formed, or a transparent resin layer may be provided to promote adhesion or the like. Also, if necessary, an undercoat layer may be provided on the support for the purpose of improving the adhesion to upper layers, preventing the diffusion of materials, or flattening the surface.

Furthermore, it is preferable that a plastic substrate have a gas barrier layer and/or a solvent resistant layer on the surface.

In addition to this, a color filter can also be produced by using, as a support, a driving substrate in which a thin film transistor (TFT) of a thin film transistor (TFT) type color liquid crystal display device is arranged, and forming a colored pattern formed using the colored composition of the invention, on this drive substrate.

Examples of the substrate material for TFT type liquid crystal driving substrates include glass, silicone, polycarbonates, polyesters, aromatic polyamides, polyamideimides, and polyimides. These substrates may be subjected to appropriate pretreatments such as a chemical treatment using a silane coupling agent or the like, a plasma treatment, ion plating, sputtering, a gas phase reaction method, and vacuum deposition, as desired. For example, a substrate in which a passivation film such as a silicon nitride film is formed on the surface of a TFT type liquid crystal driving substrate can be used.

A coating film of a colored composition can be formed by applying the colored composition of the invention on a substrate by a coating method such as rotary coating, slit coating, flow cast coating, roll coating, bar coating, or inkjetting, directly or with another layer interposed therebetween.

In the process A, there are no particular limitations on the method of coating the colored composition of the invention onto a substrate, but methods of using slit nozzles, such as a slit-and-spin method and a spinless coating method (hereinafter, referred to as slit nozzle coating methods) are preferred.

In regard to the slit nozzle coating methods, in the slit-and-spin coating method and the spinless coating method, the conditions may vary depending on the size of the substrate to be coated; however, for example, when a fifth generation glass substrate (1100 mm×1250 mm) is coated by the spinless coating method, the amount of ejection of the colored composition from slit nozzles is usually 500 microliters/second to 2000 microliters/second, and preferably 800 microliters/second to 1500 microliters/second. Furthermore, the coating speed is usually 50 mm/second to 300 mm/second, and preferably 100 mm/second to 200 mm/second.

Furthermore, the solid content of the colored composition that is used in the coating process is usually 10% to 20%, and preferably 13% to 18%.

In the process A, usually a prebake treatment is applied after coating. According to necessity, a vacuum treatment can be applied before the prebake. The conditions for vacuum drying are such that the degree of vacuum is usually about 0.1 torr to 1.0 torr, and preferably 0.2 ton to 0.5 torr.

Regarding the conditions for prebake, conditions of heating at 70° C. to 130° C. for about 0.5 minutes to 15 minutes using a hot plate or an oven may be employed.

Furthermore, the thickness of the colored composition layer formed using the colored composition is appropriately selected according to the purpose. In a color filter for liquid crystal display devices, the thickness is preferably in the range of 0.2 μm to 5.0 μm, more preferably in the range of 1.0 μm to 4.0 μm, and most preferably in the range of 1.5 μm to 3.5 μm. Furthermore, in a color filter for solid-state imaging devices, the thickness is preferably in the range of 0.2 μm to 5.0 μm, more preferably in the range of 0.3 μm to 2.5 μm, and most preferably in the range of 0.3 μm to 1.5 μm.

Meanwhile, the thickness of the colored composition layer is the film thickness after the prebake.

—Process (B)—

Subsequently, in the method for producing a color filter of the invention, the coating film formed from a colored composition (colored composition layer) that has been formed on a support as described above is subjected to exposure through, for example, a photomask. The light or radiation that can be applied to exposure is preferably g-line, h-line, i-line, j-line, KrF light, or ArF light, and particularly preferably i-line. In the case of using i-line as the irradiation light, it is preferable to irradiate the coating film at an exposure dose of 100 mJ/cm$^2$ to 10,000 mJ/cm$^2$.

Furthermore, regarding other examples of the exposure light, various mercury lamps of ultrahigh pressure, high pressure, medium pressure and low pressure, chemical lamps, carbon arc lamps, xenon lamps, metal halide lamps, various laser light sources of visible and ultraviolet radiation, fluorescent lamps, tungsten lamps, solar light and the like can also be used.

Exposure Process Using Laser Light Source

Regarding an exposure method using a laser light source, it is preferable to use an ultraviolet light laser as the light source.

The irradiated light is preferably ultraviolet laser light having a wavelength in the range of 300 nm to 380 nm, and more preferably, ultraviolet laser light having a wavelength in the range of 300 nm to 360 nm is preferred from the viewpoint that the wavelength coincides with the exposure wavelength of the resist. Specifically, the third harmonic wave of Nd:YAG laser (355 nm), which is a relatively inexpensive solid laser having a high power output, or XeCl (308 nm) or XeF (353 nm) of excimer lasers can be suitably used.

The exposure dose for the object to be exposed (pattern) is in the range of 1 $mJ/cm^2$ to 100 $mJ/cm^2$, and more preferably in the range of 1 $mJ/cm^2$ to 50 $mJ/cm^2$. When the exposure dose is in this range, it is preferable from the viewpoint of the productivity of pattern formation.

There are no particular limitations on the exposure apparatus, but commercially available examples that can be used include CALLISTO (manufactured by V-Technology Co., Ltd.), EGIS (manufactured by V-Technology Co., Ltd.), and DF2200G (manufactured by Dainippon Screen Manufacturing Co., Ltd.). Apparatuses other than those described above are also preferably used.

When a color filter for liquid crystal display devices is produced, exposure using mainly h-line or i-line by means of a proximity exposure machine, or a mirror projection exposure machine, is preferably used. Furthermore, when a color filter for solid-state imaging devices is produced, it is preferable to use mainly i-line with a stepper exposure machine. Meanwhile, regarding the photomask used when a color filter is produced using a TFT type liquid crystal driving substrate, a photomask in which a pattern for forming pixels (colored pattern) as well as a pattern for forming through-holes or U-shaped depressions are provided may be used.

The colored composition layer that has been exposed in the above-described manner can be heated.

Furthermore, exposure can be carried out while allowing nitrogen gas to flow into the chamber, in order to suppress oxidative discoloration of the color material in the colored composition layer.

Subsequently, the colored composition layer after exposure is subjected to development with a developer liquid. Thereby, a negative type or positive type colored pattern (resist pattern) can be formed. In the development process, uncured areas of the coating film after exposure are dissolved out with the developer liquid, and only cured portions are made to remain on the substrate.

Regarding the developer liquid, any developer liquid can be used as long as it dissolves the coating film of the colored composition (colored composition layer) in uncured areas, and does not dissolve cured areas. For example, a combination of various organic solvents, or an alkaline aqueous solution can be used.

Examples of the organic solvents used for development include the solvents can be used in the preparation of the colored composition of the invention as described above.

The alkaline aqueous solution may be, for example, an alkaline aqueous solution prepared by dissolving an alkaline compound such as sodium hydroxide, potassium hydroxide, sodium carbonate, sodium hydrogen carbonate, sodium silicate, sodium metasilicate, aqueous ammonia, ethylamine, diethylamine, dimethylethanolamine, tetramethylammonium hydroxide, tetraethylammonium hydroxide, choline, pyrrole, piperidine, or 1,8-diazabicyclo[5,4,0]-7-undecene, so as to attain a concentration of 0.001% by mass to 10% by mass, and preferably 0.01% by mass to 1% by mass. When the developer liquid is an alkaline aqueous solution, it is preferable to adjust the alkali concentration so as to attain, preferably, pH of 11 to 13, and more preferably pH of 11.5 to 12.5.

In the alkaline aqueous solution, for example, a water-soluble organic solvent such as methanol or ethanol, a surfactant, and the like can be added in appropriate amounts.

The developing temperature is usually 20° C. to 30° C., and the developing time is usually 20 seconds to 90 seconds.

Developing may be carried out by any of a dipping method, a shower method, a spray method or the like, and these may also be combined with a swing method, a spin method, an ultrasonic method or the like. If the surface to be developed is wetted in advance with water or the like before being brought into contact with the developer liquid, development unevenness can be prevented. Furthermore, developing can also be carried out by slanting the substrate.

In the case of producing a color filter for solid-state imaging devices, paddle development may be used.

After the developing treatment, a rinsing treatment of washing and removing the excess developer liquid is carried out, the color composition layer is dried, and then in order to complete curing, a heat treatment (post-bake) is carried out.

The rinsing treatment is usually carried out using pure water, but for the purpose of saving, a method of using pure water for the final washing while using used pure water is used in the early stage of washing, or a method of washing the substrate in a slanting position or using ultrasonic irradiation in combination may also be used.

After the rinsing treatment, after removing water and drying are carried out, a heating treatment at about 200° C. to 250° C. is usually carried out. This heating treatment (post-bake) can be carried out on the coating film after development, using a heating means such as a hot plate, a convection oven (hot air circulating dryer), or a high frequency wave heater under the conditions described above, in a continuous mode or a batch mode.

The processes described above are carried out for each color and repeated in sequence in accordance with the desired number of colors, whereby a color filter in which cured colored films of a plural number of colors (colored pattern) are formed, can be produced.

Since the color filter of the invention has high contrast, less color density unevenness, and good color characteristics, the color filter can be suitably used in solid-state imaging devices or liquid crystal display devices.

—Process (C)—

In the method for producing a color filter of the invention, particularly, the colored pattern (pixels) formed using the colored composition can be subjected to post-exposure by ultraviolet irradiation.

—Process (D)—

It is preferable that the colored pattern that has been subjected to post-exposure by ultraviolet irradiation as described above be further subjected to a heating treatment. When the colored pattern thus formed is subjected to a heating treatment (so-called post-bake treatment), the colored pattern can be further cured. This heating treatment can be carried out, for example, using a hot plate, a heater, or a oven.

The temperature at the time of the heating treatment is preferably 100° C. to 300° C., and more preferably 150° C. to 250° C. The heating treatment is preferably about 10 minutes to 120 minutes.

The colored pattern obtained as described above constitutes the pixels in the color filter. In regard to the production of a color filter having pixels of a plural number of colors, the process (A) and process (B) described above, and optionally the process (C) or process (D) may be repeated in accordance with the desired number of colors.

The process (C) and/or process (D) may be carried out every time the formation, exposure and development of a colored composition layer of a single color are completed (for each color). The process (C) and/or process (D) may be carried out all at once after the formation, exposure and development of all the colored composition layers of the desired number of colors are completed.

Since the color filter obtained by the method for producing a color filter of the invention (color filter of the invention) uses the colored composition of the invention, the color filter has clear coloring and high contrast when the color filter is used for image display, and exhibits excellent fastness properties and voltage retention ratio.

The color filter of the invention can be used in a liquid crystal display device or a solid-state imaging device, and is particularly suitable for the use in liquid crystal display devices. When the color filter is used in a liquid crystal display device, since a dye is used as a colorant, display of images having excellent spectroscopic characteristics and contrast is enabled while good hues are achieved, and an excellent voltage retention ratio is also obtained.

Regarding the use of the colored composition of the invention, the use is explained for the formation of a colored pattern of a color filter is mainly explained in the above; however, the colored composition can also be applied to the formation a black matrix that separates the colored pattern (pixels) that constitute a color filter.

The black matrix on the substrate can be formed by using a colored composition containing a processed pigment of a black pigment such as carbon black or titanium black, carrying out the various processes of coating, exposure and development, and then performing post-bake as necessary.

<<Liquid Crystal Display Device>>

The liquid crystal display device of the invention includes the color filter of the invention described above.

When the color filter of the invention is used in a liquid crystal display device, while the liquid crystal display device includes a metal complex coloring material having excellent spectroscopic characteristics and heat resistance, the voltage retention ratio does not decrease when a voltage is applied, there are fewer alignment defects of the liquid crystal molecules that come along with a decrease in the specific resistance, and the display images have good color tones and excellent display characteristics.

Therefore, a liquid crystal display device equipped with the color filter of the invention can display high quality images having good color tones of the display images and excellent display characteristics.

The definition of the display apparatus and the details of various display apparatuses are described in, for example, "Electronic Display Devices (written by Akio Sasaki, published by Kogyo Chosakai Publishing Co., Ltd. in 1990)", and "Display Devices (written by Sumiaki Ibuki, published by Sangyo Tosho Publishing Co., Ltd. in 1988)". Furthermore, in regard to the liquid crystal display device, the details are described in, for example, "Jisedai Ekisho Disupurei Gijutsu (Next-Generation Liquid Crystal Display Technologies) (edited by Tatsuo Uchida, published by Kogyo Chosakai Publishing Co., Ltd. in 1994)". There are no particular limitations on the liquid crystal display device to which the invention can be applied, and the invention can be applied to liquid crystal display devices of various modes that are described in, for example, "Jisedai Ekisho Disupurei Gijutsu (Next-Generation Liquid Crystal Display Technologies)".

The color filter according to the invention may also be used in liquid crystal display devices of the color TFT mode. In regard to the liquid crystal display devices of the color TFT mode, the details are described in, for example, "Color TFT Liquid Crystal Display (published by Kyoritsu Shuppan Co., Ltd. in 1996)". Furthermore, the invention can also be applied to liquid crystal display devices with increased viewing angles, such as the horizontal electric field drive mode such as IPS, or the pixel division mode such as MVA; or can also be applied even to STN, TN, VA, OCS, FFS and R-OCB.

The color filter according to the invention can also be subjected to the bright, high-definition COA (color-filter on array) mode. In the liquid crystal display device of the COA mode, regarding the characteristics required of the color filter layer, the characteristics required of an interlayer insulating film, that is, low dielectric constant and resistance to stripping liquid, may be required, in addition the conventionally required characteristics such as described above. In regard to the color filter of the invention, since a dye having excellent hue is used, the color filter has good color purity, light permeability, and the like, and since the colored pattern (pixels) has excellent color tones, a liquid crystal display device of the COA mode having high resolution and excellent long-term durability can be provided. Meanwhile, in order to satisfy the required characteristics of low dielectric constant, a resin coating film may be provided on the color filter layer.

In regard to these image display modes, for example, the details are described in page 43 of "EL, PDP, LCD Disupurei—Gijutsu to Shijo no Saishin Doukou (EL, PDP and LCD Displays—Latest Trend of Technologies and Markets) (published by Toray Research Center, Investigation Research Section in 2001)", and the like.

A liquid crystal display device equipped with the color filter according to the invention is configured to include various members such as an electrode substrate, a polarizing film, a retardation film, a backlight, a spacer, and a viewing angle compensation film, in addition to the color filter according to the invention. The color filter of the invention can be applied to a liquid crystal display device composed of these known members. In regard to these members, the details are described in, for example, "94 Markets of Peripheral Materials and Chemicals for Liquid Crystal Displays (Kentaro Shima, published by CMC Corp. in 1994)", and "2003 Current Status and Future Prospects of Liquid Crystal-Related Market (Second Volume) (Omote Ryokichi, published by Fuji Chimera Research Institute, Inc. in 2003)".

In regard to the backlight, the details are described in SID Meeting Digest 1380 (2005) (A. Konno, et al.); Monthly Display, December issue, 2005, pages 18 to 24 (Yasuhiro Shima); ibid., pages 25 to 30 (Takaaki Yagi), and the like.

When the color filter according to the invention is used in a liquid crystal display device, a high contrast can be realized when the color filter is combined with a three-wavelength tube of a conventionally known cold cathode tube, and as LED light sources of red green and blue (RGB-LED) are used backlights, a liquid crystal display device having high luminance and good color reproducibility with high color purity can be obtained.

<<Solid-State Imaging Device>>

The solid-state imaging device of the invention includes the color filter of the invention described above. The configuration of the solid-state imaging device of the invention is not particularly limited as long as it is a configuration in which the color filter of the invention is included, and which can function as a solid-state imaging device. For example, a configuration such as follows may be used.

It is a configuration which includes, on a support, plural photodiodes that constitute the light-receiving areas of a solid-state imaging device (a CCD image sensor, a CMOS image sensor or the like) and a transport electrode formed from polysilicone and the like; includes, on the photodiodes and the transport electrode, a light-shielding film formed from tungsten and the like and having openings corresponding to the light-receiving areas of the photodiodes; includes, on the light-shielding film, a device-protecting film formed from silicon nitride and the like, which is formed so as to cover the entire surface of the light-shielding film and the light-receiving areas of the photodiodes; and includes, on the device-protecting film, the color filter of the invention.

A configuration which includes a light collecting means (for example, a microlens or the like; hereinafter, the same applies) above the device-protecting layer and below the color filter (side closer to the support), or a configuration which includes a light collecting means on the color filter may also be employed.

EXAMPLES

Hereinafter, the present invention will be described more specifically by way of Examples, but the invention is not intended to be limited the following Examples as long as the gist is maintained. Meanwhile, unless particularly stated otherwise, the units "parts" and "percent (%)" are on a mass basis.

Example 1

Synthesis of Dipyrromethene-metal Complex Compound

Exemplary Compound A-1 described above of the dipyrromethene-metal complex compound of the invention was synthesized according to the following reaction scheme A. In addition, Exemplary Compound B-1 was also synthesized according to the following reaction scheme A.

Reaction Scheme A

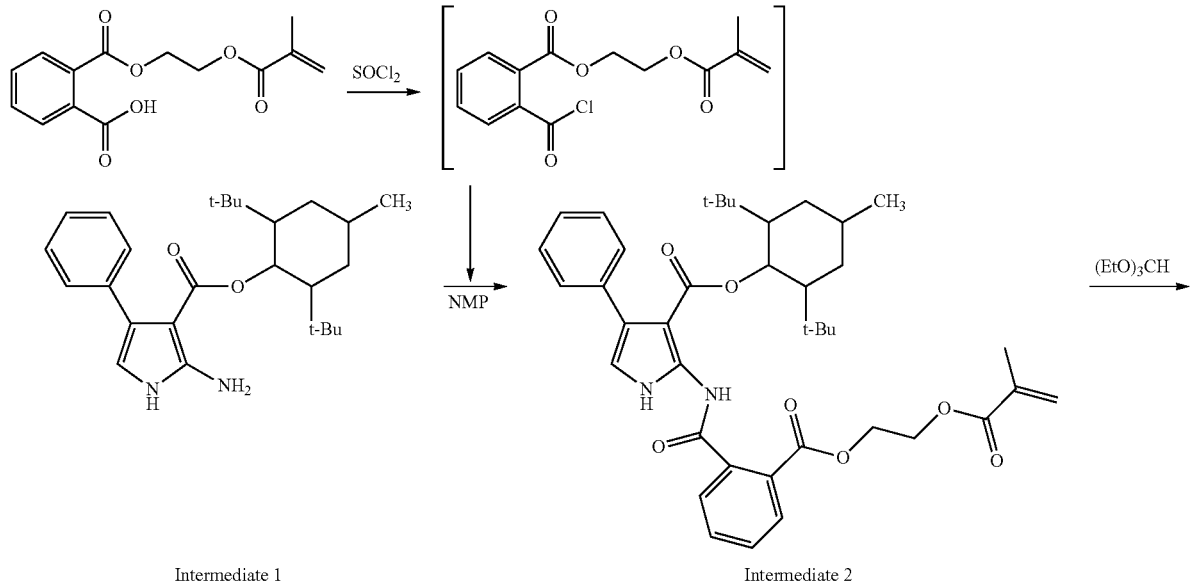

Intermediate 1                    Intermediate 2

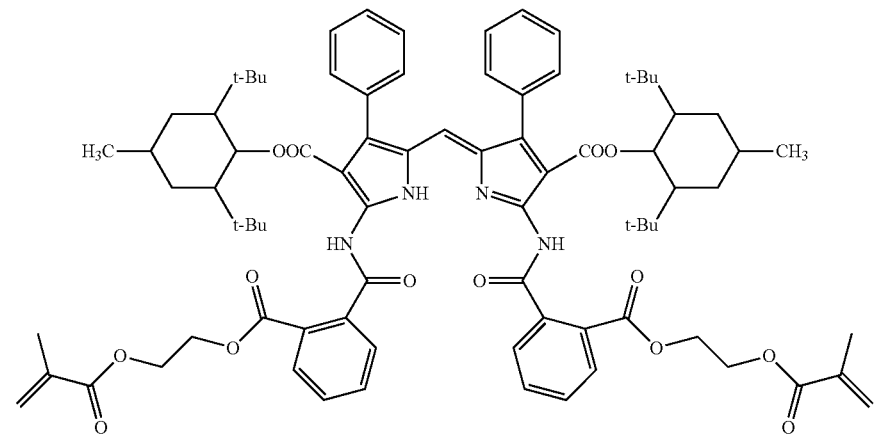

Intermediate 3

Intermediate 3 + Zn(OAc)₂•H₂O ⟶

-continued

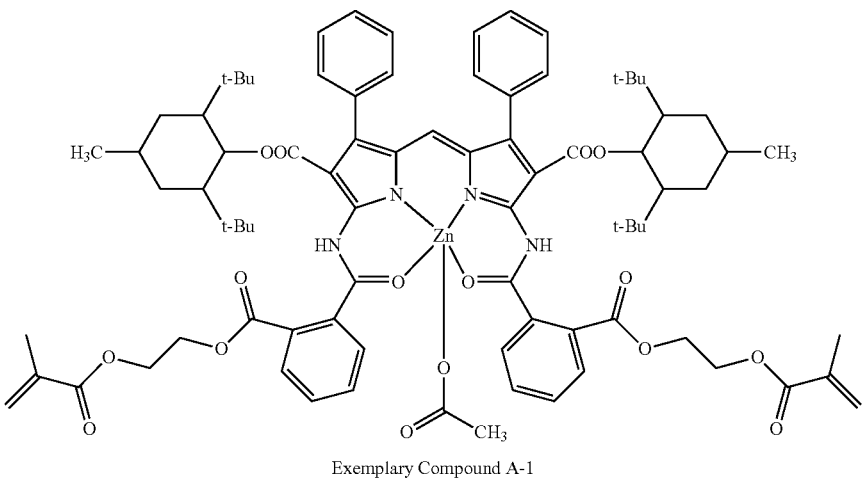

Exemplary Compound A-1

Intermediate 1 was synthesized by the method described in U.S. Patent Application Publication No. 2008/0076044. Intermediate 2, Intermediate 3, and Exemplary Compound A-1 were synthesized as described below.

(Synthesis of Intermediate 2)

40.7 g (0.14 mol) of 2-methacryloyloxyethylphthalic acid was added to 60 ml of N-methylpyrrolidone, and the mixture was stirred in an ice bath. 17.3 g (0.14 mol) of thionyl chloride was added dropwise to this solution, and the mixture was stirred for one hour in an ice bath and for another one hour at room temperature. Thus, an acid halide solution was obtained.

100 ml of N-methylpyrrolidone was added to 49.2 g (0.12 mol) of Intermediate 1 obtained by the method described in U.S. Patent Application Publication No. 2008/0076044, and the mixture was stirred under ice cooling. Subsequently, the solution described above was added dropwise thereto. Thereafter, the mixture was stirred for 1 hour under ice cooling and for another 3 hours at room temperature.

After completion of the reaction, the reaction liquid was dissolved in 500 ml of ethyl acetate, and the solution was purified by liquid-liquid separation with 500 ml of water. The organic layer was dried over sodium sulfate and then filtered, and the filtrate was concentrated under reduced pressure. A solid thus obtained was washed with acetonitrile, and was dried. In this manner, 65 g (yield: 81%) of Intermediate 2 was obtained.

Furthermore, the details of $^1$H-NMR (CDCl$_3$) measured for the Intermediate 2 thus obtained are as follows. δ: 11.04 (s, 1H), 10.86 (s, 1H), 7.92 (d, 1H), 7.72-7.35 (m, 9H), 6.35 (s, 1H), 6.11 (s, 1H), 5.82 (s, 1H), 5.56 (s, 1H), 4.58 (m, 2H), 4.42 (m, 2H), 1.95 (s, 3H), 1.27-1.12 (m, 4H), 1.06-0.92 (m, 2H), 0.84 (s, 18H), 0.70 (d, 3H), 0.63-0.47 (m, 2H).

(Synthesis of Intermediate 3)

33.5 g (0.05 mol) of Intermediate 2 and 3.7 g (0.025 mol) of triethyl ortho-formate were added to 50 ml of acetic anhydride, and the mixture was stirred at room temperature. 75 ml of trifluoroacetic acid was added dropwise to this solution, and the mixture was stirred for 5 hours at room temperature. After completion of the reaction, the reaction liquid was poured into a solution obtained by adding 112 g of sodium hydrogen carbonate to 170 ml of ethyl acetate and 750 ml of water, and the mixture was stirred for one hour. Subsequently, a precipitate was filtered. The solid thus obtained was purified by silica gel chromatography using a solution of hexane/ethyl acetate=5/1, and thus 13.5 g (40%) of Intermediate 3 was obtained.

Furthermore, the details of $^1$H-NMR (CDCl$_3$) measured for the Intermediate 3 thus obtained are as follows. δ: 11.08 (s, 2H), 7.92 (m, 4H), 7.39-7.13 (m, 14H), 6.15 (s, 1H), 6.02 (s, 2H), 5.98 (s, 2H), 5.44 (s, 2H), 4.56 (m, 4H), 4.40 (m, 4H), 1.95 (s, 6H), 1.30-1.08 (m, 8H), 0.98-0.92 (m, 4H), 0.84 (m, 36H), 0.65 (d, 6H), 0.50-0.35 (m, 4H).

(Synthesis of Exemplary Compound A-1)

6.8 g (0.005 mol) of Intermediate 3 was added to 50 ml of tetrahydrofuran, and the mixture was stirred at room temperature. To this liquid, a liquid obtained by adding 1.3 g (0.006 mol) of zinc acetate dihydrate to 25 ml of methanol was added, and the mixture was stirred for 3 hours. Thereafter, the reaction liquid and a precipitated solid were filtered, and the material thus obtained was added to 150 ml of methanol. The resulting mixture was stirred for one hour. Thereafter, the mixture as concentrated under reduced pressure, and a solid thus obtained was purified by silica gel chromatography. In this manner, 5.2 g (70%) of Exemplary Compound A-1 was obtained.

Furthermore, the details of $^1$H-NMR (CDCl$_3$) measured for the Exemplary Compound A-1 thus obtained are as follows. δ: 11.38 (s, 2H), 7.93 (t, 4H), 7.71-7.52 (m, 4H), 7.32-7.10 (m, 12H), 6.28 (s, 1H), 6.08 (s, 2H), 5.80 (s, 2H), 5.53 (s, 2H), 4.43 (m, 4H), 4.25 (m, 4H), 1.86 (s, 6H), 1.22 (m, 6H), 0.98 (d, 4H), 0.88 (s, 36H), 0.64 (d, 6H), 0.52 (m, 2H), 0.28 (m, 2H).

Furthermore, for the compounds thus obtained, the molar extinction coefficient (∈) in an ethyl acetate solution was measured using a spectrophotometer, UV-1800PC (manufactured by Shimadzu Corp.). Furthermore, the absorbance (Abs) at the maximum absorption wavelength ($\lambda_{max}$) was normalized as 1.0, and the absorbance at 450 nm was evaluated.

The maximum absorption wavelength $\lambda_{max}$ of the Exemplary Compound A-1 was 556 nm, and the molar extinction coefficient (∈) was 88,000. Furthermore, the results of the absorbance (Abs value), maximum absorption wavelength $\lambda_{max}$, and molar extinction coefficient (∈) are presented in Table 1.

Example 2

Furthermore, exemplary compounds (dipyrromethene-metal complex compounds or tautomers thereof) indicated in the following Table 1 were synthesized by methods similar to the reaction scheme according to Example 1, and also, identification by the same method as in Example 1, and measurement of the maximum absorption wavelength $\lambda_{max}$ and the molar extinction coefficient ($\in$) were carried out. The measurement results are presented in the following Table 1 together with the results for the Exemplary Compound A-1 obtained in Example 1.

TABLE 1

| Exemplary compound | λmax(nm) | ϵ | Abs value at 450 nm (*1) |
|---|---|---|---|
| A-1 | 88000 | 556 | 0.030 |
| A-2 | 101000 | 562 | 0.042 |

TABLE 1-continued

| Exemplary compound | λmax(nm) | ϵ | Abs value at 450 nm (*1) |
|---|---|---|---|
| A-4 | 94000 | 566 | 0.055 |
| A-5 | 96000 | 565 | 0.054 |
| A-6 | 110000 | 557 | 0.033 |
| A-8 | 90000 | 556 | 0.024 |
| A-13 | 87000 | 556 | 0.034 |
| A-15 | 98000 | 559 | 0.030 |
| B-1 | 96000 | 566 | 0.062 |
| B-2 | 90000 | 552 | 0.048 |
| C-1 | 102000 | 558 | 0.042 |
| C-3 | 101000 | 556 | 0.028 |
| D-1 | 96000 | 560 | 0.042 |

(*1): Abs value at 450 nm that has been normalized with respect to Abs at $\lambda_{max}$ = 1.0

From the results of Table 1, it was found that the compound of the invention is a compound which has a high molar extinction coefficient ($\in$) and a low absorbance at 450 nm, is excellent in color separation, and is suitable for color filters.

Hereinafter, specific examples for preparing a colored composition and a color filter will be described.

Example 3

First, the various components used in the preparation of the colored composition are described below.

(S-1) A pigment dispersion liquid obtained by mixing 12.8 parts of C.I. Pigment Blue 15:6 and 7.2 parts of an acrylic pigment dispersant with 80.0 parts of propylene glycol monomethyl ether acetate, and sufficiently dispersing the pigment using a bead mill.

(T-1) Polymerizable compound: KAYARAD DPHA (manufactured by Nippon Kayaku Co., Ltd.; dipentaerythritol hexaacrylate)

(U-1) Alkali-soluble binder: A propylene glycol monomethyl ether acetate solution (solid content: 40.0%) of a benzyl methacrylate/methacrylic acid (75/25 [mass ratio]) copolymer (weight average molecular weight: 12,000)

(V-1) Photopolymerization initiator: 2-(Benzoyloxyimino)-1-[4-(phenylthio)phenyl]-1-octanone (V-2) Photopolymerization initiator: 2-(Acetoxyimino)-4-(4-chlorophenylthio)-1-[9-ethyl-6-(2-methylbenzoyl)-9H-carbazol-3-yl]-1-butanone (W-1) Sensitizer: 4,4'-Bis(diethylamino)benzophenone (X-1) Organic solvent: Propylene glycol monomethyl ether acetate (X-2) Organic solvent: Ethyl 3-ethoxypropionate (Y-1) Surfactant: MEGAFACE F781-F (manufactured by DIC Corp.)

—B1. Preparation of Colored Composition (Coating Liquid)—

The components in the following composition were mixed, and thus Colored Composition 1 was prepared.

<Composition>

| | |
|---|---|
| Exemplary Compound A-1 (dipyrromethene-metal complex compound) | 6.9 parts |
| Pigment dispersion liquid: (S-1) described above | 43.0 parts |
| Polymerizable compound: (T-1) described above | 103.4 parts |
| Alkali-soluble binder: (U-1) described above | 212.2 parts (based on solid content: 84.9 parts) |
| Photopolymerization initiator: (V-1) described above | 21.2 parts |
| Sensitizer: (W-1) described above | 3.5 parts |
| Organic solvent: (X-1) described above | 71.9 parts |
| Organic solvent: (X-2) described above | 3.6 parts |
| Surfactant: (Y-1) described above | 0.06 parts |

—B2. Production of Color Filter Using Colored Composition, and Evaluation—

The colored composition (color resist liquid) obtained in the above section B1 was applied on a glass substrate (1737, manufactured by Corning) having a size of 100 mm×100 mm such that the x value which serves as an index of the color density would be 0.150, and the colored composition was dried for 60 seconds in an oven at 90° C. (prebake). Thereafter, the applied composition was exposed at 200 mJ/cm² (illuminance: 20 mW/cm²) using a high pressure mercury lamp, through a photomask having a mask hole width of 10 μm to 100 μm for resolution evaluation, and the coating film obtained after exposure was developed with a 1% aqueous solution of an alkali developer liquid, CDK-1 (manufactured by Fujifilm Electronics Materials Co., Ltd.). Pure water was sprayed in a shower form to wash away the developer liquid. Then, the coating film that had been subjected to exposure and development as described above was subjected to heating treatment for one hour in an oven at 220° C. (post-bake), and thus a patterned colored cured film (colored layer) for a color filter was formed on a glass substrate. Thus, a colored filter substrate 1 (Color Filter 1) was produced.

—Evaluation—

Color Filter 1 thus obtained was subjected to evaluations described below. The evaluation results are presented in the following Table 2.

<1. Light Resistance>

The Color Filter 1 was irradiated for 20 hours at 50,000 lux (corresponding to 1,000,000 lux·h) with a xenon lamp as a light resistance test, and then the ΔE*ab value of the color difference between before and after the light resistance test was measured. A smaller value of the ΔE*ab value indicates better light resistance.

—Determination criteria—

5: ΔE*ab value <3
4: 3 ≤ΔE*ab value <5
3: 5 ≤ΔE*ab value <10
2: 10 ≤ΔE*ab value <20
1: 20 ≤ΔE*ab value <2. Luminance>

The luminance of the Color Filter 1 was measured using a microspectroscopic analyzer manufactured by Olympus Corp., OSP-SP200, and the luminance was evaluated based on Y value. A higher Y value indicates better performance as a color filter for liquid crystal display.

<3. Contrast>

The Color Filter 1 thus obtained was interposed between two sheets of polarizing films, and the values of luminance in the case where the polarization axes of the two sheets of polarizing films were parallel to each other, and in the case where the polarization axes were perpendicular to each other, were measured using a color luminance meter (manufactured by Topcon Corp., product No.: BM-5A). The luminance in the case where the polarization axes of the two sheets of polarizing films were parallel to each other was divided by the luminance in the case where the polarization axes were perpendicular to each other, and the value thus obtained as determined as contrast. A higher contrast indicates better performance as a color filter for liquid crystal display.

—Determination Criteria—

5: The contrast is 20,000 or higher
4: The contrast is higher than or equal to 15,000 and lower than 20,000
3: The contrast is higher than or equal to 10,000 and lower than 15,000
2: The contrast is higher than or equal to 5,000 and lower than 10,000
1: The contrast is lower than 5,000

<4. Voltage Retention Ratio>

The colored composition was applied on an ITO electrode-attached glass substrate (product name: 1737, manufactured by Corning) such that the film thickness after being dried would be 2.0 μm, and the film was dried (prebake) for 60 seconds in an oven at 90° C. Thereafter, the coating film was exposed at 100 mJ/cm$^2$ (the illuminance was 20 mW/cm$^2$) without using a mask, and was developed at 25° C. using a 1% aqueous solution of an alkali developer liquid (product name: CDK-1, manufactured by Fujifilm Electronics Materials Co., Ltd.). The coating film obtained after washing with water and drying was subjected to a heating treatment (post-bake) for 30 minutes in an oven at 230° C., and thus a colored cured film was formed. Next, the substrate on which this colored cured film was formed and a substrate on which only an ITO electrode was deposited in a predetermined form were bonded together with a sealing agent mixed with 5-μm glass beads, and then liquid crystal MJ971189 (product name) manufactured by Merck was injected between the substrates. Thus, a liquid crystal cell was produced.

Next, the liquid crystal cell was inserted in a constant temperature bath at 70° C. for 48 hours, and then the voltage retention ratio of the liquid crystal cell was measured under the measurement conditions described below, using a liquid crystal voltage retention ratio measurement system, VHR-1A type (product name) manufactured by Toyo Technica, Inc. The voltage retention ratio was evaluated on the basis of the scores indicated in the following criteria. A higher score indicates better voltage retention ratio.

Measurement Conditions
Distance between electrodes: 5 μm to 15 μm
Applied voltage pulse amplitude: 5 V
Applied voltage pulse frequency: 60 Hz
Applied voltage pulse width: 16.67 msec

*Voltage retention ratio: Liquid crystal cell potential difference after 16.7 milliseconds/value of voltage applied at 0 milliseconds

*Determination
90% or more: 5
85% to less than 90%: 4
80% to less than 85%: 3
75% to less than 80%: 2
less than 75%: 1

Example 4 to Example 15

Colored Composition 2 to Colored Composition 13 were prepared in the same manner as in Example 3, except that Exemplary Compound A-1 used in the preparation of the Colored Composition 1 of Example 3 was changed to the above-described exemplary compounds (dipyrromethene-metal complex compounds) indicated in Table 1, respectively, and the ratio of the exemplary compound and the pigment dispersion liquid (S-1) was adjusted so as to adjust the chromaticity of the composition to that of Colored Composition 1 of Example 3. Subsequently, Color Filter 2 to Color Filter 13 were produced.

Evaluations were carried out in the same manner as in Example 3, using the Colored Composition 2 to Colored Composition 13 and Color Filter 2 to Color Filter 13. The results are presented in Table 2.

Example 16

Colored Composition 14 was prepared by mixing the components of the composition described below as in the manner of Example 3, and Color Filter 14 was obtained in the same manner as in Example 3, except that the Colored Composition 14 was used instead of the Colored composition 1.

Evaluations were carried out in the same manner as in Example 3, using the Colored Composition 14 and Color Filter 14. The results are presented in Table 2.

—Composition—

| | |
|---|---|
| Exemplary Compound A-1 | 6.9 parts |
| Pigment dispersion liquid: (S-1) described above | 43.0 parts |
| Polymerizable compound: (T-1) described above | 103.4 parts |
| Alkali-soluble binder: (U-1) described above | 212.2 parts (based on solid content: 84.9 parts) |
| Photopolymerization initiator: (V-2) described above | 21.2 parts |
| Sensitizer: (W-1) described above | 3.5 parts |
| Organic solvent: (X-1) described above | 71.9 parts |
| Organic solvent: (X-2) described above | 3.6 parts |
| Surfactant: (Y-1) described above | 0.06 parts |

Examples 17 to 19

Colored Composition 15 to Colored Composition 17 were prepared in the same manner as in Example 16, except that the Exemplary Compound A-1 used in the preparation of the Colored Composition 14 of Example 16 was changed to the above-described exemplary compounds (dipyrromethene-metal complex compounds) indicated in Table 2, respectively, and the ratio of the exemplary compound and the pigment dispersion liquid (S-1) was adjusted so as to adjust the chromaticity of the obtained composition to that of the Colored Composition 14 of Example 16. Subsequently, Color Filter 15 to Color Filter 17 were obtained.

Evaluations were carried out in the same manner as in Example 3, using the Colored Composition 15 to Colored Composition 17 and Color Filter 15 to Color Filter 17. The results are presented in Table 2.

Example 20

Colored Composition 18 was prepared by mixing the components of the composition described below as in the manner of Example 3, and Color Filter 18 was obtained in the same manner as in Example 3, except that the Colored Composition 18 was used instead of the Colored composition 1.

Evaluations were carried out in the same manner as in Example 3, using the Colored Composition 18 and Color Filter 18. The results are presented in Table 2.

—Composition—

| | |
|---|---|
| Exemplary Compound A-1 | 4.7 parts |
| Pigment dispersion liquid: (S-1) described above | 42.1 parts |
| Compound (5) described below | 2.3 parts |
| Polymerizable compound: (T-1) described above | 103.4 parts |
| Alkali-soluble binder: (U-1) described above | 212.2 parts (based on solid content: 84.9 parts) |
| Photopolymerization initiator: (V-2) described above | 21.2 parts |
| Sensitizer: (W-1) described above | 3.5 parts |
| Organic solvent: (X-1) described above | 71.9 parts |
| Organic solvent: (X-2) described above | 3.6 parts |
| Surfactant: (Y-1) described above | 0.06 parts |

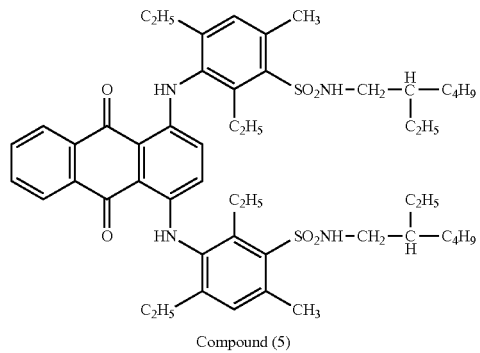

Compound (5)

The compound (5) is a diaminoanthraquinone compound represented by formula (X) described above.

Example 21

Colored Composition 19 was prepared by replacing the Exemplary Compound A-1 with Exemplary Compound B-1 in the preparation of colored Composition 18 of Example 20, and Color Filter 19 was obtained in the same manner as in Example 20, except that the Colored Composition 19 was used instead of the Colored composition 18.

Evaluations were carried out in the same manner as in Example 3, using the Colored Composition 19 and Color Filter 19. The results are presented in Table 2.

Comparative Example 1 to Comparative Example 4

Colored Composition 101 to Colored Composition 104 were prepared in the same manner as in the preparation of Colored Composition 1 of Example 3, except that the Exemplary Compound A-1 was changed to Comparative Compound 1 to Comparative Compound 4 indicated in Table 2, respectively, and the ratio of the comparative compound and the pigment dispersion liquid (S-1) was adjusted so as to adjust the chromaticity of the obtained composition to that of Colored Composition 1 of Example 3. Subsequently, Color Filter 101 to Color Filter 104 were obtained in the same manner as in Example 3, except that Colored Composition 101 to Colored Composition 104 were used instead of the Colored Composition 1.

Evaluations were carried out in the same manner as in Example 3, using the Colored Composition 101 to Colored Composition 104 and Color Filter 101 to Color Filter 104. The results are presented in Table 2.

Meanwhile, the details of the Comparative Compound 1 to Comparative Compound 4 are as follows.

Comparative Compound 1: C.I. Acid Violet 17

Comparative Compound 2: C.I. Acid Violet 49

Comparative Compound 3: (Compound III-1 described in U.S. Patent Application Publication No. 2008/0076044)

Comparative Compound 4: (Compound H-12 described in JP-A No. 2010-84141)

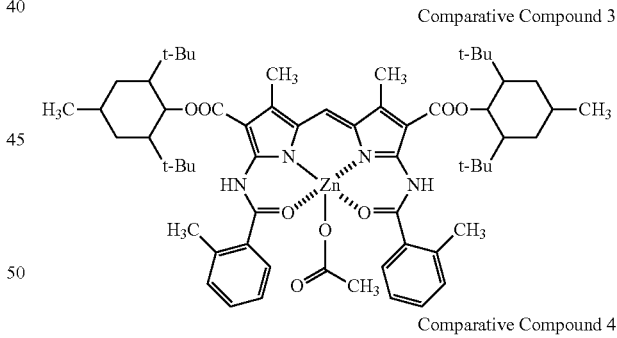

Comparative Compound 3

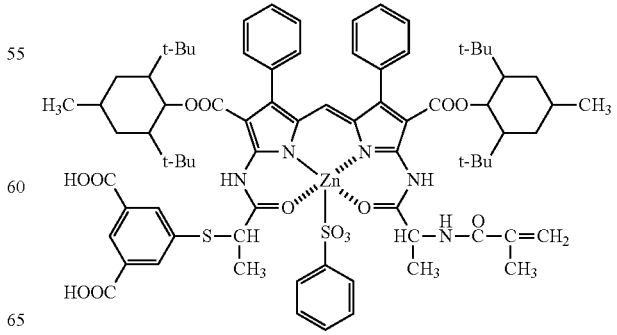

Comparative Compound 4

TABLE 2

| Example | Exemplary compound or comparative compound | Colored composition | Color filter | Light resistance | Y value | Contrast | Voltage retention ratio |
|---|---|---|---|---|---|---|---|
| Example 3 | A-1 | Colored Composition 1 | Color Filter 1 | 5 | 10.8 | 5 | 5 |
| Example 4 | A-2 | Colored Composition 2 | Color Filter 2 | 4 | 10.7 | 4 | 5 |
| Example 5 | A-4 | Colored Composition 3 | Color Filter 3 | 4 | 10.3 | 4 | 5 |
| Example 6 | A-5 | Colored Composition 4 | Color Filter 4 | 5 | 10.2 | 4 | 5 |
| Example 7 | A-6 | Colored Composition 5 | Color Filter 5 | 4 | 10.8 | 5 | 5 |
| Example 8 | A-8 | Colored Composition 6 | Color Filter 6 | 5 | 10.9 | 4 | 5 |
| Example 9 | A-13 | Colored Composition 7 | Color Filter 7 | 5 | 10.5 | 4 | 5 |
| Example 10 | A-15 | Colored Composition 8 | Color Filter 8 | 5 | 10.9 | 4 | 5 |
| Example 11 | B-1 | Colored Composition 9 | Color Filter 9 | 4 | 10.3 | 4 | 5 |
| Example 12 | B-2 | Colored Composition 10 | Color Filter 10 | 4 | 10.5 | 5 | 5 |
| Example 13 | C-1 | Colored Composition 11 | Color Filter 11 | 5 | 10.5 | 4 | 4 |
| Example 14 | C-3 | Colored Composition 12 | Color Filter 12 | 5 | 10.9 | 4 | 4 |
| Example 15 | D-1 | Colored Composition 13 | Color Filter 13 | 4 | 10.5 | 4 | 5 |
| Example 16 | A-1 | Colored Composition 14 | Color Filter 14 | 5 | 10.9 | 5 | 5 |
| Example 17 | A-2 | Colored Composition 15 | Color Filter 15 | 4 | 10.8 | 4 | 5 |
| Example 18 | A-13 | Colored Composition 16 | Color Filter 16 | 4 | 10.5 | 4 | 5 |
| Example 19 | B-1 | Colored Composition 17 | Color Filter 17 | 5 | 10.5 | 4 | 5 |
| Example 20 | A-1 | Colored Composition 18 | Color Filter 18 | 5 | 10.8 | 5 | 5 |
| Example 21 | B-1 | Colored Composition 19 | Color Filter 19 | 5 | 10.4 | 5 | 5 |
| Comparative Example 1 | Comparative Compound 1 | Colored Composition 101 | Color Filter 101 | 3 | 8.7 | 2 | 2 |
| Comparative Example 2 | Comparative Compound 2 | Colored Composition 102 | Color Filter 102 | 2 | 8.5 | 2 | 2 |
| Comparative Example 3 | Comparative Compound 3 | Colored Composition 103 | Color Filter 103 | 4 | 10.7 | 3 | 3 |
| Comparative Example 4 | Comparative Compound 4 | Colored Composition 104 | Color Filter 104 | 4 | 10.9 | 3 | 3 |

As shown in Table 2, in the Examples, a significant improving effect that was more than expected was recognized in connection with the luminance (Y value), as compared with the Comparative Examples (Comparative Examples 1 and 2) in which conventionally known compounds were used. Furthermore, it is possible to maintain a high voltage retention ratio as compared with the Comparative Examples (Comparative Examples 3 and 4) in which conventionally known dipyrromethene-metal complex compounds were used.

From the results described above, it can be said that a color filter produced using the dipyrromethene-metal complex compound of the invention or a tautomer thereof has high performance such as general fastness properties (heat resistance and light resistance), good hues, and a high voltage retention ratio. Thus, the dipyrromethene-metal complex compound or a tautomer thereof of the invention can be considered as a dye with high general usability.

The invention claimed is:

1. A colored composition, comprising at least one selected from the group consisting of a compound represented by the following formula (I) and a tautomer thereof:

Formula (I)

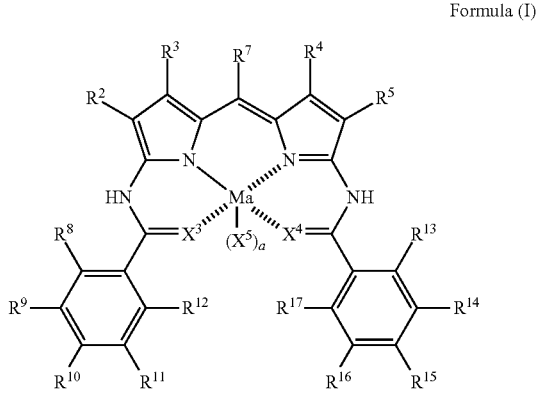

wherein, in formula (I), $R^2$ to $R^5$ each independently represent a hydrogen atom or a monovalent substituent; $R^7$ represents a hydrogen atom, a halogen atom, an alkyl group, an aryl group or a heterocyclic group; Ma represents a metal or a metal compound; $X^3$ and $X^4$ each independently represent NR, a nitrogen atom, an oxygen atom, or a sulfur atom, wherein R represents a hydrogen atom, an alkyl group, an alkenyl group, an aryl group, a heterocyclic group, an acyl group, an alkylsulfonyl group, or an arylsulfonyl group; $X^5$ represents a group required to neutralize the charge of Ma; a represents 1 or 2; when a is 2, respective $X^5$'s may be identical to or different from each other; and $R^8$ to $R^{17}$ each independently represent a hydrogen atom or a monovalent substituent, provided that at least one of $R^8$ to $R^{17}$ represents a substituent represented by the following formula (II):

Formula (II)

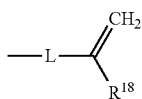

wherein, in formula (II), $R^{18}$ represents a hydrogen atom or a methyl group; L represents a single bond or a divalent linking group; and when the compound represented by formula (I) or a tautomer thereof has a plurality of substituents represented by formula (II), the respective substituents may be identical to or different from each other.

2. The colored composition according to claim 1, wherein, in formula (I), at least any one of $R^8$ to $R^{12}$ is a substituent represented by formula (II), and at least any one of $R^{13}$ to $R^{17}$ is a substituent represented by formula (II).

3. The colored composition according to claim 2, further comprising a polymerizable compound and a photopolymerization initiator.

4. The colored composition according to claim 2, further comprising a pigment or an anthraquinone compound, or comprising both a pigment and an anthraquinone compound.

5. The colored composition according to claim 4, wherein the anthraquinone compound is a compound represented by the following formula (IX):

Formula (IX)

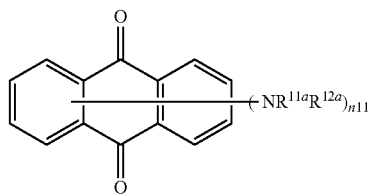

wherein, in formula (IX), $R^{11a}$ and $R^{12a}$ each independently represent a hydrogen atom, an alkyl group, an aryl group, or a heterocyclic group, but $R^{11a}$ and $R^{12a}$ do not simultaneously represent hydrogen atoms; $n^{11}$ represents an integer from 1 to 4; and when $n^{11}$ represents an integer from 2 to 4, plural $NR^{11a}R^{12a}$'s may be identical to or different from each other.

6. The colored composition according to claim 2, wherein a content of the at least one selected from the group consisting of a compound represented by formula (I) and a tautomer thereof is 0.1% to 30% by mass relative to the total solid content of the colored composition.

7. The colored composition according to claim 1, further comprising a polymerizable compound and a photopolymerization initiator.

8. The colored composition according to claim 1, further comprising a pigment or an anthraquinone compound, or comprising both a pigment and an anthraquinone compound.

9. The colored composition according to claim 8, wherein the anthraquinone compound is a compound represented by the following formula (IX):

Formula (IX)

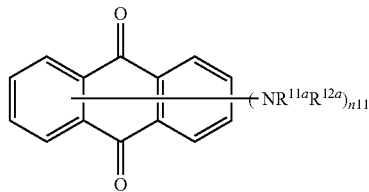

wherein, in formula (IX), $R^{11a}$ and $R^{12a}$ each independently represent a hydrogen atom, an alkyl group, an aryl group, or a heterocyclic group, but $R^{11a}$ and $R^{12a}$ do not simultaneously represent hydrogen atoms; $n^{11}$ represents an integer from 1 to 4; and when $n^{11}$ represents an integer from 2 to 4, plural $NR^{11a}R^{12a}$'s may be identical to or different from each other.

10. The colored composition according to claim 1, wherein a content of the at least one selected from the group consisting of a compound represented by formula (I) and a tautomer thereof is 0.1% to 30% by mass relative to the total solid content of the colored composition.

11. A colored cured film, obtained by curing the colored composition according to claim 1.

12. A color filter, comprising the colored cured film according to claim 11.

13. A liquid crystal display device, comprising the color filter according to claim 12.

14. A solid-state imaging device, comprising the color filter according to claim 12.

15. A method for producing a color filter, the method comprising: applying the colored composition according to claim 1 onto a support to form a colored layer; and exposing the formed colored layer in a pattern form and developing the colored layer to form a patterned colored cured film.

16. A compound represented by the following formula (I) or a tautomer thereof:

Formula (I)

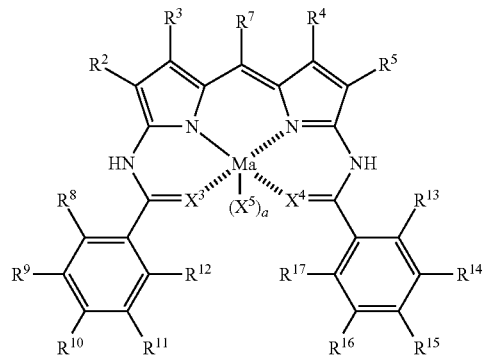

wherein, in formula (I), $R^2$ to $R^5$ each independently represent a hydrogen atom or a monovalent substituent; $R^7$ represents a hydrogen atom, a halogen atom, an alkyl group, an aryl group or a heterocyclic group; Ma represents a metal or a metal compound; $X^3$ and $X^4$ each independently represent NR, a nitrogen atom, an oxygen atom, or a sulfur atom, wherein R represents a hydrogen atom, an alkyl group, an alkenyl group, an aryl group, a heterocyclic group, an acyl group, an alkylsulfonyl group, or an arylsulfonyl group; $X^5$ represents a group required to neutralize the charge of Ma; a represents 1 or 2; when a is 2, respective $X^5$'s may be identical to or different from each other; and $R^8$ to $R^{17}$ each independently represent a hydrogen atom or a monovalent substituent, provided that at least one of $R^8$ to $R^{17}$ represents a substituent represented by the following formula (II):

Formula (II)

wherein, in formula (II), $R^{18}$ represents a hydrogen atom or a methyl group; L represents a single bond or a divalent linking group; and when the compound represented by formula (I) or a tautomer thereof has a plurality of substituents represented by formula (II), the respective substituents may be identical to or different from each other.

17. The compound or a tautomer thereof according to claim 16, wherein, in formula (I), at least any one of $R^8$ to $R^{12}$ is a substituent represented by formula (II), and at least any one of $R^{13}$ to $R^{17}$ is a substituent represented by formula (II).

* * * * *